(12) United States Patent
Uchida et al.

(10) Patent No.: US 8,952,003 B2
(45) Date of Patent: Feb. 10, 2015

(54) STEROL DERIVATIVE

(75) Inventors: Kenji Uchida, Shizuoka (JP); Tsutomu Agatsuma, Tokyo (JP); Kazuhiro Hibino, Tokyo (JP); Setsuya Sasho, Shizuoka (JP); Kyoichiro Iida, Kanagawa (JP); Hideyuki Onodera, Kanagawa (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 462 days.

(21) Appl. No.: 13/386,542

(22) PCT Filed: Jul. 22, 2010

(86) PCT No.: PCT/JP2010/062297
§ 371 (c)(1),
(2), (4) Date: Mar. 15, 2012

(87) PCT Pub. No.: WO2011/010682
PCT Pub. Date: Jan. 27, 2011

(65) Prior Publication Data
US 2012/0172348 A1    Jul. 5, 2012

(30) Foreign Application Priority Data
Jul. 24, 2009    (JP) .................. 2009-172886

(51) Int. Cl.
*A61K 31/55*    (2006.01)
*A61K 31/585*    (2006.01)
*C07J 73/00*    (2006.01)

(52) U.S. Cl.
CPC ............. *A61K 31/585* (2013.01); *C07J 73/003* (2013.01); *C07J 73/008* (2013.01)
USPC ... 514/212.06; 514/337; 514/453; 514/232.8; 549/275; 549/279; 540/521; 546/283.1; 544/150

(58) Field of Classification Search
CPC .... A61K 31/55; C07D 487/04; C07D 471/04; C07D 223/16; C07D 471/14
USPC .......... 514/212.06, 337, 453, 232.8; 549/275, 549/279; 540/521; 546/283.1; 544/150
See application file for complete search history.

(56) References Cited

U.S. PATENT DOCUMENTS

| | | |
|---|---|---|
| 2010/0105646 A1 | 4/2010 | Brinton et al. |
| 2010/0204192 A1 | 8/2010 | Brinton et al. |
| 2011/0020931 A1 | 1/2011 | Onodera et al. |

FOREIGN PATENT DOCUMENTS

| | | |
|---|---|---|
| EP | 2 239 320 A1 | 10/2010 |
| WO | 2008/071960 A2 | 6/2008 |
| WO | 2008/154579 A1 | 12/2008 |
| WO | 2009/073186 A1 | 6/2009 |
| WO | 2009/096445 A1 | 8/2009 |

OTHER PUBLICATIONS

Chung, Sangmi et al., "Neural Precursors Derived from Embryonic Stem Cells, but Not Those from Fetal Ventral Mesencephalon, Maintain the Potential to Differentiate into Dopaminergic Neurons After Expansion In Vitro," Stem Cells, 2006, vol. 24, pp. 1583-1593.

Keirstead, Hans S. et al., "Human Embryonic Stem Cell-Derived Oligodendrocyte Progenitor Cell Transplants Remyelinate and Restore Locomotion after Spinal Cord Injury," The Journal of Neuroscience, May 11, 2005, vol. 25(19), pp. 4694-4705.

Frank-Kamenetsky, Maria et al., "Small-molecule modulators of Hedgehog signaling: identification and characterization of Smoothened agonists and antagonists," Journal of Biology, Nov. 6, 2002, vol. 1, Issue 2, Article 10, p. 1-19.

Encinas, Juan M. et al., "Fluoxetine targets early progenitor cells in the adult brain," PNAS, May 23, 2006, vol. 103, No. 21, pp. 8233-8238.

Martino, Gianvito et al., "The therapeutic potential of neural stem cells," Nature Reviews—Neuroscience, vol. 7, May 2006, pp. 395-406.

(Continued)

*Primary Examiner* — Jason Sims
*Assistant Examiner* — Ibrahim D Bori
(74) *Attorney, Agent, or Firm* — Sughrue Mion, PLLC

(57) ABSTRACT

The present invention provides a sterol derivative or a pharmaceutically acceptable salt thereof having an activity to promote proliferation of neural stem cells. Namely, the present invention provides a sterol derivative represented by the general formula (I) (wherein Y represents optionally substituted lower alkyl or the like; $X^a$ and $X^b$ are the same or different, and represent a bond or the like; $R^1$, $R^2$, $R^3$, $R^4$, $R^7$ and $R^8$ are the same or different, and represent a hydrogen atom or the like; $R^5$ and $R^6$ are the same or different, and represent a hydrogen atom or the like; $R^9$ represents a hydrogen atom or the like; $R^{10}$ and $R^{11}$ together represent a bond or the like; and $R^{12}$ represents a hydrogen atom or the like) or a pharmaceutically acceptable salt thereof.

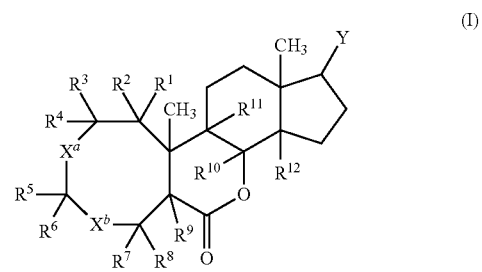

12 Claims, No Drawings

(56) References Cited

OTHER PUBLICATIONS

Yoshimizu, Takao et al., "Increased cell proliferation in the adult mouse hippocampus following chronic administration of group II metabotropic glutamate receptor antagonist, MGS0039," Biochemical and Biophyhsical Research Communications, vol. 315, 2004, pp. 493-496.

Santarelli, Luca et al., "Requirement of Hippocampal Neurogenesis for the Behavioral Effects of Antidepressants," Science, Aug. 8, 2003, vol. 301, pp. 805-809.

Wada, Koichiro et al., "Peroxisome Proliferator-activated Receptor y-mediated Regulation of Neural Stem Cell Proliferation and Differentiation," Journal of Biochemistry, May 5, 2006, vol. 281, No. 18, pp. 12673-12681.

Mincione, Enrico et al., "Synthesis Via Organoiron Complexes of 9-(4-Keto-1-Methylcyclohex-2-Enyl)-8-Keto-DES-AB-Ergost-22,23-ENE; A Useful Chiral Intermediate in Steroid Synthesis," Heterocycles, 1985, vol. 23, No. 7, pp. 1607-1610.

Rodewald, W.J. et al., "The Ruthenium Tetroxide Oxidation of Steroidal Conjugated Homoannular Dienes," Tetrahedron Letters, 1979, No. 33, pp. 3119-3122.

CAS Registry Database, SciFinder, Registry No. 6048-74-4, Feb. 15, 2012, 2 pages.

Joo, Jae-Yeol et al., "Activation of NMDA receptors increases proliferation and differentiation of hippocampal neural progenitor cells," Journal of Cell Science, 2007, vol. 120, No. 8, pp. 1358-1370.

Morisawa, Yasuhiro et al., "Steroid Series, Part XIV. Synthesis of 6-Aza- and 7-Aza-5*B*-steroids," Agricultural and Biological Chemistry, vol. 28, No. 11, 1964, pp. 788-795.

English-language abstract of Japanese Publication No. 2006-076948, published on Mar. 23, 2006.

International Search Report, issued by the International Searching Authority in corresponding International Application No. PCT/JP2010/062297 on Nov. 2, 2010.

Extended European Search Report, dated Mar. 15, 2013, issued by the European Patent Office in counterpart European Patent Application No. 10802302.9.

Song, Ching, et al., "Selective activation of liver X receptor alpha by 6α-hydroxy bile acids and analogs," Steroids, Elsevier Science Inc., vol. 65, No. 8, Aug. 1, 2000, pp. 423-427.

STEROL DERIVATIVE

TECHNICAL FIELD

The present invention relates to a sterol derivative having an activity to promote proliferation of neural stem cells.

BACKGROUND ART

Neurodegenerative diseases are diseases in which cerebral and peripheral nerve cells are damaged by a hereditary factor, an environmental factor, an aging factor and the like. Specifically, they include Parkinson's disease, Alzheimer's disease, triplet repeat disease, amyotrophic lateral sclerosis, polyneuropathy, spinal cord injury, cerebrovascular disorders and the like.

Although a general therapeutic method for these neurodegenerative diseases is a method in which neurotransmitters lost by the injury of nerve cells are supplemented, the diseases for which the therapeutic method is effective are limited to Parkinson's disease, Alzheimer's disease and the like at present. Additionally, the progress of nerve cell death cannot be stopped by the neurotransmitter supplementation method.

Regenerative medicine which regenerates the central nervous system has been investigated from the viewpoint of transplantation, as a therapeutic method for positively recovering the function of dopaminergic neurons which had lost by Parkinson's disease. However, the regenerative medicine has not been generally used due to various problems caused by the use of aborted fetal brain. Additionally, studies have also been conducted on a therapeutic method in which neural stem cells obtained from a fetal brain or ES cells obtained from a human fertilized eggs are mass-cultured in vitro and differentiated into a neuron of interest to use it for transplantation (*Stem Cells*, 2006, vol. 24, p. 1583-1593; *The Journal of Neuroscience*, 2005, vol. 25, p. 4694-4705). However, its clinical applications are not in progress since the techniques for accurately differentiating them into the desired neuron have not been established yet; teratomas are formed by undifferentiated cells; and there are problems caused by the use of fetal neural stem cells or human ES cells. Accordingly, a technique in which adult-derived neural stem cells are cultured in vitro and used for transplantation is regarded as a promising technique and search for factors which efficiently accelerate proliferation of neural stem cells is expected (*Nature Reviews Neuroscience*, 2006, vol. 7, p. 395-406).

As a low molecular compound which promotes proliferation of neural stem cells, for example, Salvianolic acid B (JP2006-76948), hedgehog signal agonists (*Journal of Biology*, 2002, vol. 1, p. 10), selective serotonin reuptake inhibitors (Science, 2003, vol. 301, p. 805-809; *Proceedings of the National Academy of Science of the United States of America*, 2006, vol. 103, p. 8233-8238), metabotropic glutamate receptor antagonists (*Biochemical and Biophysical Research Communications*, 2004, vol. 315, p. 493-496), PPARγ agonists (*The Journal of Biological Chemistry*, 2006, vol. 281, p. 12673-12681), NMDA agonists (*Journal of Cell Science*, 2007, vol. 120, p. 1358-1370) and the like have been reported.

On the other hand, as a sterol derivative, the following compounds (1) to (4) are known (see Non-Patent Literatures 1 to 4).

[Chem. 1]

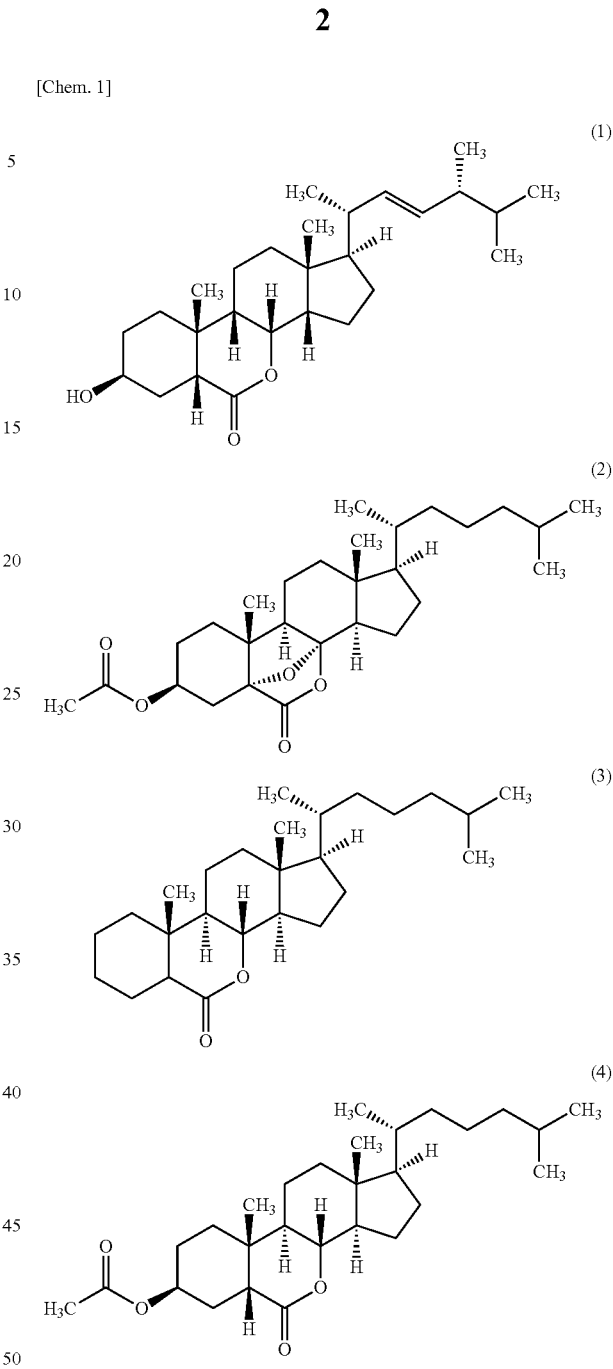

PRIOR ART DOCUMENTS

Non-Patent Literature

Non-Patent Literature 1: Heterocycles, 1985, vol. 23, p. 1607-1610

Non-Patent Literature 2: Tetrahedron Letters, 1979, vol. 20, p. 3119-3122

Non-Patent Literature 3: CAS REGISTRY Database, Registry Number: 6048-74-4

Non-Patent Literature 4: Agricultural and Biological Chemistry, 1964, vol. 28, p. 788-795

DISCLOSURE OF THE INVENTION

Problems to be Solved by the Invention

The object of the present invention is to provide a sterol derivative having an activity to promote proliferation of neural stem cells or a pharmaceutically acceptable salt thereof.

Means for Solving the Problems

The present invention relates to the following (1) to (16).
(1) A sterol derivative represented by the general formula (I):

[Chem. 2]

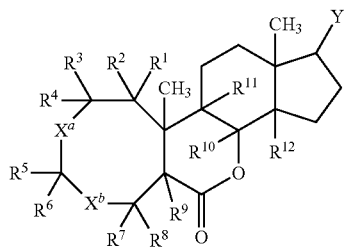

(I)

[wherein Y represents optionally substituted lower alkyl or optionally substituted lower alkenyl, $X^a$ and $X^b$ are the same or different, and represent a bond or —$NR^a$— (wherein $R^a$ represents a hydrogen atom, optionally substituted lower alkyl, optionally substituted cycloalkyl, optionally substituted lower alkanoyl, or optionally substituted aroyl), $R^1$, $R^2$, $R^3$, $R^4$, $R^7$ and $R^8$ are the same or different, and represent a hydrogen atom or hydroxy, or $R^1$ and $R^2$, $R^3$ and $R^4$, or $R^7$ and $R^8$ together represent =O, $R^5$ and $R^6$ are the same or different, and represent a hydrogen atom, halogen, azido, hydroxy, optionally substituted lower alkoxy, optionally substituted cycloalkyloxy, optionally substituted lower alkenyloxy, optionally substituted lower alkynyloxy, optionally substituted aryloxy, optionally substituted aromatic heterocyclyloxy, optionally substituted aliphatic heterocyclyloxy, optionally substituted lower alkanoyloxy, optionally substituted aroyloxy, optionally substituted aromatic heterocyclylcarbonyloxy, or —$NR^bR^c$ (wherein $R^b$ and $R^c$ are the same or different, and represent a hydrogen atom, optionally substituted lower alkyl, optionally substituted lower alkenyl, optionally substituted cycloalkyl, optionally substituted aryl, an optionally substituted aromatic heterocyclic group, an optionally substituted aliphatic heterocyclic group, optionally substituted lower alkanoyl, optionally substituted aroyl, optionally substituted lower alkoxycarbonyl, optionally substituted aryloxycarbonyl, optionally substituted aromatic heterocyclyloxycarbonyl, optionally substituted lower alkylcarbamoyl, optionally substituted di-lower alkylcarbamoyl, optionally substituted arylcarbamoyl, optionally substituted aromatic heterocyclylcarbamoyl, optionally substituted arylsulfonyl, or optionally substituted lower alkylsulfonyl), or $R^5$ and $R^6$ together represent O=, $R^dON$= (wherein $R^d$ represents a hydrogen atom, optionally substituted lower alkyl, optionally substituted cycloalkyl, optionally substituted aryl, an optionally substituted aromatic heterocyclic group, or an optionally substituted aliphatic heterocyclic group), or $R^eR^fC$= (wherein $R^e$ and $R^f$ are the same or different, and represent a hydrogen atom, halogen, optionally substituted lower alkyl, optionally substituted lower alkenyl, optionally substituted lower alkynyl, optionally substituted cycloalkyl, optionally substituted aryl, an optionally substituted aromatic heterocyclic group, an optionally substituted aliphatic heterocyclic group, optionally substituted lower alkoxy, optionally substituted aryloxy, optionally substituted aromatic heterocyclyloxy, optionally substituted lower alkanoyl, optionally substituted aroyl, optionally substituted lower alkanoyloxy, or optionally substituted aroyloxy), $R^9$ represents a hydrogen atom, optionally substituted lower alkyl, optionally substituted lower alkenyl, optionally substituted lower alkynyl, or optionally substituted cycloalkyl, or $R^1$ and $R^3$, $R^3$ and $R^5$ (provided that this is only when $X^a$ is a bond), $R^5$ and $R^7$ (provided that this is only when $X^b$ is a bond), or $R^7$ and $R^9$ together represent a bond or an oxygen atom, and regarding $R^{10}$, $R^{11}$ and $R^{12}$, $R^{10}$ and $R^{11}$ together represent a bond or an oxygen atom and $R^{12}$ represents an oxygen atom, or $R^{10}$ and $R^{12}$ together represent a bond or an oxygen atom and $R^{12}$ represents a hydrogen atom] (provided that compounds represented by the following formulas (P) and (Q) are excluded), or a pharmaceutically acceptable salt thereof.

[Chem. 3]

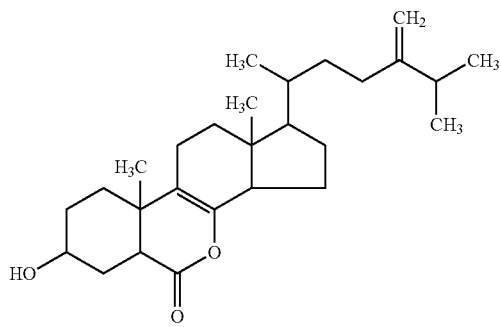

(P)

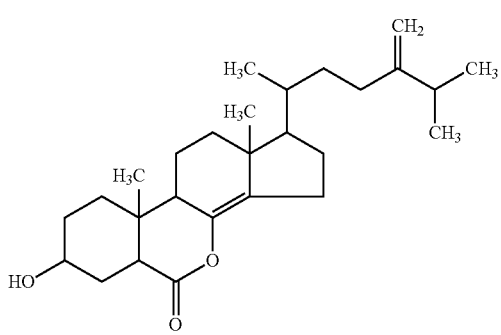

(Q)

(2) The sterol derivative or the pharmaceutically acceptable salt thereof described in (1), wherein $R^{10}$ and $R^{11}$ together represent a bond and $R^{12}$ is a hydrogen atom.
(3) The sterol derivative or the pharmaceutically acceptable salt thereof described in (1) or (2), wherein $X^a$ and $X^b$ are bonds.
(4) The sterol derivative or the pharmaceutically acceptable salt thereof described in any one of (1) to (3), wherein $R^7$ and $R^8$ are hydrogen atoms.
(5) The sterol derivative or the pharmaceutically acceptable salt thereof described in any one of (1) to (4), wherein $R^5$ is a hydrogen atom.

(6) The sterol derivative or the pharmaceutically acceptable salt thereof described in any one of (1) to (5), wherein $R^6$ is hydroxy, optionally substituted lower alkoxy, optionally substituted cycloalkyloxy, optionally substituted lower alkenyloxy, optionally substituted lower alkynyloxy, optionally substituted aryloxy, optionally substituted aromatic heterocyclyloxy, optionally substituted aliphatic heterocyclyloxy, optionally substituted lower alkanoyloxy, optionally substituted aroyloxy, or —$NR^{b1}R^{c1}$ (wherein $R^{b1}$ and $R^{c1}$ are the same or different, and represent a hydrogen atom, optionally substituted lower alkyl, optionally substituted lower alkanoyl, or optionally substituted aroyl).

(7) The sterol derivative or the pharmaceutically acceptable salt thereof described in any one of (1) to (5), wherein $R^6$ is hydroxy, optionally substituted lower alkoxy, optionally substituted aryloxy, optionally substituted aromatic heterocyclyloxy, optionally substituted aliphatic heterocyclyloxy, or —$NR^{b1}R^{c1}$ (wherein $R^{b1}$ and $R^{c1}$ have the same meanings as defined above, respectively)

(8) The sterol derivative or the pharmaceutically acceptable salt thereof described in any one of (1) to (5), wherein $R^6$ is hydroxy or optionally substituted lower alkoxy.

(9) The sterol derivative or the pharmaceutically acceptable salt thereof described in any one of (1) to (4), wherein $R^5$ and $R^6$ together represent O= or $R^dON=$ (wherein $R^d$ has the same meaning as defined above).

(10) The sterol derivative or the pharmaceutically acceptable salt thereof described in any one of (1) to (9), wherein $R^9$ is a hydrogen atom or optionally substituted lower alkyl.

(11) The sterol derivative or the pharmaceutically acceptable salt thereof described in any one of (1) to (10), wherein Y is optionally substituted lower alkyl.

(12) The sterol derivative or the pharmaceutically acceptable salt thereof described in any one of (1) to (10), wherein Y is lower alkyl.

(13) A proliferation promoting agent for neutral stem cells, comprising the compound or the pharmaceutically acceptable salt thereof described in any one of (1) to (12) as an active ingredient.

(14) A method for promoting proliferation of neutral stem cells, comprising administering an effective amount of the compound or the pharmaceutically acceptable salt thereof described in any one of (1) to (12).

(15) The compound or the pharmaceutically acceptable salt thereof described in any one of (1) to (12) for use in promoting proliferation of neural stem cells.

(16) Use of the compound or the pharmaceutically acceptable salt thereof described in any one of (1) to (12) for manufacture of a proliferation promoting agent for neural stem cells.

Effects of the Invention

The present invention can provide a sterol derivative having an activity to promote proliferation of neural stem cells or a pharmaceutically acceptable salt thereof.

EMBODIMENTS FOR CARRYING OUT THE INVENTION

Hereinafter, a compound represented by the general formula (I) will be referred to as compound (I). The same applies to compounds of other formula numbers.

In the definition of each group in the general formula (I), examples of the lower alkyl, and the lower alkyl moiety of the lower alkoxy, the lower alkanoyl, the lower alkoxycarbonyl, the lower alkanoyloxy, the lower alkylcarbamoyl, the di-lower alkylcarbamoyl and the lower alkylsulfonyl may include, for example, linear or branched alkyl having 1 to 10 carbon atoms, and more specific examples thereof may include methyl, ethyl, propyl, isopropyl, butyl, isobutyl, sec-butyl, tert-butyl, pentyl, isopentyl, neopentyl, hexyl, heptyl, octyl, nonyl, decyl and the like. Two lower alkyl moieties of the di-lower alkylcarbamoyl may be the same or different.

Examples of the lower alkenyl, and the lower alkenyl moiety of the lower alkenyloxy may include, for example, linear or branched alkenyl having 2 to 10 carbon atoms, and more specific examples thereof may include vinyl, allyl, 1-propenyl, 1-butenyl, 2-butenyl, 3-butenyl, pentenyl, hexenyl, heptenyl, octenyl, nonenyl, decenyl and the like.

Examples of the lower alkynyl, and the lower alkynyl moiety of the lower alkynyloxy may include, for example, linear or branched alkynyl having 2 to 10 carbon atoms, and more specific examples thereof may include ethynyl, propynyl, butynyl, pentynyl, hexynyl, heptynyl, octynyl, nonynyl, decynyl and the like.

Examples of the cycloalkyl, and the cycloalkyl moiety of the cycloalkyloxy may include, for example, cycloalkyl having 3 to 8 carbon atoms, and more specific examples thereof may include cyclopropyl, cyclobutyl, cyclopentyl, cyclohexyl, cycloheptyl, cyclooctyl and the like.

Examples of the aryl, and the aryl moiety of the aryloxy, the aroyl, the aroyloxy, the aryloxycarbonyl, the arylcarbamoyl and the arylsulfonyl may include, for example, aryl having 6 to 14 carbon atoms, and more specific examples thereof may include phenyl, naphtyl, azulenyl, anthryl and the like.

Examples of the aliphatic heterocyclic group, and the aliphatic heterocyclic group moiety of the aliphatic heterocyclyloxy may include a 5-membered or 6-membered monocyclic aliphatic heterocyclic group including at least one atom selected from a nitrogen atom, an oxygen atom and a sulfur atom, a bicyclic or tricyclic condensed aliphatic heterocyclic group containing at least one atom selected from a nitrogen atom, an oxygen atom and a sulfur atom, wherein 3- to 8-membered rings are condensed, and the like, and more specific examples thereof may include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like.

Examples of the aromatic heterocyclic group, and the aromatic heterocyclic group moiety of the aromatic heterocyclyloxy, the aromatic heterocyclylcarbonyloxy, the aromatic heterocyclyloxycarbonyl and the aromatic heterocyclylcarbamoyl may include a 5-membered or 6-membered monocyclic aromatic heterocyclic group containing at least one atom selected from a nitrogen atom, an oxygen atom, and a sulfur atom, a bicyclic or tricyclic condensed aromatic heterocyclic group containing at least one atom selected from a nitrogen atom, an oxygen atom and a sulfur atom, wherein 3- to 8-membered rings are condensed, and the like, and more specific examples thereof may include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl and the like.

The halogen means each atom of fluorine, chlorine, bromine or iodine.

The substituents of the optionally substituted lower alkyl, the optionally substituted lower alkenyl, the optionally substituted lower alkynyl, the optionally substituted lower alkoxy, the optionally substituted lower alkenyloxy, the optionally substituted lower alkynyloxy, the optionally substituted lower alkanoyloxy, the optionally substituted lower alkanoyl, the optionally substituted lower alkoxycarbonyl, the optionally substituted lower alkylcarbamoyl, the optionally substituted di-lower alkylcarbamoyl and the optionally substituted lower alkylsulfonyl), may be the same or different, and may include, for example, 1 to 3 substituent(s) selected from the group consisting of halogen; hydroxy; sulfanyl; nitro; azido; cyano; carboxyl; carbamoyl; formyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; an aliphatic heterocyclic group; an aromatic heterocyclic group; $C_{1-40}$ alkoxy optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{2-10}$ alkenyloxy; $C_{3-8}$ cycloalkoxy; $C_{6-14}$ aryloxy optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{7-16}$ aralkyloxy optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{2-11}$ alkanoyloxy; $C_{7-15}$ aroyloxy; $C_{1-10}$ alkylsulfonyloxy; trifluoromethanesulfonyloxy; $C_{6-14}$ arylsulfonyloxy; p-toluenesulfonyloxy; $C_{1-10}$ alkylsulfanyl; $C_{6-14}$ arylsulfanyl; —NR$^{Ya}$R$^{Ya}$ (wherein R$^{Ya}$ and R$^{Ya}$ are the same or different, and represent a hydrogen atom; formyl; $C_{1-10}$ alkyl optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; an aromatic heterocyclic group; $C_{7-16}$ aralkyl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{2-11}$ alkanoyl optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{7-15}$ aroyl; $C_{1-10}$ alkoxycarbonyl; $C_{7-16}$ aralkyloxycarbonyl; $C_{1-10}$ alkylcarbamoyl, di-$C_{1-10}$ alkylcarbamoyl, $C_{6-14}$ arylcarbamoyl, $C_{1-10}$ alkylsulfonyl; trifluoromethanesulfonyl; $C_{6-14}$ arylsulfonyl or p-toluenesulfonyl); $C_{2-11}$ alkanoyl; $C_{3-8}$ cycloalkylcarbonyl; $C_{7-15}$ aroyl; aliphatic heterocyclylcarbonyl; aromatic heterocyclylcarbonyl; $C_{1-10}$ alkoxycarbonyl; $C_{6-14}$ aryloxycarbonyl; $C_{7-16}$ aralkyloxycarbonyl; $C_{1-10}$ alkylcarbamoyl optionally substituted by 1 to 3 substituent(s) selected from the group consisting of hydroxy, halogen, $C_{1-10}$ alkoxy, amino, $C_{1-10}$ alkylamino, di-$C_{1-10}$ alkylamino, $C_{2-11}$ alkanoylamino and $C_{1-10}$ alkoxycarbonylamino; di-$C_{1-10}$ alkylcarbamoyl optionally substituted by 1 to 3 substituent(s) selected from the group consisting of hydroxy, halogen, $C_{1-10}$ alkoxy, amino, $C_{1-10}$ alkylamino, di-$C_{1-10}$ alkylamino, $C_{2-11}$ alkanoylamino and $C_{1-10}$ alkoxycarbonylamino; and $C_{6-14}$ arylcarbamoyl.

The substituents of the optionally substituted aryl, the optionally substituted aryloxy, the optionally substituted aroyl, the optionally substituted aroyloxy, the optionally substituted aryloxycarbonyl, the optionally substituted arylcarbamoyl, the optionally substituted arylsulfonyl, the optionally substituted aromatic heterocyclic group, the optionally substituted aromatic heterocyclyloxy, the optionally substituted aromatic heterocyclylcarbonyloxy, the optionally substituted aromatic heterocyclyloxycarbonyl, and the optionally substituted aromatic heterocyclylcarbamoyl may be the same or different, and may include, for example, 1 to 5 substituent(s) selected from the group consisting of halogen; hydroxy; sulfanyl; nitro; cyano; carboxyl; carbamoyl; $C_{1-10}$ alkyl; trifluoromethyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; an aliphatic heterocyclic group; an aromatic heterocyclic group; $C_{1-10}$ alkoxy optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{3-8}$ cycloalkoxy; $C_{6-14}$ aryloxy optionally substituted by 1 to 3 substituent(s) selected from the group consisting of halogen, hydroxy, amino, nitro, carboxyl, $C_{1-10}$ alkoxycarbonyl, alkoxy and trifluoromethyl; $C_{7-16}$ aralkyloxy optionally substituted by 1 to 3 substituent(s) selected from the group consisting of halogen, hydroxy, amino, nitro, carboxyl, $C_{1-10}$ alkoxycarbonyl, alkoxy and trifluoromethyl; $C_{2-11}$ alkanoyloxy; $C_{7-15}$ aroyloxy; $C_{1-10}$ alkylsulfonyloxy; trifluoromethanesulfonyloxy; $C_{6-14}$ arylsulfonyloxy; p-toluenesulfonyloxy; $C_{1-10}$ alkylsulfanyl; $C_{6-14}$ arylsulfanyl; —NR$^{Xb}$R$^{Yb}$ (wherein R$^{Xb}$ and R$^{Yb}$ are the same or different, and represent a hydrogen atom; formyl; $C_{1-10}$ alkyl optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, alkoxy and trifluoromethyl; an aromatic heterocyclic group; $C_{7-16}$ aralkyl optionally substituted by 1 to 3 substituent(s) selected from the group consisting of halogen, hydroxy, amino, nitro, carboxyl, $C_{1-10}$ alkoxycarbonyl, alkoxy and trifluoromethyl; $C_{2-11}$ alkanoyl optionally substituted by 1 to 3 substituent(s) selected from the group consisting of halogen, hydroxy, amino, carboxyl, $C_{1-10}$ alkoxy, alkylamino, di-$C_{1-10}$ alkylamino and $C_{1-10}$ alkoxycarbonyl; $C_{7-15}$ aroyl; $C_{1-10}$ alkoxycarbonyl; $C_{7-16}$ aralkyloxycarbonyl; $C_{1-10}$ alkylsulfonyl; trifluoromethanesulfonyl; $C_{6-14}$ arylsulfonyl or p-toluenesulfonyl); $C_{2-11}$ alkanoyl; $C_{3-8}$ cycloalkylcarbonyl; $C_{7-15}$ aroyl; aliphatic heterocyclylcarbonyl; aromatic heterocyclylcarbonyl; alkoxycarbonyl; $C_{6-14}$ aryloxycarbonyl; $C_{7-16}$ aralkyloxycarbonyl; alkylcarbamoyl; di-$C_{1-10}$ alkylcarbamoyl; $C_{6-14}$ arylcarbamoyl; $C_{1-10}$ alkylsulfonyl; and $C_{6-14}$ arylsulfonyl.

The substituents of the optionally substituted cycloalkyl, the optionally substituted cycloalkyloxy, the optionally substituted aliphatic heterocyclic group and the optionally substituted aliphatic heterocyclyloxy may be the same or different, and may include, for example, 1 to 5 substituent(s) selected from the group consisting of oxo; halogen; hydroxy; sulfanyl; nitro; cyano; carboxyl; carbamoyl; $C_{1-10}$ alkyl optionally substituted by 1 to 3 hydroxy groups; trifluoromethyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; an aliphatic heterocyclic group; an aromatic heterocyclic group; $C_{1-10}$ alkoxy optionally substituted by 1 to 3 substituent(s) selected from the group consisting of halogen, hydroxy, amino, carboxyl, $C_{1-10}$ alkoxy, $C_{1-10}$ alkylamino, alkylamino and $C_{1-10}$ alkoxycarbonyl; $C_{3-8}$ cycloalkoxy; $C_{6-14}$ aryloxy optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{7-16}$ aralkyloxy optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{2-11}$ alkanoyloxy; $C_{7-15}$ aroyloxy; $C_{1-10}$ alkylsulfonyloxy; trifluoromethanesulfonyloxy; $C_{6-14}$ arylsulfonyloxy; p-toluenesulfonyloxy; $C_{1-10}$ alkylsulfanyl; $C_{6-14}$ arylsulfanyl; —$NR^{Xc}R^{Yc}$ (wherein $R^{Xc}$ and $R^{Yc}$ are the same or different, and represent a hydrogen atom; formyl; $C_{1-10}$ alkyl optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{3-8}$ cycloalkyl; $C_{6-14}$ aryl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; an aromatic heterocyclic group; $C_{7-16}$ aralkyl optionally substituted by 1 to 3 substituent(s) selected from the group consisting of halogen, hydroxy, amino, nitro, carboxyl, $C_{1-10}$ alkoxycarbonyl, $C_{1-10}$ alkoxy and trifluoromethyl; $C_{2-11}$ alkanoyl optionally substituted by 1 to 3 substituent(s) selected from the group consisting of halogen, hydroxy, amino, carboxyl, $C_{1-10}$ alkoxy, $C_{1-10}$ alkylamino, di-$C_{1-10}$ alkylamino and $C_{1-10}$ alkoxycarbonyl; $C_{7-15}$ aroyl; $C_{1-10}$ alkoxycarbonyl; $C_{7-16}$ aralkyloxycarbonyl; $C_{1-10}$ alkylsulfonyl; trifluoromethanesulfonyl; $C_{6-14}$ arylsulfonyl or p-toluenesulfonyl), $C_{2-11}$ alkanoyl; $C_{3-8}$ cycloalkylcarbonyl; $C_{7-15}$ aroyl; aliphatic heterocyclylcarbonyl; aromatic heterocyclylcarbonyl; $C_{1-10}$ alkoxycarbonyl; $C_{6-14}$ aryloxycarbonyl; $C_{7-16}$ aralkyloxycarbonyl; $C_{1-10}$ alkylcarbamoyl; di-$C_{1-10}$ alkylcarbamoyl; $C_{6-14}$ arylcarbamoyl; $C_{1-10}$ alkylsulfonyl; and $C_{6-14}$ arylsulfonyl.

Examples of the $C_{1-10}$ alkyl, and the $C_{1-10}$ alkyl moiety of the $C_{1-10}$ alkoxy, the $C_{2-11}$ alkanoyloxy, the $C_{1-10}$ alkylsulfanyl, the di-$C_{1-10}$ alkylamino, the $C_{2-11}$ alkanoylamino, the $C_{1-10}$ alkoxycarbonylamino, the $C_{2-11}$ alkanoyl, the $C_{1-10}$ alkoxycarbonyl, the $C_{1-10}$ alkylcarbamoyl, the di-$C_{1-10}$ alkylcarbamoyl, the $C_{1-10}$ alkylsulfonyl, and the $C_{1-10}$ alkylsulfonyloxy as mentioned herein include the groups recited as examples of the aforementioned lower alkyl. Two $C_{1-10}$ alkyl groups of the di-$C_{1-10}$ alkylamino and the di-$C_{1-10}$ alkylcarbamoyl may be the same or different.

Examples of the $C_{2-10}$ alkenyl moiety of the $C_{2-10}$ alkenyloxy include the groups recited as examples of the aforementioned lower alkenyl.

Examples of the $C_{3-8}$ cycloalkyl, and the $C_{3-8}$ cycloalkyl moiety of the $C_{3-8}$ cycloalkoxy and the $C_{3-8}$ cycloalkylcarbonyl include the groups recited as examples of the aforementioned cycloalkyl.

Examples of the $C_{6-14}$ aryl, and the $C_{6-14}$ aryl moiety of the $C_{6-14}$ aryloxy, the $C_{7-15}$ aroyloxy, the $C_{6-14}$ arylsulfanyl, the $C_{6-14}$ arylsulfonyl, the $C_{7-15}$ aroyl, the $C_{6-14}$ aryloxycarbonyl, the $C_{6-14}$ aryloxycarbamoyl, the $C_{6-14}$ arylsulfonyl and the $C_{6-14}$ arylsulfonyloxy include the groups recited as examples of the aforementioned aryl.

Examples of the aryl moiety of the $C_{7-16}$ aralkyloxy, the $C_{7-16}$ aralkyl and the $C_{7-16}$ aralkyloxycarbonyl include the groups recited as examples of the aforementioned aryl, examples of the alkyl moiety thereof include $C_{1-10}$ alkylene, and more specifically, may include a group obtained by removing one hydrogen atom from the groups recited as examples of the aforementioned lower alkyl.

Examples of the aliphatic heterocyclic group and the aliphatic heterocyclic group moiety of the aliphatic heterocyclylcarbonyl, the aromatic heterocyclic group and the aromatic heterocyclic group moiety of the aromatic heterocyclylcarbonyl, and the halogen may include the groups recited as examples of the aforementioned aliphatic heterocyclic group, the aforementioned aromatic heterocyclic group, and the aforementioned halogen, respectively.

In the general formula (I), in addition to the aforementioned (1) to (12), Y is, for example, preferably $C_{1-10}$ alkyl, and more preferably $C_{1-10}$ alkyl which is substituted at position 2 (the following formula (II)), and the like. These preferable group may optionally substituted with hydroxy, $C_{1-10}$ alkoxy, $C_{2-10}$ alkenyloxy, $C_{2-11}$ alkanoyloxy, $C_{1-10}$ alkylamino, di-$C_{1-10}$ alkylamino and the like, and preferably, may be substituted with, for example, hydroxy, $C_{1-4}$ alkoxy, $C_{2-4}$ alkenyloxy, $C_{2-5}$ alkanoyloxy, $C_{1-4}$ alkylamino, di-$C_{1-4}$ alkylamino, and the like.

[Chem. 4]

(II)

(wherein $Y^A$ represents $C_{1-8}$ alkyl)

$R^5$ is, for example, preferably a hydrogen atom and the like, and $R^6$ is, for example, preferably hydroxy, $C_{1-10}$ alkoxy, $C_{6-14}$ aryloxy, aliphatic heterocyclyloxy, aromatic heterocyclyloxy, amino, $C_{1-10}$ alkylamino, $C_{2-11}$ alkanoylamino, $C_{6-14}$ arylcarbonylamino, and the like, more preferably hydroxy, $C_{1-10}$ alkoxy, and the like, and still more preferably hydroxy, $C_{1-4}$ alkoxy, and the like. Further, groups thereof may be substituted with 1 to 3 substituent(s), and the substituent(s) thereof include, for example, hydroxy, $C_{1-10}$ alkoxy, $C_{2-10}$ alkenyloxy, $C_{2-11}$ alkanoyloxy, amino, $C_{1-10}$ alkylamino, di-$C_{1-10}$ alkylamino, $C_{2-11}$ alkanoylamino, pyrrolidinyl, piperidino, morpholino, and the like, preferably, for example, hydroxy, $C_{1-10}$ alkoxy, and the like, still more preferably, for example, hydroxy, $C_{1-4}$ alkoxy and the like, and further more preferably, for example, hydroxy, methoxy, and the like.

$R^9$ is, for example, preferably a hydrogen atom, $C_{1-10}$ alkyl, $C_{1-10}$ alkyl substituted with 1 to 2 hydroxy group(s), and the like, more preferably a hydrogen atom, $C_{1-4}$ alkyl, $C_{1-4}$ alkyl substituted with 1 to 2 hydroxy group(s), and the like, and still more preferably a hydrogen atom, and the like.

Example of the pharmaceutically acceptable salt of Compound (I) include pharmaceutically acceptable acid addition salts, metal salts, ammonium salts, organic amine addition salts, amino acid addition salts, and the like. Examples of the pharmaceutically acceptable acid addition salt of Compound (I) include an inorganic salt such as a hydrochloride, a hydrobromate, a nitrate, a sulfate and a phosphate, an organic acid salt such as an acetate, an oxalate, a maleate, a fumarate, a citrate, a benzoate, a methanesulfonate and the like. Examples of the pharmaceutically acceptable metal salt include an alkaline metal salt such as a sodium salt and a potassium salt, an alkaline-earth metal salt such as a magnesium salt and a calcium salt, an aluminium salt, a zinc salt, and the like. Examples of the pharmaceutically acceptable ammonium salt include a salt of ammonium, tetramethylammonium, and the like. Examples of the pharmaceutically acceptable organic amine addition salt include an addition salt of morpholine, piperidine, or the like. Examples of the pharmaceutically acceptable amino acid addition salt include an addition salt of lysine, glycine, phenylalanine, asparagic acid, glutamic acid, and the like.

Next, a preparation method of the compound of the present invention is described.

In the preparing methods as shown below, when the defined group changes under the conditions of the method carried out, or the method is inappropriate for carrying out, the desired compound can be obtained by using the protection and deprotection of the groups which are ordinarily used in the synthetic organic chemistry [e.g., *Protective Groups in Organic Synthesis, third edition*, T. W. Greene, John Wiley & Sons Inc. (1999)] and the like. In addition, the order of the steps for introducing a substituent and the like may be changed, if necessary.

Preparation Method 1

Among compounds (I), compounds (I-a) and (I-b) in the following scheme may be prepared, for example, according to the following steps.

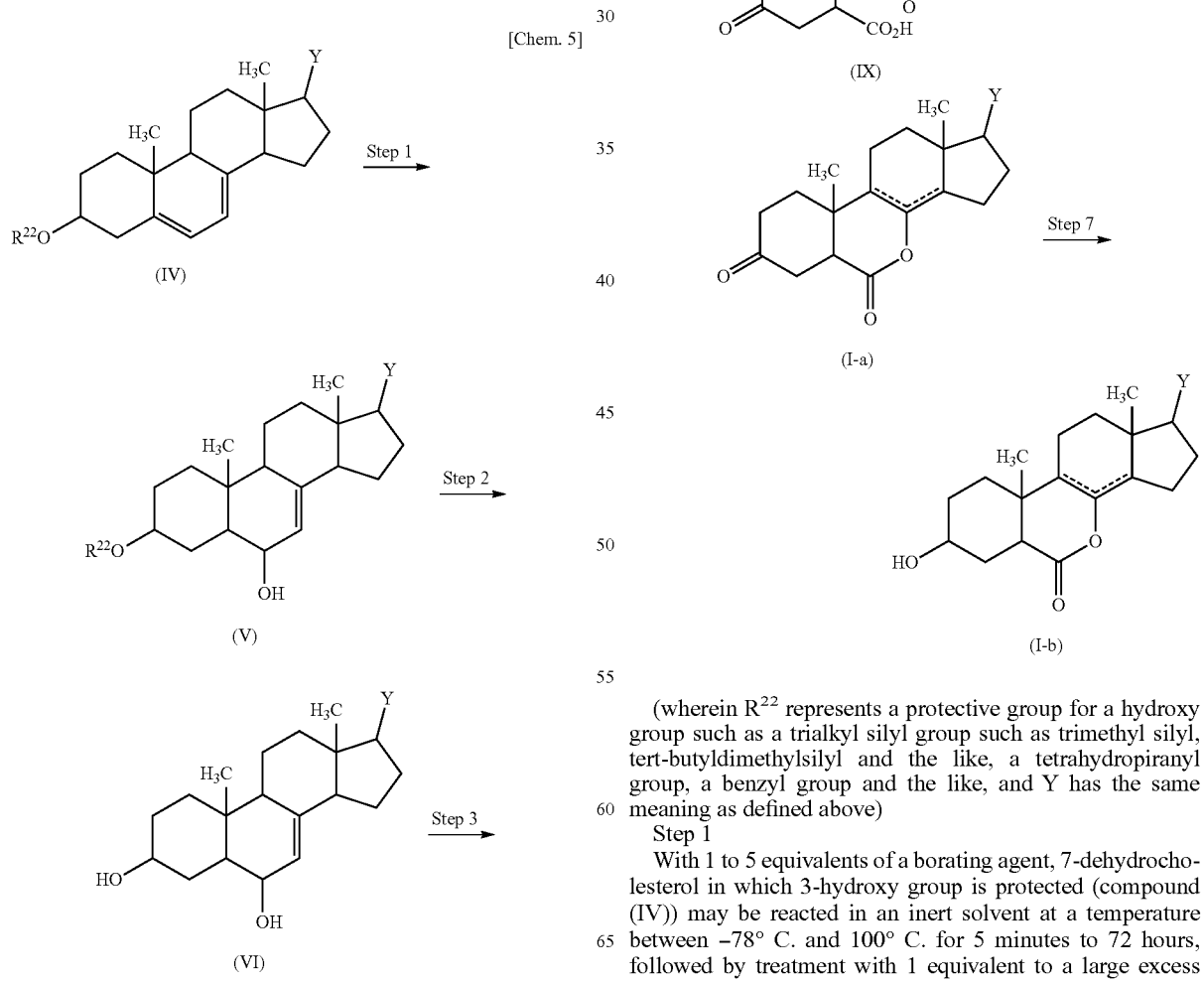

(wherein $R^{22}$ represents a protective group for a hydroxy group such as a trialkyl silyl group such as trimethyl silyl, tert-butyldimethylsilyl and the like, a tetrahydropiranyl group, a benzyl group and the like, and Y has the same meaning as defined above)

Step 1

With 1 to 5 equivalents of a borating agent, 7-dehydrocholesterol in which 3-hydroxy group is protected (compound (IV)) may be reacted in an inert solvent at a temperature between −78° C. and 100° C. for 5 minutes to 72 hours, followed by treatment with 1 equivalent to a large excess amount of an oxidizing agent in the presence of a suitable base at a temperature between −78° C. and 100° C. for 5 minutes to 72 hours to prepare compound (V).

Examples of the inert solvent include diethyl ether, tetrahydrofuran (THF), dioxane, N,N-dimethylformamide (DMF), N,N-dimethylacetamide (DMA), dimethylsulfoxide (DMSO), benzene, toluene, xylene, dichloromethane, chloroform, water and the like, and these may be used in combination. Examples of the borating agent include, a borane-tetrahydrofuran complex, methylborane, a borane-dimethylsulfide complex, 9-borabicyclo[3.3.1]nonane, catecholborane and the like. Examples of the base may include sodium hydroxide, potassium hydroxide, calcium hydroxide, potassium carbonate and the like. Examples of the oxidizing agent include hydrogen peroxide, oxygen, and the like.

Compound (IV) may be obtained by protecting 3-hydroxy group in 7-dehydrocholesterol which is obtained as, for example, a commercially available product with such as a trialkyl silyl group according to methods described in, for example, T. W. Greene, *Protective Groups in Organic Synthesis*, Third Edition, John Wiley & Sons Inc. (1999), and the like. Further, compound (IV) may be obtained according to methods described in, for example, *Organic Letters* (2003), vol. 5, p. 1837-1839 or *Chemistry-A European Journal* (2001), vol. 7, p. 2663-2670, and the like.

Step 2

Compound (VI) may be prepared by deprotecting compound (V) obtained in the Step 1 according to the method described in T. W. Greene, Protective Groups in Organic Synthesis, Third Edition, John Wiley & Sons Inc. (1999).

Step 3

Compound (VII) may be obtained by reacting compound (VI) obtained in the Step 2 with 1 equivalent to a large excess amount of a suitable oxidizing agent in the presence of, if necessary, an additive in an inert solvent at a temperature between −20° C. and 100° C. for 5 minutes to 72 hours.

Examples of the inert solvent include diethyl ether, THF, dioxane, DMF, DMA, DMSO, dichloromethane, chloroform, carbon tetrachloride, dichloroethane, benzene, toluene, xylene, ethyl acetate, acetic acid, propionic acid, butyric acid, trifluoroacetic acid, water, pyridine and the like, and these may be used in combination. Examples of the oxidizing agent include tetrapropylammonium perruthenate, 4-methylmorpholine-N-oxide, manganese dioxide, chromic acid, pyridinium chlorochromate, pyridinium dichromate, potassium permanganate, sulfur trioxide-pyridine, oxone, silver nitrate, silver oxide (I), silver oxide (II), sodium periodate, sodium perchlorate, hydrogen peroxide and the like, and these may be used in combination. Examples of the additive include acetic acid, sulfuric acid, sulfamic acid, ruthenium oxide, 2-methyl-2-butene, DMSO and the like.

Step 4

Compound (VIII) may be prepared by treating compound (VII) obtained in the Step 3 with catalytic amount to 10 equivalents of a suitable oxidizing agent in the presence of, if necessary, 1 to 10 equivalents of a suitable additive in an inert solvent at a temperature between 0° C. and 100° C. for 1 to 24 hours. Further, a plurality of oxidizing agents may be used in combination, if necessary.

Examples of the inert solvent include acetone, diethyl ether, THF, acetonitrile, ethyl acetate, acetic acid, propionic acid, butyric acid, trifluoroacetic acid, water, toluene, benzene, dichloromethane and the like, and these may be used in combination. Examples of the oxidizing agent include sodium periodate, hydrogen peroxide, peracetic acid, performic acid, pertrifluoroacetic acid, orthosulfoperbenzoic acid, peroxyphthalic acid, monoperoxysuccinic acid, disuccinoylperoxide, potassium permanganate, osmium tetroxide, a silver acetate-iodine complex, 4-methylmorpholine-N-oxide, trimethylamine-N-oxide, potassium ferricyanate and the like. Examples of the additive include 4-methylmorpholine, triethylamine, pyridine, ruthenium chloride, cerium chloride and the like.

Step 5

Compound (IX) may be prepared by reacting compound (VIII) obtained in the Step 4 with 1 to 10 equivalents of a suitable oxidizing agent in the presence of 1 to 10 equivalents of a suitable base in an inert solvent at a temperature between −78° C. and the boiling point of the solvent used for 5 minutes to 72 hours.

Examples of the oxidizing agent include lead tetraacetate, sodium periodate, chromic acid and the like. Examples of the inert solvent include dichloromethane, chloroform, carbon tetrachloride, 1,2-dichloroethane, toluene, ethyl acetate, acetonitrile, diethyl ether, THF, dimetoxy ethane (DME), dioxane, DMF, DMA, N-methyl pyrrolidone (NMP), DMSO and the like, and these may be used in combination. Examples of the base include pyridine, lutidine, triethylamine, diisopropylethylamine and the like.

Step 6

Compound (I-a) may be prepared by reacting compound (IX) obtained in the Step 5 with 1 equivalent to a large excess amount of suitable acid anhydride, acid halide or a halogenating agent in the presence of 1 equivalent to a large excess amount of a suitable base in an inert solvent at a temperature between −78° C. and the boiling point of the solvent used for 5 minutes to 72 hours.

Examples of the acid anhydride or acid halide include acetic anhydride, anhydrous propionic acid, acetyl chloride, propionyl chloride and the like, and examples of the halogenating agent include thionyl chloride, phosphorus oxychloride, oxalyl dichloride, methanesulfonyl chloride and the like. Examples of the inert solvent include dichloromethane, chloroform, carbon tetrachloride, 1,2-dichloroethane, toluene, ethyl acetate, acetonitrile, diethyl ether, THF, DME, dioxane, DMF, DMA, NMP, DMSO and the like, and these may be used in combination. Examples of the base include sodium acetate, sodium carbonate, sodium bicarbonate, potassium carbonate, sodium hydroxide, potassium hydroxide, pyridine, lutidine, triethylamine, diisopropylethylamine and the like.

Step 7

Compound (I-b) may be prepared by treating compound (I-a) obtained in the Step 6 with 1 to 10 equivalents of a suitable reducing agent in an inert solvent at a temperature between −78° C. and the boiling point of the solvent used for 5 minutes to 72 hours.

Examples of the reducing agent include lithium aluminium hydride, diisobutyl aluminium hydride, sodium borohydride, lithium borohydride, diisopropyl aluminium hydride, potassium tri(sec-butyl) borohydride and the like. Examples of the inert solvent include dichloromethane, chloroform, carbon tetrachloride, 1,2-dichloroethane, toluene, diethyl ether, THF, DME, dioxane, acetonitrile, methanol, ethanol, propanol, DMF, DMA, NMP, DMSO and the like, and these may be used in combination.

Preparation Method 2

Among compounds (I), compound (I-c) in the following scheme may be prepared, for example, according to the following steps.

[Chem. 6]

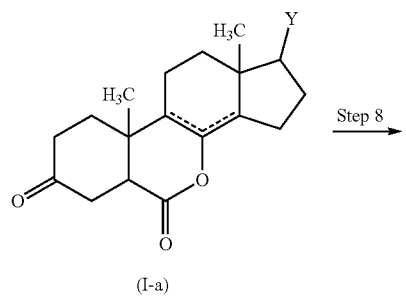
(I-a)

Step 8 →

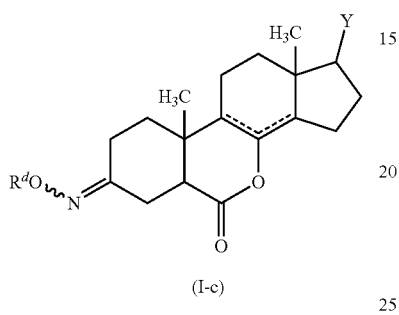
(I-c)

(wherein $R^d$ and Y have the same meanings as defined above, respectively)

Step 8

Compound (I-c) may be prepared by reacting compound (I-a) obtained in the Step 6 of Preparation Method 1 with 1 to 10 equivalents of $R^dONH_2$ in the presence of 1 equivalent to a large excess amount of a suitable base in an inert solvent at a temperature between 0° C. and the boiling point of the solvent used for 5 minutes to 72 hours.

Examples of the inert solvent include methanol, ethanol, propanol, dichloromethane, chloroform, carbon tetrachloride, 1,2-dichloroethane, toluene, ethyl acetate, acetonitrile, diethyl ether, THF, DME, dioxane, DMF, DMA, NMP, DMSO and the like, and these may be used in combination. Examples of the base include sodium acetate, sodium carbonate, sodium bicarbonate, potassium carbonate, sodium hydroxide, potassium hydroxide, pyridine, lutidine, triethylamine, diisopropylethylamine and the like.

Preparation Method 3

Among compounds (I), compounds (I-d) and (I-e) in the following scheme may be prepared, for example, according to the following steps.

[Chem. 7]

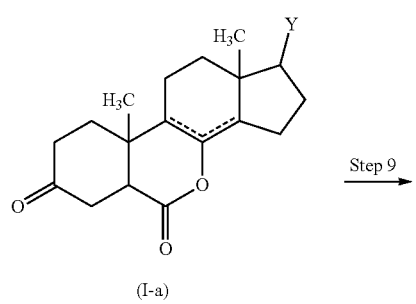
(I-a)

Step 9 →

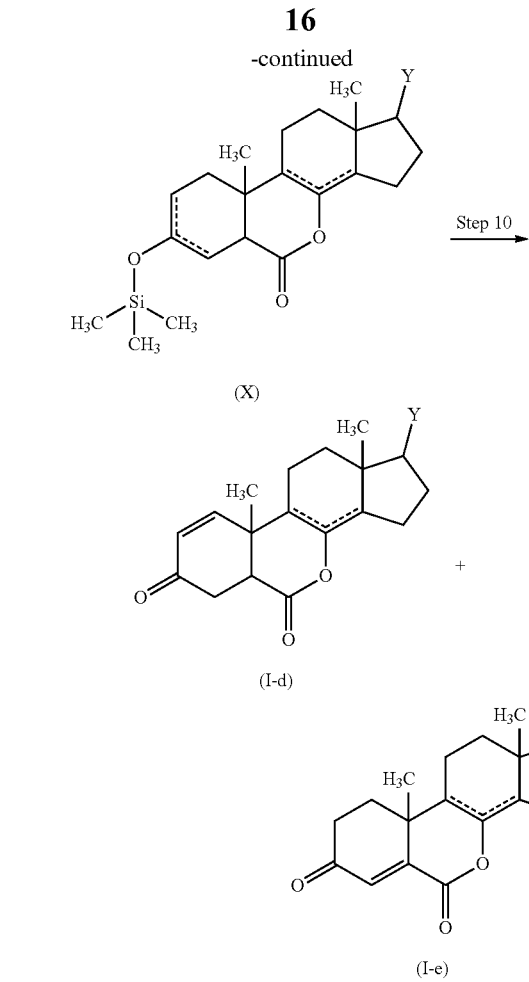

(wherein Y has the same meaning as defined above)

Step 9

Compound (X) may be prepared by reacting compound (I-a) obtained in the Step 6 of Preparation Method 1 with 1 to 10 equivalents of chlorotrimethylsilane in the presence of 1 to 10 equivalents of a suitable base in an inert solvent at a temperature between −78° C. and room temperature for 5 minutes to 24 hours.

Examples of the inert solvent include dichloromethane, toluene, diethyl ether, THF, DME, dioxane and the like, and these may be used in combination. Examples of the base include lithium diisopropyl amide (LDA), lithium hexamethyl disilazide (LHMDS), potassium hexamethyl disilazide (KHMDS), potassium tert-butoxide and the like.

Step 10

Compound (I-d) or (I-e) may be prepared by treating compound (X) obtained in the Step 9 in the presence of 1 to 10 equivalents of a palladium compound in an inert solvent at a temperature between −78° C. and room temperature for 5 minutes to 24 hours.

Examples of the palladium compound include palladium (II) acetate, bis(triphenylphosphine) palladium (II) chloride, [1,2-bis(diphenylphosphino)ethane]palladium (II) chloride, [1,1′-bis(diphenylphosphino)ferrocene]palladium (II) chloride and the like. Examples of the solvent include dichloromethane, chloroform, carbon tetrachloride, 1,2-dichloroethane, toluene, ethyl acetate, acetonitrile, diethyl ether, THF, DME, dioxane, DMF, DMA, NMP, DMSO and the like, and these may be used in combination.

Step 4

Among compounds (I), compound (I-f) in the following scheme may be prepared, for example, according to the following step.

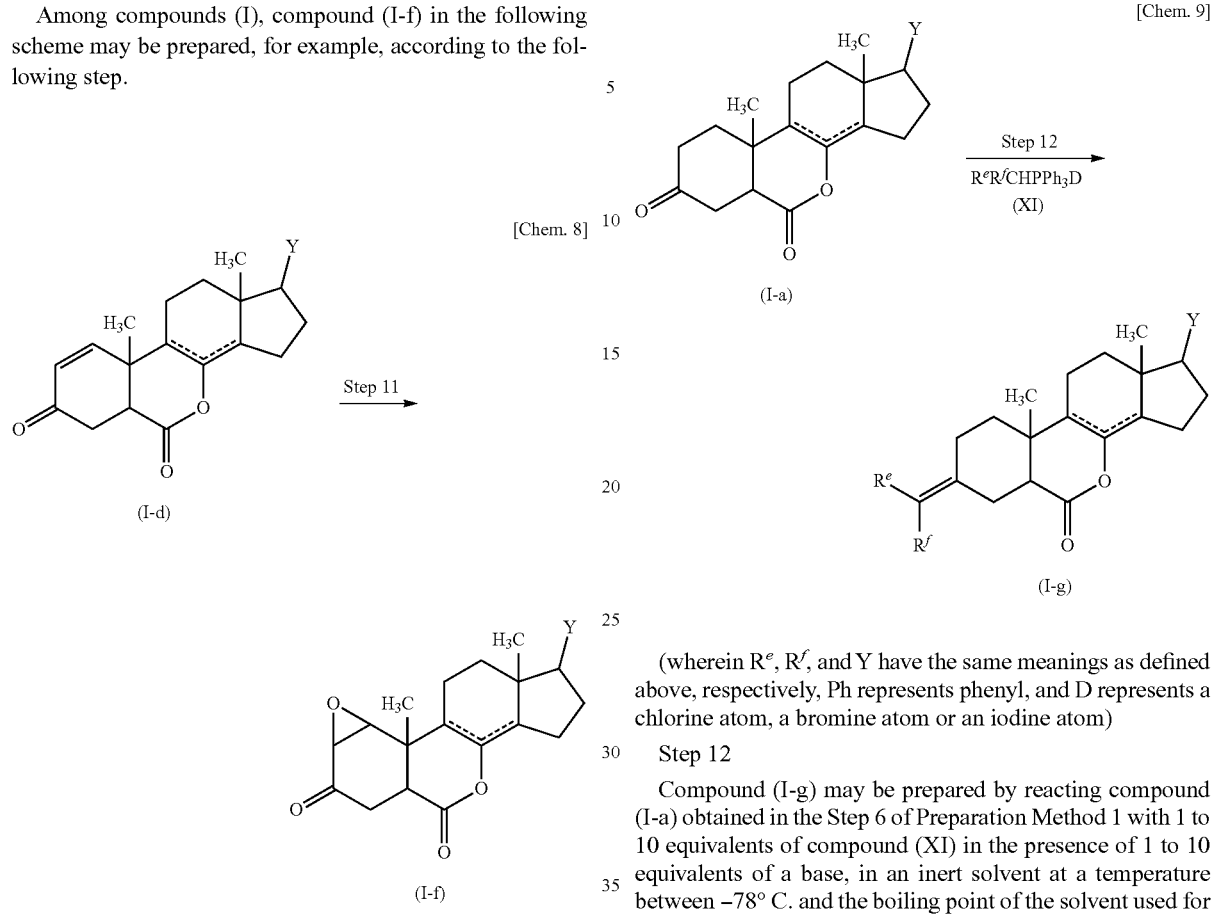

(wherein Y has the same meaning as defined above)

Process 11

Compound (I-f) may be prepared by reacting compound (I-d) obtained in the Step 10 of Preparation Method 3 with 1 to 10 equivalents of a suitable oxidizing agent in the presence of, if necessary, 1 equivalent to a large excess amount of a base in an inert solvent at a temperature between −78° C. and the boiling point of the solvent used for 5 minutes to 72 hours.

Examples of the oxidizing agent include hydrogen peroxide, tert-butylhydroperoxide (TBHP), peracetic acid, m-chloroperbenzoic acid, perbenzoic acid, trifluoroperacetic acid and the like. Examples of the inert solvent include dichloromethane, chloroform, carbon tetrachloride, 1,2-dichloroethane, toluene, diethyl ether, THF, DME, dioxane, acetonitrile, methanol, ethanol, propanol, tert-butanol, water, DMF, DMA, NMP, DMSO and the like, and these may be used in combination. Examples of the base include sodium acetate, sodium carbonate, sodium bicarbonate, potassium carbonate, sodium hydroxide, potassium hydroxide, pyridine, lutidine, triethylamine, diisopropylethylamine and the like.

Preparation Method 5

Among compounds (I), compound (I-g) in the following scheme may be prepared, for example, according to the following step.

(wherein $R^e$, $R^f$, and Y have the same meanings as defined above, respectively, Ph represents phenyl, and D represents a chlorine atom, a bromine atom or an iodine atom)

Step 12

Compound (I-g) may be prepared by reacting compound (I-a) obtained in the Step 6 of Preparation Method 1 with 1 to 10 equivalents of compound (XI) in the presence of 1 to 10 equivalents of a base, in an inert solvent at a temperature between −78° C. and the boiling point of the solvent used for 5 minutes to 72 hours.

Examples of the base include LDA, LHMDS, KHMDS, potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the inert solvent include dichloromethane, carbon tetrachloride, 1,2-dichloroethane, toluene, diethyl ether, THF, DME, dioxane, DMF, DMA, NMP and the like, and these may be used in combination. Compound (XI) may be obtained, for example, as a commercially available product.

Preparation Method 6

Among compounds (I), compound (I-h) in the following scheme may be prepared, for example, according to the following step.

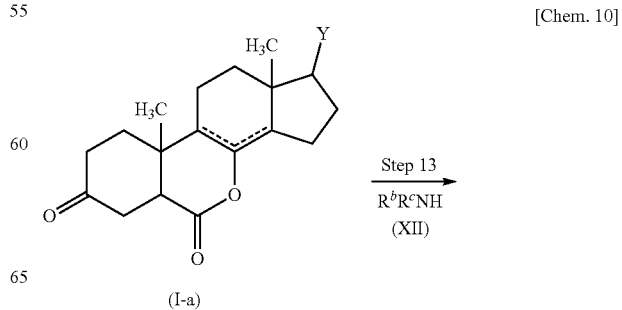

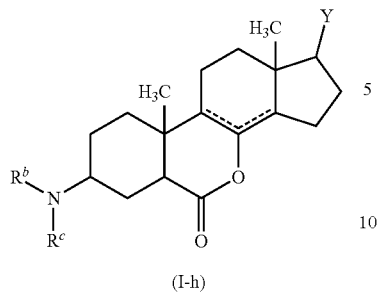

(I-h)

(wherein $R^b$, $R^c$ and Y have the same meanings as defined above, respectively)

Step 13

Compound (I-h) may be prepared by reacting compound (I-a) obtained in the Step 6 of Preparation Method 1 with 1 to 10 equivalents of compound (XII) in the presence of 1 to 10 equivalents of a reducing agent in an inert solvent at a temperature between −78° C. and the boiling point of the solvent used for 5 minutes to 72 hours.

Examples of the reducing agent include sodium borohydride, sodium triacetoxyborohydride, sodium cyanoborohydride and the like. Examples of the inert solvent include dichloromethane, carbon tetrachloride, 1,2-dichloroethane, toluene, diethyl ether, THF, DME, acetonitrile, dioxane, DMF, DMA, NMP, methanol, ethanol, propanol, acetic acid, propionic acid and the like, and these may be used in combination. Compound (XII) may be obtained, for example, as a commercially available product.

Preparation Method 7

Among compounds (I), compounds (I-i) and (I-j) in the following scheme may be prepared, for example, according to the following steps.

[Chem. 11]

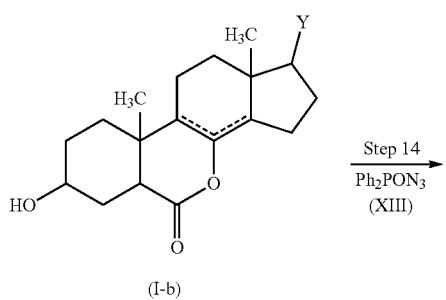

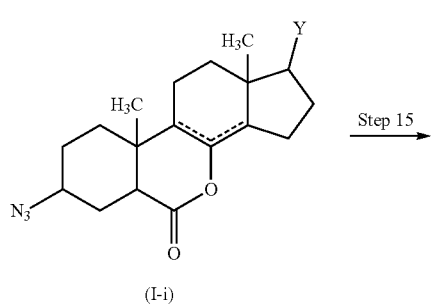

(I-i)

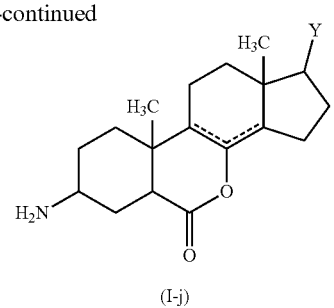

(I-j)

(wherein Ph represents phenyl and Y has the same meaning as defined above)

Step 14

Compound (I-i) may be prepared by reacting compound (I-b) obtained in the Step 7 of Preparation Method 1 with 1 to 10 equivalents of diphenyl phosphorazidate (compound (XIII)) in the presence of 1 to 10 equivalents of a suitable oxygen atom receptor or a hydrogen atom receptor in an inert solvent at a temperature between −78° C. and the boiling point of the solvent used for 5 minutes to 72 hours.

Examples of the oxygen atom receptor include triphenylphosphine, tributylphosphine and the like, and examples of the hydrogen atom receptor include diethyl azodicarboxylate (DEAD), di-tert-butylazodicarboxylate, N,N,N',N'-tetramethyl azadicarboxamide and the like. Examples of the inert solvent include dichloromethane, carbon tetrachloride, 1,2-dichloroethane, toluene, diethyl ether, THF, DME, acetonitrile, dioxane, DMF, DMA, NMP and the like, and these may be used in combination. Compound (XIII) may be obtained, for example, as a commercially available product.

Step 15

Compound (I-j) may be prepared by treating compound (I-i) obtained in the Step 14 with 1 to 10 equivalents of a suitable reducing agent in an inert solvent at a temperature between −78° C. and the boiling point of the solvent used for 5 minutes to 72 hours.

Examples of the reducing agent include lithium aluminium hydride, sodium borohydride, lithium borohydride, diisopropyl aluminium hydride, potassium tri-(sec-butyl) borohydride, triphenylphosphine, borane, tributyl tin hydride and the like. Examples of the solvent include dichloromethane, chloroform, carbon tetrachloride, 1,2-dichloroethane, toluene, diethyl ether, THF, DME, dioxane, acetonitrile, methanol, ethanol, propanol, DMF, DMA, NMP, DMSO, water and the like, and these may be used in combination.

Preparation Method 8

Among compounds (I), compound (I-k) in the following scheme may be prepared, for example, according to the following step.

[Chem. 12]

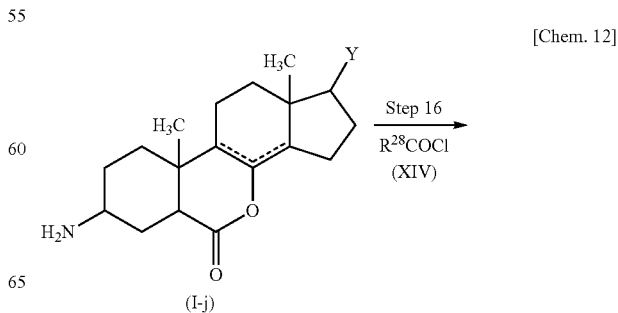

(I-j)

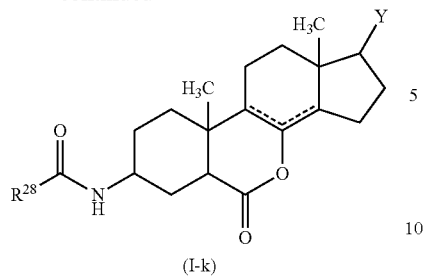

(I-k)

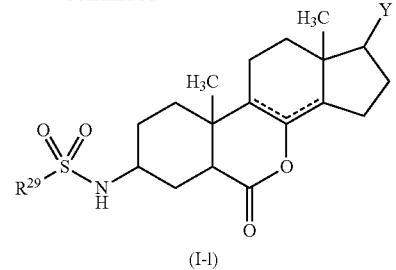

(I-l)

(wherein $R^{28}$ represents a moiety of optionally substituted lower alkyl, optionally substituted aryl, optionally substituted lower alkoxy, optionally substituted aryloxy or optionally substituted aromatic heterocyclyloxy in the optionally substituted lower alkanoyl, the optionally substituted aroyl, the optionally substituted lower alkoxycarbonyl, the optionally substituted aryloxycarbonyl and the optionally substituted aromatic heterocyclyloxycarbonyl in the definition of $R^b$ or $R^c$, respectively, and Y has the same meaning as defined above)

Step 16

Compound (I-k) may be prepared by reacting compound (I-j) obtained in the Step 15 of Preparation Method 7 with 1 to 10 equivalents of compound (XIV) in the presence of 1 equivalent to a large excess amount of a base in an inert solvent at a temperature between −78° C. and the boiling point of the solvent used for 5 minutes to 72 hours.

Examples of the base include potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the inert solvent include dichloromethane, carbon tetrachloride, 1,2-dichloroethane, toluene, diethyl ether, THF, DME, dioxane, DMF, DMA, NMP and the like, and these may be used in combination. Compound (XIV) may be obtained, for example, as a commercially available product.

Preparation Method 9

Among compounds (I), compound (I-l) in the following scheme may be prepared, for example, according to the following step.

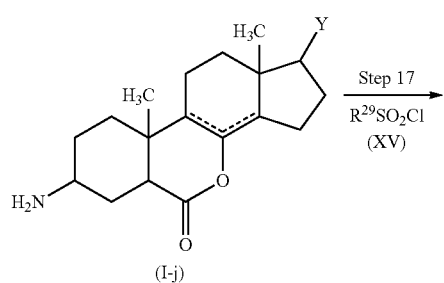

(I-j)

[Chem. 13]

Step 17
$R^{29}SO_2Cl$
(XV)

(wherein $R^{29}$ represents a moiety of optionally substituted aryl or optionally substituted lower alkyl in the optionally substituted arylsulfonyl or the optionally substituted lower alkylsulfonyl in the definition of $R^b$ or $R^c$, respectively, and Y has the same meaning as defined above)

Step 17

Compound (I-l) may be prepared by reacting compound (I-j) obtained in the Step 15 of Preparation Method 7 with 1 to 10 equivalents of compound (XV) in the presence of 1 equivalent to a large excess amount of a base in an inert solvent at a temperature between −78° C. and the boiling point of the solvent used for 5 minutes to 72 hours.

Examples of the base include potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the inert solvent include dichloromethane, carbon tetrachloride, 1,2-dichloroethane, toluene, diethyl ether, THF, DME, dioxane, DMF, DMA, NMP and the like, and these may be used in combination. Compound (XV) may be obtained, for example, as a commercially available product.

Preparation Method 10

Among compounds (I), compound (I-m) in the following scheme may be prepared, for example, according to the following step.

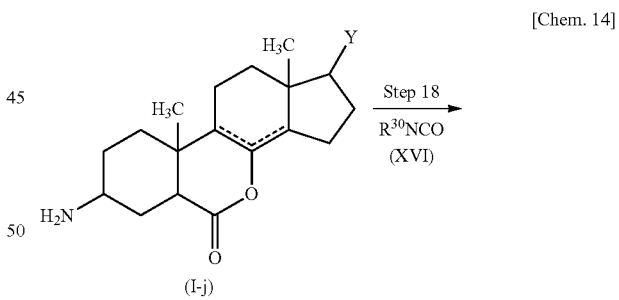

(I-j)

[Chem. 14]

Step 18
$R^{30}NCO$
(XVI)

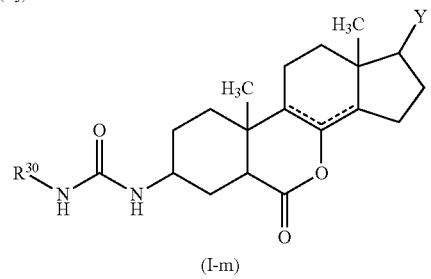

(I-m)

(wherein $R^{30}$ represents a moiety of optionally substituted lower alkyl, optionally substituted aryl, or an optionally substituted aromatic heterocyclic group in the optionally substituted lower alkylcarbamoyl, the optionally substituted arylcarbamoyl and the optionally substituted aromatic heterocyclylcarbamoyl in the definition of $R^b$ or $R^c$, respectively, and Y has the same meaning as defined above)

Process 18

Compound (I-m) may be prepared by reacting compound (I-j) obtained in the Step 15 of Preparation Method 7 with 1 to 10 equivalents of compound (XVI) in the presence of, if necessary, 1 equivalent to a large excess amount of a base, in an inert solvent at a temperature between −78° C. and the boiling point of the solvent used for 5 minutes to 72 hours.

Examples of the base include potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the inert solvent include dichloromethane, carbon tetrachloride, 1,2-dichloroethane, toluene, diethyl ether, THF, DME, dioxane, DMF, DMA, NMP and the like, and these may be used in combination. Compound (XVI) may be obtained, for example, as a commercially available product.

Preparation Method 11

Among compounds (I), compound (I-n) in the following scheme may be prepared, for example, according to such as the following step.

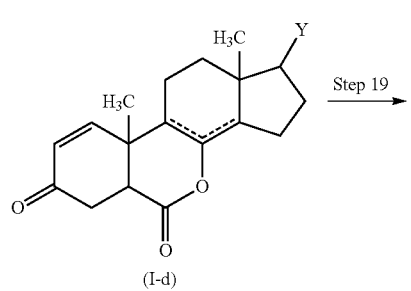

(wherein Y has the same meaning as defined above)

Step 19

Compound (I-n) may be prepared by reacting compound (I-d) obtained in the Step 10 of Preparation Method 3 with catalytic amount to 10 equivalents of a suitable oxidizing agent in the presence of, if necessary, 1 equivalent to a large excess amount of a co-oxidizing agent in an inert solvent at a temperature between −78° C. and the boiling point of the solvent used for 5 minutes to 72 hours.

Examples of the oxidizing agent include hydrogen peroxide, TBHP, peracetic acid, m-chloroperbenzoic acid, perbenzoic acid, trifluoroperacetic acid, potassium permanganate, osmium tetroxide and the like, and examples of the co-oxidizing agent include 4-methylmorpholine-N-oxide, trimethylamine-N-oxide and the like. Examples of the inert solvent include dichloromethane, chloroform, carbon tetrachloride, 1,2-dichloroethane, toluene, diethyl ether, THF, DME, dioxane, acetonitrile, methanol, ethanol, propanol, tert-butanol, water, DMF, DMA, NMP, DMSO and the like, and these may be used in combination.

Preparation Method 12

Among compounds (I), compound (I-o) in the following scheme may be prepared, for example, according to such as the following step.

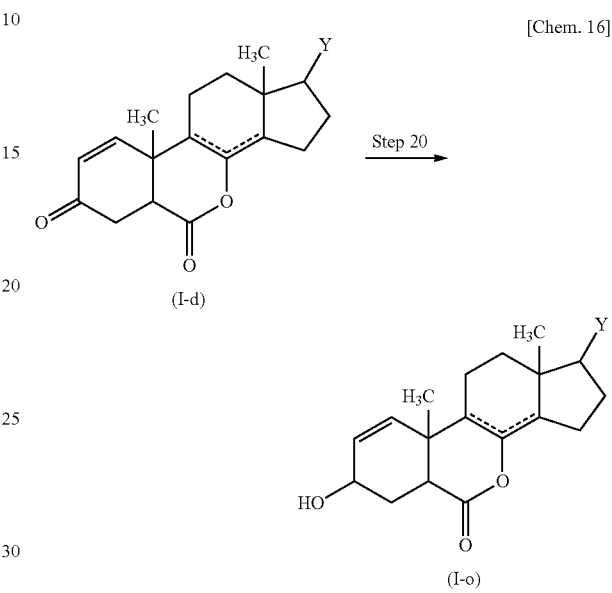

(wherein Y has the same meaning as defined above)

Step 20

Compound (I-o) may be prepared in the same manner as the Step 7 of Preparation Method 1 by using compound (I-d) obtained in the Step 10 of Preparation Method 3.

Preparation Method 13

Among compounds (I), compounds (I-p), (I-q) and (I-r) in the following scheme may be prepared, for example, according to the following step.

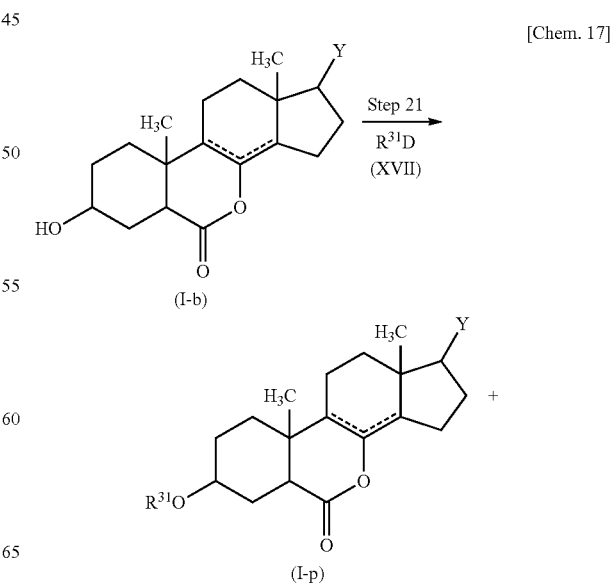

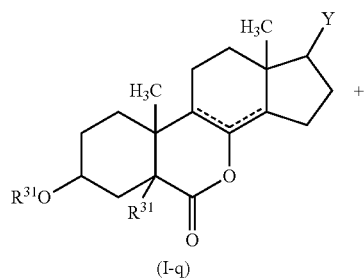

(I-q)

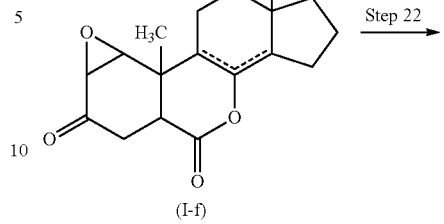

(I-f)

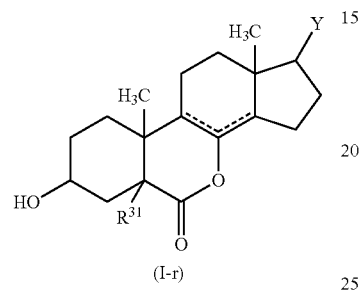

(I-r)

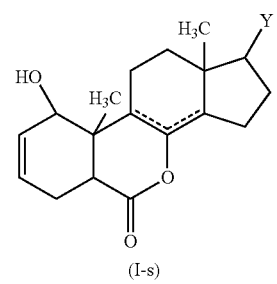

(I-s)

(wherein $R^{31}$ represents a moiety of optionally substituted lower alkyl, optionally substituted cycloalkyl, optionally substituted lower alkenyl, optionally substituted lower alkynyl, an optionally substituted aliphatic heterocyclic group, optionally substituted alkanoyl or optionally substituted aroyl in the optionally substituted lower alkoxy, the optionally substituted cycloalkyloxy, the optionally substituted lower alkenyloxy, the optionally substituted lower alkynyloxy, the optionally substituted aliphatic heterocyclyloxy, the optionally substituted alkanoylox, and the optionally substituted aroyloxy in the definition of $R^5$ or $R^6$, respectively, D represents a chlorine atom, a bromine atom or an iodine atom, and Y has the same meaning as defined above)

Step 21

Compounds (I-p), (I-q), and (I-r) may be prepared by reacting compound (I-b) obtained in the Step 7 of Preparation Method 1 with 1 to 10 equivalents of compound (XVII) in the presence of 1 to 10 equivalents of a base and, if necessary, a suitable additive in an inert solvent at a temperature between −78° C. and the boiling point of the solvent used for 5 minutes to 72 hours.

Examples of the base include sodium hydride, potassium iodide, LDA, LHMDS, KHMDS, potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the additive include silver oxide and the like. Examples of the inert solvent include dichloromethane, carbon tetrachloride, 1,2-dichloroethane, toluene, diethyl ether, THF, DME, dioxane, DMF, DMA, NMP and the like, and these may be used in combination. Compound (XVII) may be obtained, for example, as a commercially available product.

Preparation Method 14

Among compounds (I), compound (I-s) in the following scheme may be prepared, for example, according to such as the following step.

(wherein Y has the same meaning as defined above)

Step 22

Compound (I-s) may be prepared by treating compound (I-f) obtained in the Step 11 of Preparation Method 4 in the presence of 1 equivalent to a large excess amount of hydrazine and 1 equivalent to a large excess amount of a suitable acid in an inert solvent at a temperature between −78° C. and the boiling point of the solvent used for 5 minutes to 72 hours.

Examples of the acid include acetic acid, propionic acid, hydrochloric acid, sulfuric acid, nitric acid and the like. Examples of the solvent include methanol, ethanol, propanol, butanol, dichloromethane, carbon tetrachloride, 1,2-dichloroethane, toluene, diethyl ether, THF, DME, dioxane, DMF, DMA, NMP, DMSO, water and the like, and these may be used in combination.

Preparation Method 15

Among compounds (I), compound (I-ab) in the following scheme may be prepared, for example, according to such as the following step.

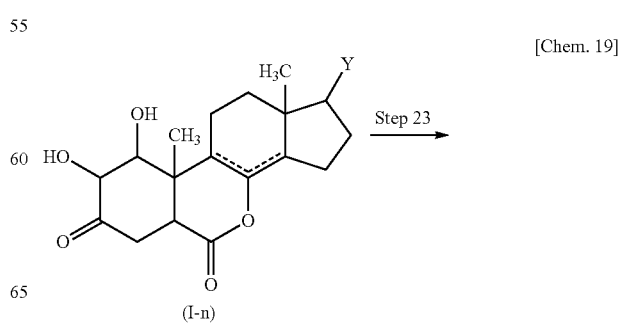

(I-n)

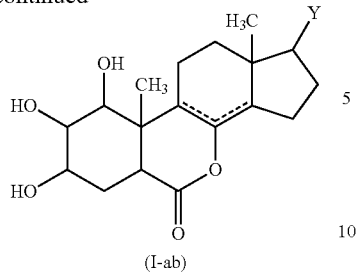

(I-ab)

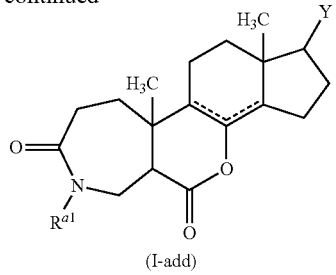

(I-add)

(wherein Y has the same meaning as defined above)

Step 23

Compound (I-ab) may be prepared in the same manner as the Step 7 of Preparation Method 1 by using compound (I-n) obtained in the Step 19 of Preparation Method 11.

Preparation Method 16

Among compounds (I), compounds (I-ac), (I-ad), (I-acc), and (I-add) in the following scheme may be prepared, for example, according to such as the following steps.

[Chem. 20]

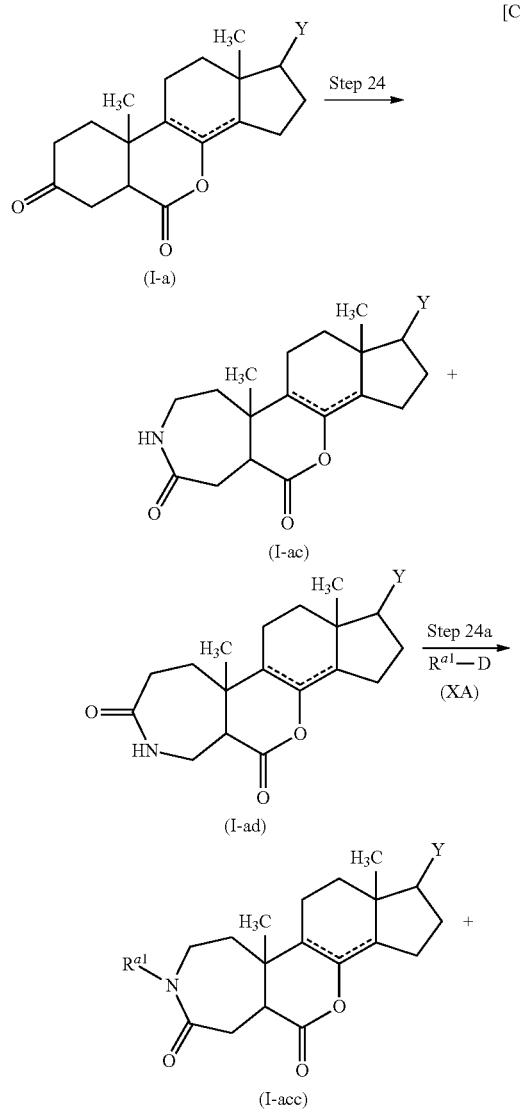

(wherein $R^{a1}$ represents optionally substituted lower alkyl, optionally substituted cycloalkyl, optionally substituted lower alkanoyl, or optionally substituted aroyl in the definition of $R^a$, respectively, D represents a chlorine atom, a bromine atom and an iodine atom, and Y has the same meaning as defined above)

Step 24

Compounds (I-ac) and (I-ad) may be prepared by treating compound (I-a) obtained in the Step 6 of Preparation Method 1 with 1 equivalent to a large excess amount of hydroxy amine in the presence of 1 equivalent to a large excess amount of a suitable acid, acid chloride or acid anhydride, and, if necessary, in the presence of a suitable base in an inert solvent at a temperature between 0° C. and the boiling point of the solvent used for 5 minutes to 72 hours.

Examples of the inert solvent include dioxane, acetonitrile, diethyl ether, THF, DME, DMF, DMA, NMP, DMSO, dichloromethane, chloroform, carbon tetrachloride, 1,2-dichloroethane, toluene and the like, and these may be used in combination. Examples of the acid include methanesulfonic acid, hydrochloric acid, phosphoric acid, sulfuric acid, nitric acid, formic acid, acetic acid, propionic acid and the like, examples of the acid chloride include thionyl chloride, phosphorus oxychloride, p-toluenesulfonyl chloride, methanesulfonyl chloride and the like, and examples of the acid anhydride include acetic anhydride, trifluoromethanesulfonic acid anhydride and the like. Examples of the base include sodium acetate, sodium carbonate, sodium bicarbonate, potassium carbonate, sodium hydroxide, potassium hydroxide, pyridine, lutidine, triethylamine, diisopropylethylamine, 4-dimethylaminopyridine and the like.

Step 24a

Compound (I-acc) or (I-add) may be prepared by reacting compound (I-ac) or (1-ad) obtained in the Step 24 with 1 to 30 equivalents of compound (XA) in the presence of 1 equivalent to a large excess amount of a suitable base in an inert solvent at a temperature between −78° C. and the boiling point of the solvent used for 5 minutes to 72 hours.

Examples of the inert solvent include dioxane, acetonitrile, diethyl etherTHF, DME, DMF, DMA, NMP, DMSO, dichloromethane, chloroform, carbon tetrachloride, 1,2-dichloroethane, toluene and the like, and these may be used in combination. Examples of the base include potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like.

Preparation Method 17

Among compounds (I), compound (I-ae) in the following scheme may be prepared, for example, according to the following step.

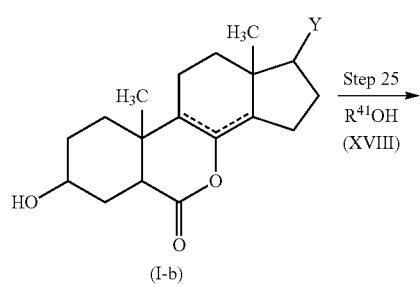

(I-b)

[Chem. 21]

Step 25
R⁴¹OH
(XVIII)

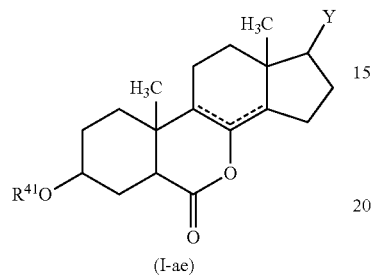

(I-ae)

(wherein R⁴¹ represents a moiety of optionally substituted ary or an optionally substituted aromatic heterocyclic group in optionally substituted aryloxy and optionally substituted aromatic heterocyclyloxy in the definition of $R^b$ or $R^c$, respectively, and Y has the same meaning as defined above)

Step 25

Compound (I-ae) may be prepared by reacting compound (I-b) obtained in the Step 7 of Preparation Method 1 with 1 to 10 equivalents of compound (XVIII) in the presence of 1 to 10 equivalents of a suitable oxygen atom receptor and a hydrogen atom receptor in an inert solvent at a temperature between −78° C. and the boiling point of the solvent used for 5 minutes to 72 hours.

Examples of the oxygen atom receptor include triphenylphosphine, tributylphosphine and the like, and examples of the hydrogen atom receptor include DEAD, di-tert-butylazodicarboxylate, N,N,N',N'-tetramethyl azadicarboxamide and the like. Examples of the inert solvent include dichloromethane, carbon tetrachloride, 1,2-dichloroethane, toluene, diethyl ether, THF, DME, acetonitrile, dioxane, DMF, DMA, NMP and the like, and these may be used in combination. Compound (XVIII) may be obtained, for example, as a commercially available product.

Preparation Method 18

Among compounds (I), compounds (1-af) and (I-ag) in the following scheme may be prepared, for example, according to the following step.

[Chem. 22]

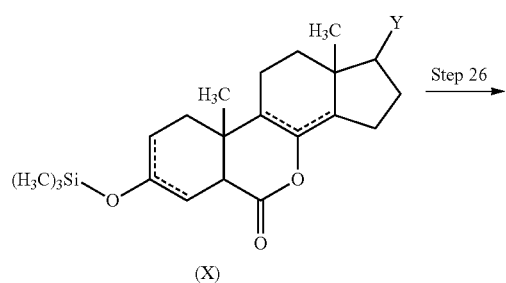

(X)

Step 26

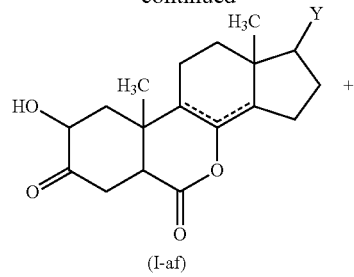

(I-af)

+

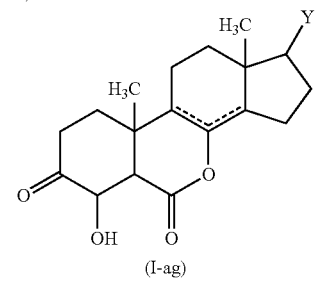

(I-ag)

(wherein Y has the same meaning as defined above)

Step 26

Compounds (1-af) and (I-ag) may be prepared in the same manner as the Step 4 of Preparation 1 or the Step 11 of Preparation Method 4 by using compound (X) obtained in the Step 9 of Preparation Method 3.

Preparation Method 19

Among compounds (I), compound (I-ah) in the following scheme may be prepared, for example, according to the following step.

[Chem. 23]

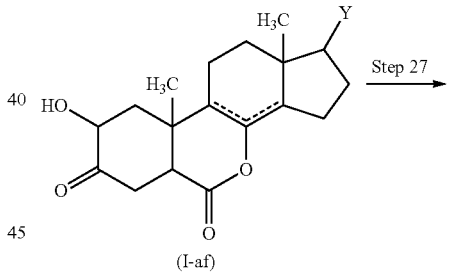

(I-af)

Step 27

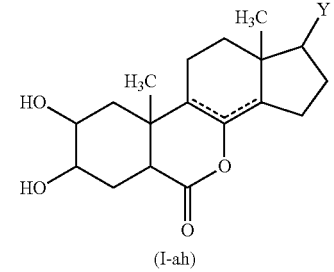

(I-ah)

(wherein Y has the same meaning as defined above)

Step 27

Compound (I-ah) may be prepared in the same manner as the Step 7 of Preparation Method 1 by using compound (I-af) obtained in the Step 26 of Preparation Method 18.

Preparation Method 20

Among compounds (I), compound (I-al) in the following scheme may be prepared, for example, according to the following step.

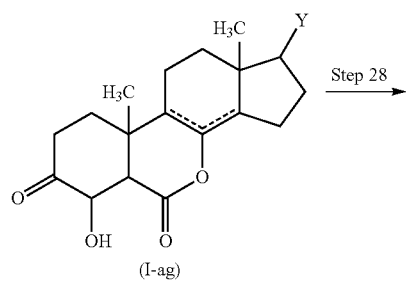

(I-ag)

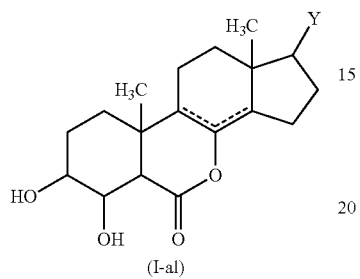

(I-al)

(wherein Y has the same meaning as defined above)

Step 28

Compound (I-al) may be prepared in the same manner as the Step 7 of Preparation Method 1 by using compound (I-ag) obtained in the Step 26 of Preparation Method 18.

Preparation Method 21

Among compounds (I), compound (I-am) in the following scheme may be prepared, for example, according to the following step.

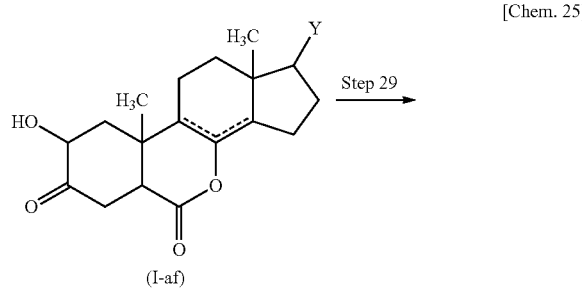

(I-af)

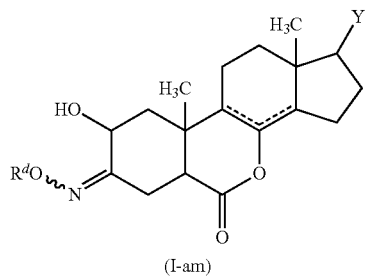

(I-am)

(wherein $R^d$ and Y have the same meanings as defined above, respectively)

Step 29

Compound (I-am) may be prepared in the same manner as the Step 8 of Preparation Method 2 by using compound (I-af) obtained in the Step 26 of Preparation Method 18.

Preparation Method 22

Among compounds (I), compound (I-an) in the following scheme may be prepared, for example, according to the following step.

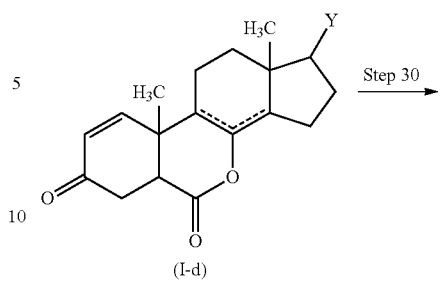

(I-d)

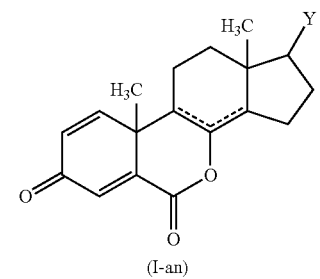

(I-an)

(wherein Y has the same meaning as defined above)

Step 30

Compound (I-an) may be prepared by treating compound (I-d) obtained in the Step 10 of Preparation Method 3 with 1 equivalent to a large excess amount of a base in the presence of 1 to 10 equivalents of a fluorinating agent in an inert solvent at a temperature between −78° C. and the boiling point of the solvent used for 5 minutes to 72 hours.

Examples of the base include sodium hydride, potassium iodide, LDA, LHMDS, KHMDS, potassium tert-butoxide, sodium acetate, sodium carbonate, sodium bicarbonate, potassium carbonate, sodium hydroxide, potassium hydroxide, pyridine, lutidine, triethylamine, diisopropylethylamine and the like. Examples of the fluorinating agent include fluorine gas, N-fluorobenzenesulfonimide, N,N'-difluoro-2,2'-bipyridinium bistetrafluoroborate, 1-chloromethyl-4-fluoro-1,4-diazo[2.2.2]octanebisammonate, cesium fluorosulfate, diethylaminosulfur trifluoride (DAST) and the like. Examples of the inert solvent include dichloromethane, carbon tetrachloride, 1,2-dichloroethane, toluene, diethyl ether, THF, DME, dioxane, DMF, DMA, NMP and the like, and these may be used in combination.

Preparation Method 23

Among compounds (I), compound (I-aq) in the following scheme may be prepared, for example, according to the following step.

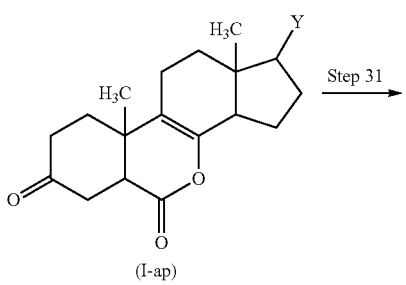

(I-ap)

-continued

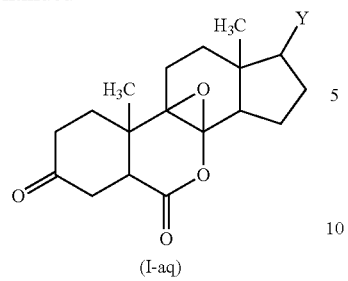

(I-aq)

(wherein Y has the same meaning as defined above)

Step 31

Compound (I-aq) may be prepared in the same manner as the Step 11 of Preparation Method 4 by using compound (I-ap) obtained in the Step 6 of Preparation Method 1.

Preparation Method 24

Compound (XXIV) of the following scheme may be prepared, for example, according to the following steps.

[Chem. 28]

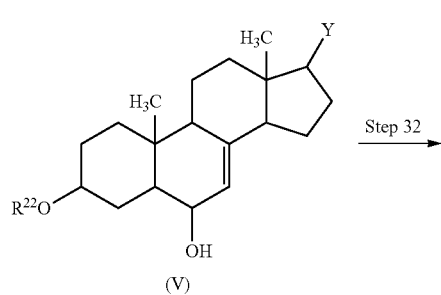

(V)

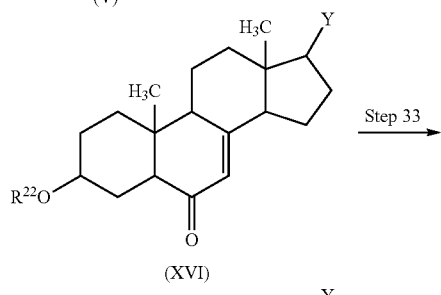

(XVI)

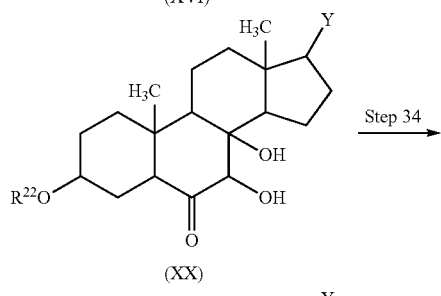

(XX)

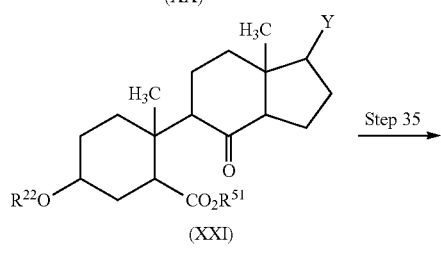

(XXI)

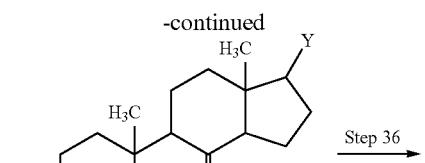

(XXII)

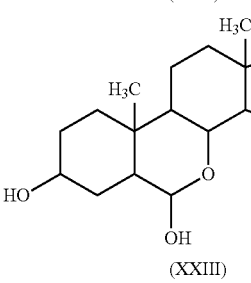

(XXIII)

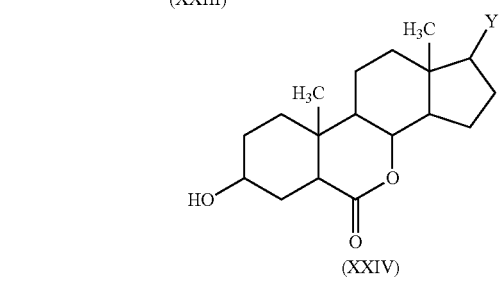

(XXIV)

(wherein $R^{51}$ represents $C_{1-10}$ alkyl, and $R^{22}$ and Y have the same meanings as defined above, respectively)

Step 32

Compound (XVI) may be prepared in the same manner as the Step 3 of Preparation Method 1 by using compound (V) obtained in the Step 1 of Preparation Method 1.

Step 33

Compound (XX) may be prepared in the same manner as the Step 4 of Preparation Method 1 by using compound (XVI) obtained in the Step 32.

Step 34

Compound (XXI) may be prepared in the same manner as the Step 5 of Preparation Method 1 by using compound (XX) obtained in the Step 33 in the presence of 1 equivalent to a large excess amount of $R^{51}OH$.

Step 35

Compound (XXII) may be prepared in the same manner as the Step 2 of Preparation Method 1 by using compound (XXI) obtained in the Step 34.

Step 36

Compound (XXIII) may be prepared in the same manner as the Step 7 of Preparation Method 1 by using compound (XXII) obtained in the Step 35.

Step 37

Compound (XXIV) may be prepared in the same manner as the Step 3 of Preparation Method 1 by using compound (XXIII) obtained in the Step 36.

The functional groups contained in $R^1$ to $R^{12}$, $R^a$ to $R^f$, $X^a$, $X^b$ and Z in compound (1) may be converted by a known method (for example, the method described in *Comprehensive Organic Transformations* 2nd edition, R. C. Larock, Vch Verlagsgesellschaft Mbh (1999) and the like) or methods similar thereto.

The intermediates and the desired compounds obtained in each of the above-mentioned preparation methods may be isolated and purified by applying separation purification methods usually used in the synthetic organic chemistry, such as filtration, extraction, washing, drying, concentration, recrystallization, various chromatographies or the like. Further, intermediates may also be subjected to a next reaction without particular purification.

Although some of compounds (I) may contain a geometric isomer, a stereoisomer such as an optical isomer, a tautomer, and the like, the present invention includes all possible isomers and mixtures thereof including these.

When a salt of compound (I) is intended to be obtained, compound (I) obtained in the form of a salt may be directly purified. When it is obtained in a free form, compound (I) may be dissolved or suspended in a suitable solvent, and an acid or base is added thereto to form a salt, which may be isolated and purified.

Further, while compound (I) and pharmaceutically acceptable salts thereof may exist in the form of adducts with water or various solvents, these adducts are also included in the present invention.

Specific examples of compound (I) obtained by the present invention are shown in Table 1 to Table 12. However, compound of the present invention is not limited thereto.

TABLE 1

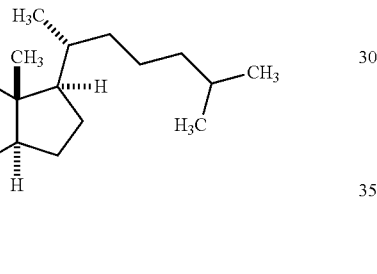

| Compound No. | A |
|---|---|
| 1 | 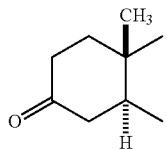 |
| 2 | 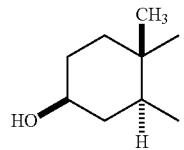 |
| 3 | 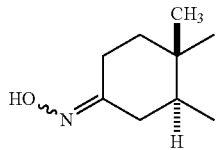 |
| 4 | 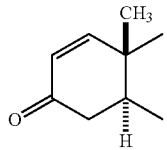 |

TABLE 1-continued

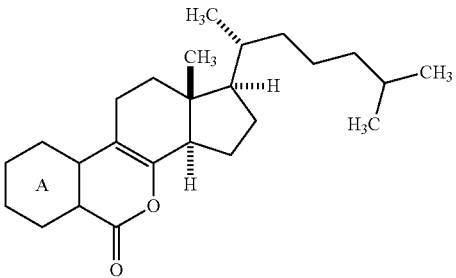

| Compound No. | A |
|---|---|
| 5 | 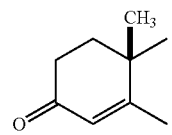 |
| 6 | 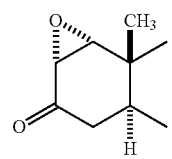 |
| 7 | 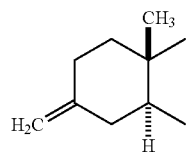 |
| 8 | 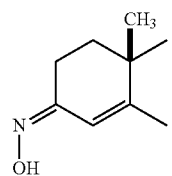 |
| 9 | 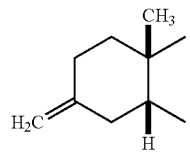 |
| 10 | 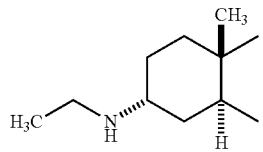 |
| 11 | 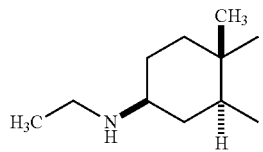 |
| 12 | 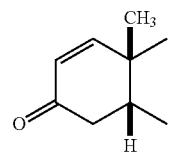 |

TABLE 2

| Compound No. | A |
|---|---|
| 13 | 4-amino-1,1,2-trimethylcyclohexyl (H₂N-, CH₃, CH₃, CH₃, H) |
| 14 | N-(1,1,2-trimethylcyclohexan-4-yl)methanesulfonamide |
| 15 | N-phenyl-N'-(1,1,2-trimethylcyclohexan-4-yl)urea |
| 16 | N-(1,1,2-trimethylcyclohexan-4-yl)benzamide |
| 17 | N-(1,1,2-trimethylcyclohexan-4-yl)acetamide |
| 18 | 2,3-dihydroxy-3,4-dimethyl-cyclohexan-1-one |
| 19 | 4-hydroxy-1,1,6-trimethylcyclohex-2-ene |

TABLE 2-continued

| Compound No. | A |
|---|---|
| 20 | 4-hydroxy-1,1,2,2-tetramethylcyclohexane... (HO-, CH₃, CH₃, CH₃, CH₃) |
| 21 | 1-hydroxy-6,6,5-trimethylcyclohex-2-ene |
| 22 | 4-methoxy-1,1,2,2-tetramethylcyclohexane |
| 23 | 4-methoxy-1,1,2,2-tetramethylcyclohexane |
| 24 | 4-hydroxy-1,1,2-trimethyl-2-vinylcyclohexane |

TABLE 3
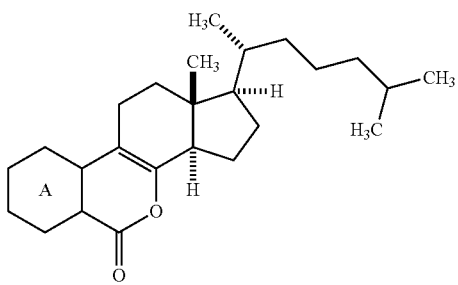
| Compound No. | A |
|---|---|
| 25 | 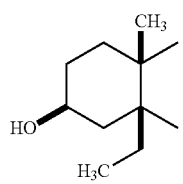 |
| 26 | 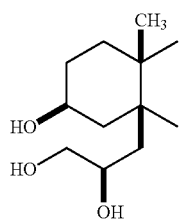 |
| 27 | 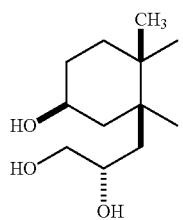 |
| 28 | 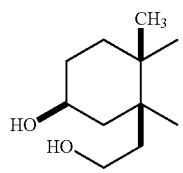 |
| 29 | 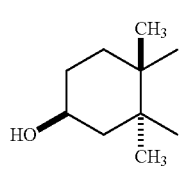 |
| 30 | 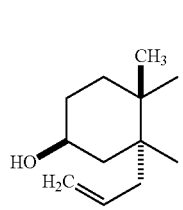 |
TABLE 3-continued
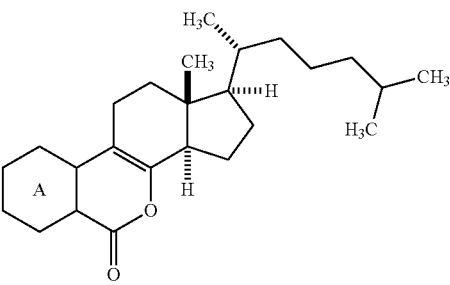
| Compound No. | A |
|---|---|
| 31 | 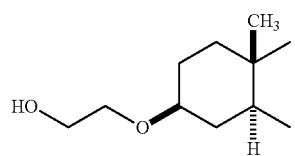 |
| 32 | 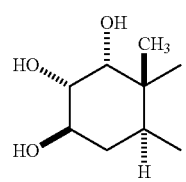 |
| 33 | 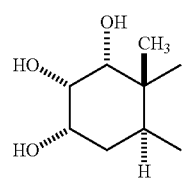 |
| 34 | 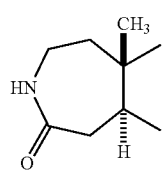 |
| 35 | 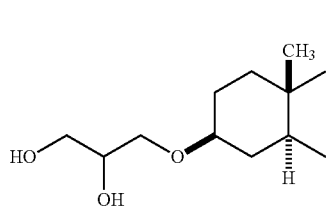 |
| 36 | 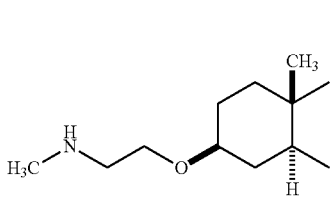 |

TABLE 4
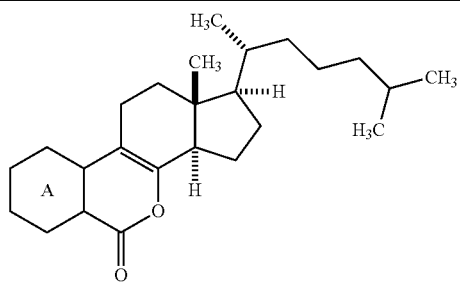
| Compound No. | A |
|---|---|
| 37 | 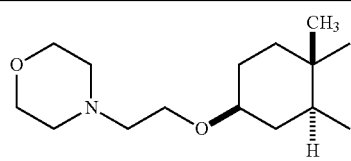 |
| 38 | 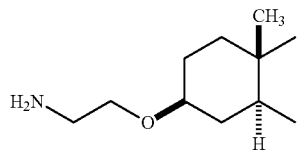 |
| 39 | 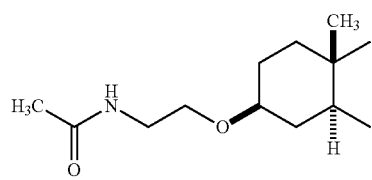 |
| 40 | 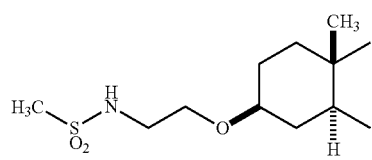 |
| 41 | 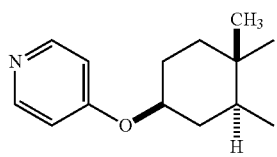 |
| 42 | 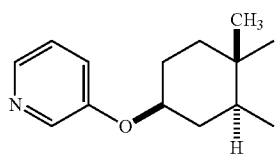 |
| 43 | 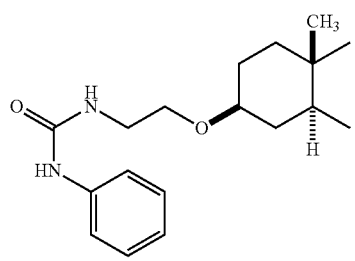 |
TABLE 4-continued
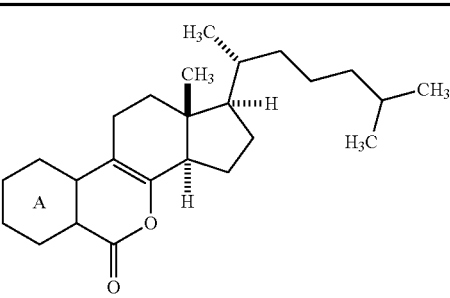
| Compound No. | A |
|---|---|
| 44 | 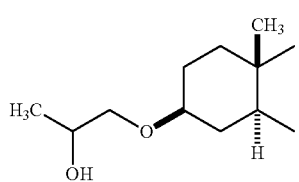 |
| 45 | 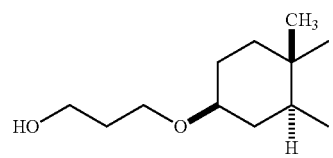 |
| 46 | 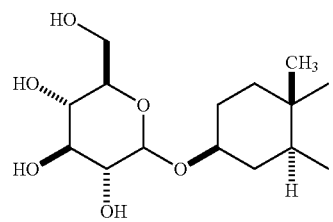 |
| 47 | 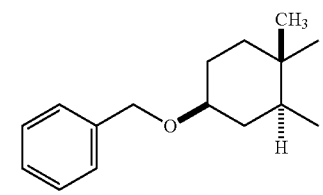 |
| 48 | 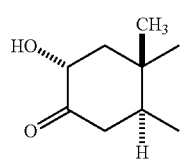 |

TABLE 5
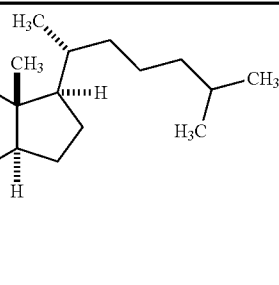
| Compound No. | A |
|---|---|
| 49 | 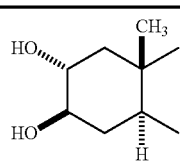 |
| 50 | 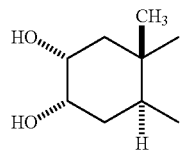 |
| 51 | 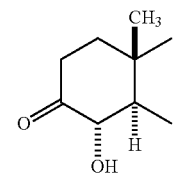 |
| 52 | 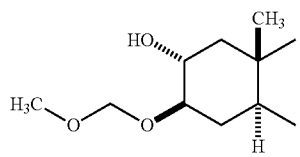 |
| 53 | 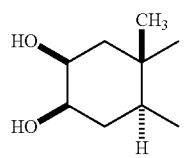 |
| 54 | 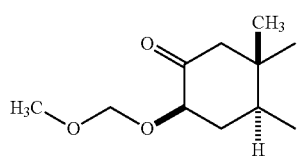 |
| 55 | 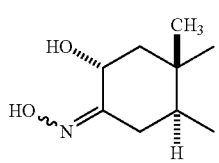 |
| 56 | 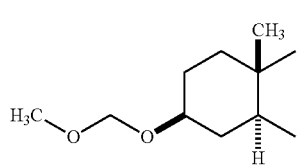 |
TABLE 5-continued
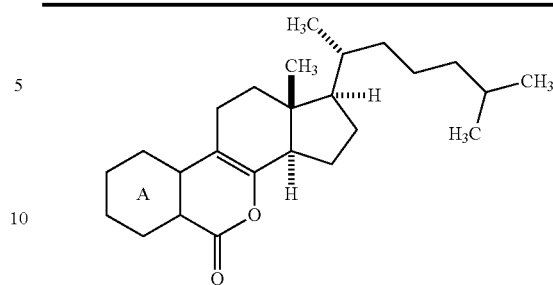
| Compound No. | A |
|---|---|
| 57 | 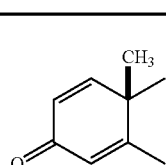 |
TABLE 6
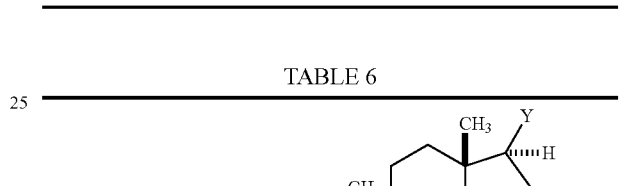
| Compound No. | Y |
|---|---|
| 58 | 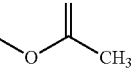 |
| 60 | 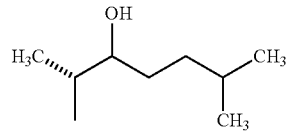 |
| 61 | 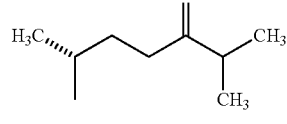 |
| 62 | 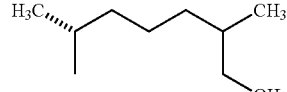 |
| 63 | 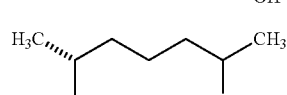 |
| 64 | 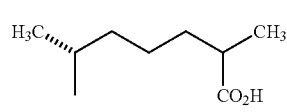 |

TABLE 6-continued

[Steroid lactone structure with MOM-protected 3β-OH and Y substituent at C17]

| Compound No. | Y |
|---|---|
| 65 | H₃C–CH(CH₃)–CH₂–O–CH₂–CH(CH₃)–CH₃ |
| 66 | H₃C–CH(CH₃)–CH₂–O–CH₂–CH=CH₂ |
| 67 | H₃C–CH(CH₃)–CH₂–O–CH₃ |
| 95 | H₃C–CH(CH₃)–CH₂–OH |
| 111 | H₃C–CH(CH₃)–CHO |

TABLE 7

[Steroid lactone structure with MOM-protected 3β-OH, Δ8,14-unsaturation, and Y substituent at C17]

| Compound No. | Y |
|---|---|
| 68 | H₃C–CH(CH₃)–CH₂–O–CH₂–CH₂–CH₃ |
| 69 | H₃C–CH(CH₃)–CH₂–NH–CH(CH₃)–CH₃ |
| 70 | H₃C–CH(CH₃)–CH₂–O–CH₂–CH(CH₃)–CH₂OH |
| 71 | H₃C–CH(CH₃)–CH₂–O–CH₂–CH(CH₃)–CH₂–OMe |

TABLE 7-continued

[Steroid lactone structure with MOM-protected 3β-OH, Δ8,14-unsaturation, and Y substituent at C17]

| Compound No. | Y |
|---|---|
| 72 | H₃C–CH(CH₃)–CH₂–N(morpholine) |
| 73 | H₃C–CH(CH₃)–(CH₂)₅–CH₂–O–C(O)–CH₃ |
| 74 | H₃C–CH(CH₃)–(CH₂)₅–CH₂–OH |
| 75 | H₃C–CH(CH₃)–(CH₂)₅–CH₂–NH–C(O)–O–C(CH₃)₃ |
| 96 | H₃C–CH(CH₃)–CH₂–O–CH₂–C(CH₃)=CH₂ |
| 98 | H₃C–CH(CH₃)–(CH₂)₅–CH₂–N₃ |

TABLE 8

[Steroid lactone structure with 3β-OH, Δ8,14-unsaturation, and Y substituent at C17]

| Compound No. | Y |
|---|---|
| 76 | H₃C–CH(CH₃)–CH₂–CH(CH₃)–CH₂–CH(CH₃)–CH₃ |
| 77 | H₃C–CH(CH₃)–CH₂–O–C(O)–CH₃ |

TABLE 8-continued

| Compound No. | Y |
|---|---|
| 78 | (2-methyl-6-oxoheptyl with methyl branch) |
| 79 | (2-methyl-6-methylheptyl with OH) |
| 80 | (2-methyl-6-methylheptyl with CO₂H) |
| 81 | (ether-linked isopropyl group) |
| 82 | (methoxymethyl branched) |
| 83 | (isobutylamino branched) |
| 97 | (acetate ester long chain) |

TABLE 9

| Compound No. | Y |
|---|---|
| 87 | (tert-butyl ester of methyl propanoate) |
| 88 | (2-methylpropanoic acid) |
| 89 | (amide-carbamate Boc-protected ethylenediamine) |
| 90 | (2,6-dimethylheptanol) |

TABLE 10

| Compound No. |
|---|
| 59 |

TABLE 10-continued
Compound No.
91
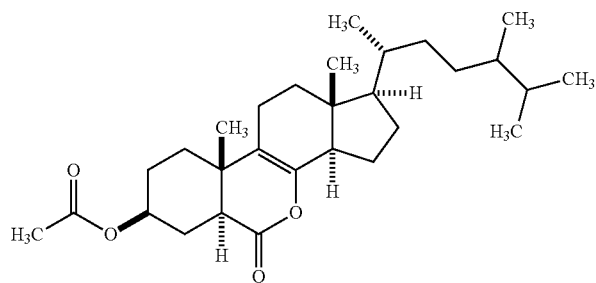
92
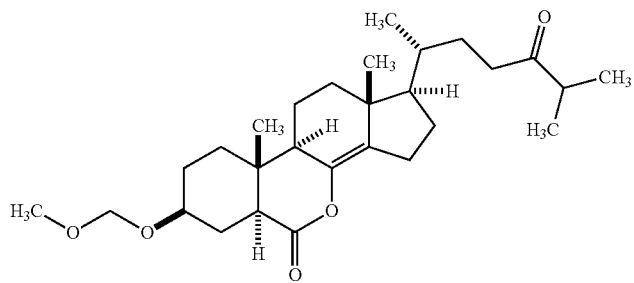
93
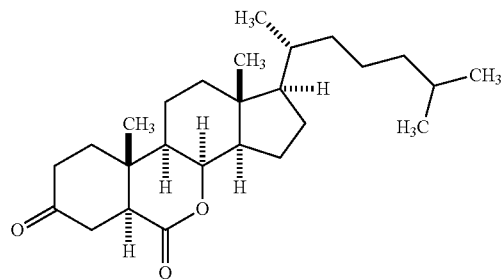
94
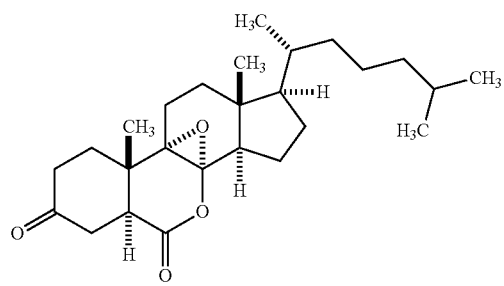 [SMILES: CC(C)CCC[C@@H](C)[C@H]1CC[C@@H]2[C@]1(C)CC[C@@]13O[C@@]21OC(=O)[C@H]1CC(=O)CC[C@@]13C]

TABLE 11
| Compound No. | |
|---|---|
| 99 | 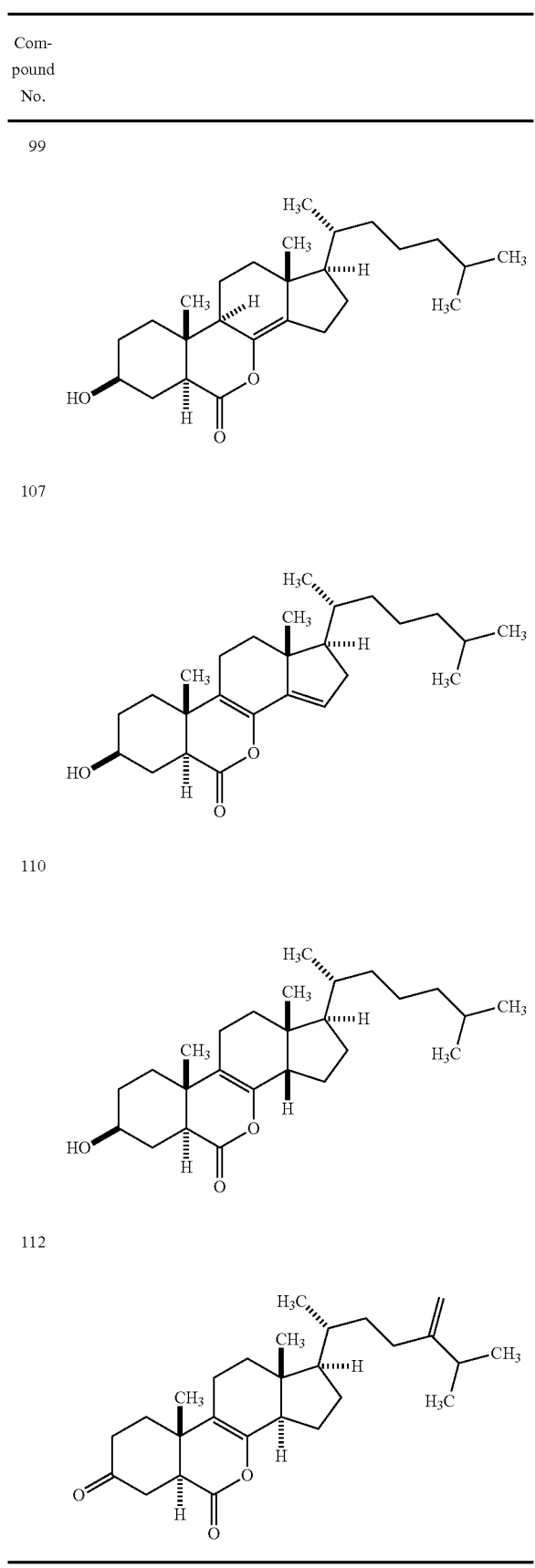 |
| 107 | |
| 110 | |
| 112 | |
TABLE 12
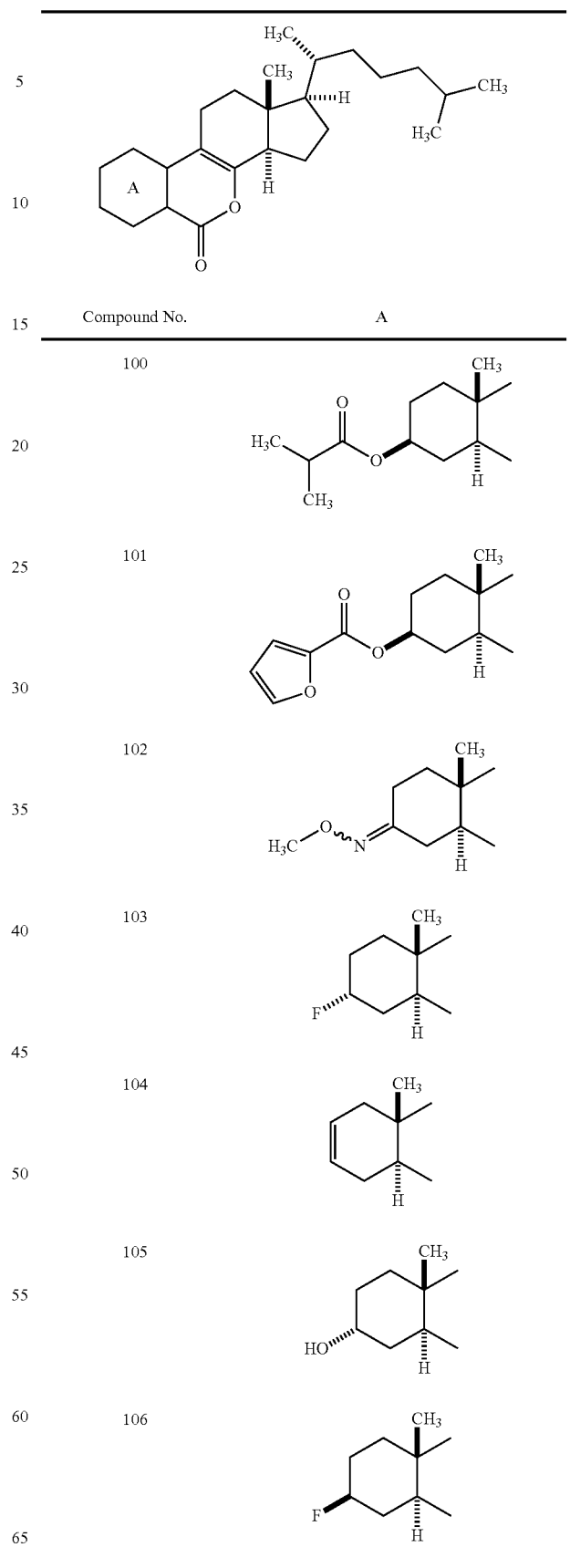
| Compound No. | A |
|---|---|
| 100 | |
| 101 | |
| 102 | |
| 103 | |
| 104 | |
| 105 | |
| 106 | |

TABLE 12-continued

| Compound No. | A |
|---|---|
| 108 | (structure) |
| 109 | (structure) |

When the compound of the present invention is allowed to contact with neural stem cells in vitro, it can promote proliferation of the neural stem cells.

The stem cell is a cell having a pluripotency which is an ability to differentiate into a variety of cells and an ability to self-renew of new stem cells by symmetric or asymmetric division. On the other hand, a cell which enters a certain lineage and is destined to carry through its differentiation after a limited division is called progenitor cells. However, since it is difficult to strictly distinguish neural stem cells and neural progenitor cells or glial progenitor cells, neural stem cells referred as in the present invention include neural progenitor cells and glial progenitor cells.

The neural stem cell includes preferably cerebral adult neural stem cells, but is not limited to.

The brain may include the brain of any animals, preferably the brain of a mammal, more preferably that of rat, mouse, monkey, human or the like.

Examples of the method for preparing adult neural stem cells from an animal include a method in which a cerebral cell crude extract is prepared by extracting the brain from an adult animal by a surgical means and the adult stem cells are concentrated from the crude extract, in accordance with the methods described, for example, in *The Journal of Neuroscience*, 1999, vol. 19, p. 8487-8497, *Genes and Development*, 1996, vol. 10, p. 3129-3140, and the like.

Also, examples of the method for preparing adult neural stems cells from human include a method in which a cerebral cell crude extract is prepared by collecting a tissue from the lateral ventricle wall of a patient of neurological disorder by biopsy and the adult stem cells are concentrated from the crude extract, in accordance with the method described in *Experimental Cell Research*, 2003, vol. 289, p. 378-383.

The compound of the present invention can be used in a method for producing neural stem cells comprising contacting the compound of the present invention with the neural stem cells in vitro, promoting the proliferation of neural stem cells by culturing, and collecting the neural stem cells from the culture.

When the compound of the present invention is used in vitro, it is preferable to use the compound of the present invention or a pharmaceutically acceptable salt thereof, by dissolving it in a solution which can dissolve the compound or a pharmaceutically acceptable salt thereof. Examples of the solution include water, dimethyl sulfoxide (DMSO) and the like. Also, it can be used by dissolving in various buffers such as phosphate buffered saline (PBS).

When adult neural stem cells are cultured in the presence of the compound of the present invention, it is preferable to add the compound at a concentration of 1 pmol/L to 1 mmol/L for approximately $6.25 \times 10^4$ cells/cm$^2$ of the adult neural stem cells. Proliferation of neural stem cells can be promoted by allowing adult neural stem cells to contact with the compound of the present invention, followed by static culturing at 37° C. for 1 to 14 days under an atmosphere of 5% $CO_2$ while exchanging the whole volume or a partial volume of the medium at intervals of 2 days.

The medium may be any medium as long as it is a medium which does not obstruct proliferation promotion of neural stem cells. For example, it is preferable to use DMEM/F12 medium (manufactured by Invitrogen) containing 1% N-2 additives (manufactured by Invitrogen), and the like.

Additionally, the neural stem cells prepared by the above-mentioned culturing can be differentiated into neurons, by carrying out static culturing at 37° C. for 1 to 14 days under an atmosphere of 5% $CO_2$, while exchanging the whole volume or a partial volume of a medium at intervals of 2 days, in a medium which does not contain the compound of the present invention but contains, for example, 1 nmol/L to 1 mmol/L of all-trans retinoic acid, 1 nmol/L to 1 mmol/L of forskolin or 0.1 ng/mL to 1 mg/mL of platelet-derived growth factor (PDGF), or the like.

The medium may be any medium as long as it is a medium which does not obstruct differentiation into neurons. For example, it is preferable to use DMEM/F12 medium (manufactured by Invitrogen) containing 1% N-2 additives (manufactured by Invitrogen), and the like.

Additionally, the neural stem cells prepared by the above-mentioned culturing can be differentiated into glial cells, by carrying out static culturing at 37° C. for 1 to 14 days under an atmosphere of 5% $CO_2$, while exchanging the whole volume or a partial volume of a medium at intervals of 2 days, in a medium which does not contain the compound of the present invention but contains, for example, 0.1 ng/mL to 1 mg/mL of leukemia inhibitory factor (LIF), 0.1 ng/mL to 1 mg/mL of bone morphogenic protein-2 (BMP-2), or the like.

The medium may be any medium as long as it is a medium which does not obstruct differentiation into glial cells. For example, it is preferable to use DMEM/F12 medium (manufactured by Invitrogen) containing 1% N-2 additives (manufactured by Invitrogen), and the like.

The neural stem cells, neuron or glial cells which are prepared by the above-mentioned culturing can be used in the treatment of a neurological disorder, by recovering them from the medium and transplanting them into the focus of a patient of the neurological disorder by a surgical technique. The neurological disorder include, for example, Parkinson's disease, Alzheimer's disease, Down syndrome, cerebrovascular disorders, stroke, spinal cord injury, triplet repeat disease, multiple sclerosis, amyotrophic lateral sclerosis, polyneuropathy, epilepsy, anxiety disorder, schizophrenia, depression, manic depressive psychosis and the like.

Next, proliferation promoting activity of typical compounds is specifically described based on test examples. The following test examples are provided for the exemplification purpose only. Accordingly, the scope of the present invention is not limited to the following test examples.

Test Example 1

Proliferation Promoting Activity on Neural Stem Cells

Rat adult neural stem cell line ANSC-7 cells prepared by the method described in the following Reference Test Example 1 were suspended in assay medium at a density of 1.6×10⁵ cells/mL; inoculated at 0.1 mL in a 96 well plate (manufactured by Costar) of which surface was coated with polyornithine and laminin; and cultured overnight at 37° C. under an atmosphere of 5% $CO_2$. Thereafter, 50 μL of the culture supernatant was removed, and 50 μL of a test compound which was serially diluted with the assay medium to 2 times of the final concentration or DMSO (negative control) was added to each well. For the serial dilution of a test compound, non-specific adsorption was minimized by using ProteoSave 96 U plates (manufactured by SUMILON), siliconized 1.5 mL tubes (manufactured by Assist) and Pitarack siliconized tips (manufactured by Nacalai). After the culturing for 48 hours, 50 μL of the culture supernatant was replaced by 50 μL of the assay medium containing 0.1% bovine fetal serum. Furthermore, after the culturing for 48 hours, Living Cell Count Reagent SF (manufactured by Nacalai Tesque) was added at the volume of 10 μL per well to the medium. After the culturing for 3 hours at 37° C. in the incubator which was set at 5% $CO_2$, the resulting solution was stirred for one minute and then the absorbance at 490 nm (control wavelength 655 nm) was measured by using Microplate Spectrophotometer Emax (manufactured by Molecular Devices). By regarding the measured value of well to which the cells were not inoculated as 0%, and the measured value of negative control as 100%, relative values in the test compound addition group were calculated.

Each of the compounds 1, 2, 3, 4, 31, 32, 33, 46, 48, 53, 54, 66, 69, 79, 81, 83, 99 and 105 showed a proliferation promoting activity of 125% or more at 1.0 nmol/L. Also, each of the compounds 34, 36, 74, 75, 76, 80, 90 and 94 showed a proliferation promoting activity of 125% or more at 10 nmol/L. Additionally, each of the compounds 21, 30, 47, 72, 78 and 93 showed a proliferation promoting activity of 125% or more at 100 nmol/L.

Reference Test Example 1

Isolation and Culturing of Adult Neural Stems Cells from Rat Brain

After putting a 7-week-old Sprague Dawley Rat to sleep by ether anesthesia and subsequent decapitation, the skull was cut open from the parietal region to extract the brain. Under a microscope, tissues including circumventricular region were isolated from the extracted brain by using ophthalmic scissors and tweezers. The tissues including circumventricular region were cut into fragments of about 1 mm³ using ophthalmic scissors and scalpels and then subjected to 30 minutes of digestion reaction at 37° C. in 5 mL of Hanks' buffer (HBSS buffer, manufactured by Invitrogen) containing 2.5 U/mL of papain, 250 U/mL of DNase (all manufactured by Worthington, Freehold, N.J.) and 1 U/mL of a neutral protease (Dispase, manufactured by Boehringer-Mannheim Corp.). The mixture of cells and tissues obtained by the reaction was washed three times with DMEM (manufactured by Invitrogen) containing 10% fetal bovine serum (manufactured by Hyclone) and then dissolved in the DMEM containing 10% fetal bovine serum, followed by removing the undigested materials using a nylon mesh of 10 μM.

The resulting crude cells extract was cultured overnight on a culture dish of 10 cm, in an incubator of 37° C. using DMEM/F12 medium (manufactured by Invitrogen) containing 10% fetal bovine serum. On the next day, the medium was replaced with DMEM/F12 containing 1% of N-2 additives (manufactured by Invitrogen) and 20 ng/mL of FGF 2 (manufactured by Pepro Tech) and the culturing was started. Once in 3 days, half of the medium was replaced with new DMEM/F12 containing 1% of N-2 additives and 20 ng/mL of FGF 2 and the culturing was continued.

When a small colony consisting of small cells was formed, it was treated with 1% trypsin for 30 seconds to 1 minute, and the cells detached were harvested. The harvested cells were inoculated on a multiple well culture dish (manufactured by Fisher Scientific) which had been coated at room temperature overnight using 10 μg/mL of polyornithine (manufactured by Sigma) and at 37° C. overnight using 5 μg/mL of mouse EHS tumor-derived laminin (Becton Dickinson), and the culturing was continued.

By continuing the above-mentioned culturing, small cells having small protrusion and thickness were concentrated. The cells were used as adult neural stem cells in the above-mentioned test (Test Example 1).

Although the present invention is explained in more detail based on examples and reference examples, the scope of the present invention is not limited to these examples.

The proton nuclear magnetic resonance spectra (¹H NMR) used in Examples and Reference Examples were measured at 270 MHz or 300 MHz, and exchangeable protons may not be clearly observed depending on the compound and the measurement condition. Further, common notation is used to represent signal multiplicity. Mass spectrometry was performed by using electrospray ionization (ESI) or atmospheric pressure chemical ionization (APCI). Further, ChemBioDraw Ultra Version 11 (CambridgeSoft) was used for the nomenclature of compounds P5, P51 to P55, P59 to P70, P73 to P81, P83 to P85, 34, 65 to 75, 81 to 83, 93, 95 to 99, 107, 110 and 111.

Reference Example 1

(S)-3-Triethylsiloxy-5,7-cholestadiene (Compound P1)

Commercially available 7-dehydrocholesterol (10.6 g, 27.6 mmol) was dissolved in dichloromethane (90 mL), and then imidazole (3.75 g, 55.1 mmol) and chlorotriethylsilane (6.94 mL, 41.3 mmol) were added at room temperature, followed by stirring for 12 hours. A saturated aqueous ammonium chloride solution was added to the reaction mixture, followed by extraction with chloroform twice. The organic layer was washed with saturated brine, dried over anhydrous magnesium sulfate, and concentrated under reduced pressure to yield a residue. The residue was purified by silica gel column chromatography to obtain the title compound (12.0 g, 87%).

¹H NMR (CDCl₃) δ(ppm): 0.61 (q, J=7.9 Hz, 6H), 0.62 (s, 3H), 0.86 (d, J=7.0 Hz, 3H), 0.89 (d, J=7.0 Hz, 3H), 0.95-1.02

(m, 15H), 1.05-2.15 (m, 23H), 2.32-2.38 (m, 2H), 3.52-3.66 (m, 1H), 5.39 (m, 1H), 5.56 (d, J=5.6 Hz, 1H).

Reference Example 2

(3S,5S,6S)-3-Triethylsiloxy-7-cholesten-6-ol (Compound P2)

Compound P1 (10.1 g, 20.2 mmol) obtained in Reference Example 1 was dissolved in THF (140 mL), and then 1.0 mol/L of a borane-THF complex/THF solution (20.2 mL, 20.2 mmol) was added at 0° C., followed by stirring at room temperature for 40 minutes. The reaction mixture was cooled to 0° C., and then water (5 mL) was slowly added thereto. Subsequently, 30% aqueous hydrogen peroxide (6.26 mL, 60.7 mmol) and 10% aqueous sodium hydroxide solution (22.1 mL, 60.7 mmol) were added, followed by stirring at room temperature for 1 hour. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain the title compound (8.43 g, 80%).
$^1$H NMR (CDCl$_3$) δ(ppm): 0.54 (s, 3H), 0.60 (q, J=7.9 Hz, 6H), 0.83 (s, 3H), 0.85 (d, J=6.6 Hz, 3H), 0.87 (d, J=6.6 Hz, 3H), 0.92 (d, J=6.3 Hz, 3H), 0.96 (t, J=7.9 Hz, 9H), 0.99-2.18 (m, 26H), 3.53 (m, 1H), 3.79 (m, 1H), 5.18 (m, 1H).

Reference Example 3

(3S,5S,6S)-7-Cholesten-3,6-diol (Compound P3)

Compound P2 (9.60 g, 18.6 mmol) obtained in Reference Example 2 was dissolved in THF (60 mL), and then 1.0 mol/L of a tetrabutylammonium fluoride/THF solution (27.9 mL, 27.9 mmol) was added at room temperature, followed by stirring at 50° C. for 30 minutes. After cooling to room temperature, a saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain the title compound (7.40 g, 99%).
$^1$H NMR (CDCl$_3$) δ(ppm): 0.54 (s, 3H), 0.84 (s, 3H), 0.85 (d, J=6.6 Hz, 3H), 0.88 (d, J=6.6 Hz, 3H), 0.92 (d, J=6.3 Hz, 3H), 0.98-1.95 (m, 24H), 2.04 (m, 1H), 2.25 (m, 1H), 3.59 (m, 1H), 3.80 (m, 1H), 5.18 (m, 1H).

Reference Example 4

(S)-7-Cholesten-3,6-dione (Compound P4)

Compound P3 (7.40 g, 18.4 mmol) obtained in Reference Example 3 and 4-methylmorpholine N-oxide (7.54 g, 64.3 mmol) were dissolved in dichloromethane (180 mL), and then powdered Molecular Sieves 4 Å (15.0 g) and tetrapropylammonium perruthenate (194 mg, 0.551 mmol) were added at room temperature, followed by stirring for 8 hours. The reaction mixture was filtered through a celite, and then the filtrate was concentrated under reduced pressure to yield a residue. The residue was purified by silica gel column chromatography to obtain the title compound (6.53 g, 89%).
$^1$H NMR (CDCl$_3$) δ(ppm): 0.64 (s, 3H), 0.86 (d, J=6.6 Hz, 3H), 0.88 (d, J=6.6 Hz, 3H), 0.95 (d, J=6.3 Hz, 3H), 1.00-1.24 (m, 7H), 1.26-2.70 (m, 22H), 5.78 (m, 1H)

Reference Example 5

(1S,2R)-2-Methyl-2-[(1R,3aR,5R,7aR)-7a-methyl-1-[(R)-6-methylheptan-2-yl]-4-oxooctahydro-1H-inden-5-yl]-5-oxocyclohexanecarboxylic acid (Compound P5)

Sodium periodate (11.4 g, 53.4 mmol) and cerium chloride heptahydrate (3.32 g, 8.91 mmol) were dissolved in water (70 mL), then ethyl acetate (210 mL), acetonitrile (210 mL), and compound P4 (3.55 g, 8.91 mmol) obtained in Reference Example 4 were added thereto. The mixture was cooled to 0° C., and ruthenium chloride hydrate (554 mg, 2.67 mmol) was added thereto, followed by stirring for 40 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain a crude purified product of (5S,7S,8S)-7,8-dihydroxy-3,6-chlestadione (2.95 g). This was dissolved in pyridine (50 mL), and then lead tetraacetate (11.3 g, 20.5 mmol) was added at 0° C. thereto, followed by stirring for 40 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain the title compound (1.39 g, 37%).
$^1$H NMR (CDCl$_3$) δ(ppm): 0.62 (s, 3H), 0.86 (d, J=7.0 Hz, 3H), 0.88 (d, J=7.0 Hz, 3H), 0.94 (d, J=5.6 Hz, 3H), 0.99-1.96 (m, 19H), 2.10-2.55 (m, 7H), 2.60-2.75 (m, 2H), 3.26 (m, 1H).

Reference Example 6

3-(Methoxymethyloxy)-cholest-5,7-diene (Compound P6)

In dichloromethane (45 mL), 7-dehydrocholesterol (2.0 g, 5.2 mmol) was dissolved, then N,N-diisopropylethylamine (2.70 mL, 15.6 mmol) and chloromethylmethylether (1.00 mL, 13.2 mmol) were sequentially added under ice-cooling, followed by stirring at room temperature for 20 hours. The reaction mixture was poured into a saturated aqueous ammonium chloride solution, followed by extraction with ethyl acetate (100 mL×2). The organic layer was washed with dilute aqueous hydrochloric acid and saturated brine, dried over anhydrous sodium sulfate, and concentrated to yied a residue. To the residue, methanol was added to triturate to obtain the title compound (1.9 g, 83%).
$^1$H NMR δ(ppm, CDCl$_3$): 5.56 (1H, m), 5.39 (1H, m), 4.71 (2H, s), 3.53 (1H, m), 3.38 (3H, s), 2.52 (1H, m), 2.32 (1H, m), 2.09 (1H, m), 1.96-1.87 (5H, m), 1.74-0.99 (17H, m), 0.94 (3H, s), 0.94 (3H, d, J=6.4 Hz), 0.87 (3H, d, J=6.6 Hz), 0.86 (3H, d, J=6.6 Hz), 0.61 (3H, s).

Reference Example 7

3-(Methoxymethyloxy)-cholest-7-en-6-ol (Compound P7)

Compound P6 (887.1 mg, 2.100 mmol) obtained in Reference Example 6 was dissolved in THF (15 mL), and then dimethyl sulfide-borane (1.0 mL, 10 mmol) was added dropwise under ice-cooling thereto, followed by stirring at room temperature for 2 hours. The reaction mixture was again ice-cooled, and then water (10 mL), 1.0 mol/L of an aqueous solution of sodium hydroxide (10 mL) and 34.5% aqueous hydrogen peroxide (3 mL) were sequentially added dropwise, followed by stirring at room temperature for 1 hour. A saturated aqueous sodium sulfite solution was added to the reaction mixture, followed by extraction with chloroform (75 mL×2). The organic layer was washed with saturated brine, dried over anhydrous sodium sulfate, and concentrated to yield a residue (1.1 g), which was purified by silica gel column chromatography (10 to 40% ethyl acetate/n-hexane) to obtain the title compound (650 mg, 70%).

$^1$H NMR $\delta$(ppm, CDCl$_3$): 5.17 (1H, br s), 4.69 (2H, m), 3.78 (1H, br d, J=8.1 Hz), 3.48 (1H, m), 3.36 (3H, s), 2.30 (1H, m), 2.03 (1H, m), 1.83-0.97 (25H, m), 0.90 (3H, d, J=6.2 Hz), 0.85 (3H, d, J=6.6 Hz), 0.85 (3H, d, J=6.6 Hz), 0.83 (3H, s), 0.53 (3H, s).

Reference Example 8

3-(Methoxymethyloxy)-cholest-7-en-6-one (Compound P8)

Compound P7 (650 mg, 1.46 mmol) obtained in Reference Example 7 was dissolved in dichloromethane (30 mL), and then manganese (IV) oxide (8.5 g) was added thereto, followed by stirring at room temperature for 12 hours. The reaction mixture was filtered by using celite, and the filtrate was concentrated, followed by purification by silica gel column chromatography (10 to 20% ethyl acetate/n-hexane) to obtain the title compound (540 mg, 83%).

$^1$H NMR $\delta$(ppm, CDCl$_3$): 5.72 (1H, br s), 4.74-4.66 (2H, m), 3.53 (1H, m), 3.38 (3H, s), 2.30-0.98 (26H, m), 0.94 (3H, d, J=6.1 Hz), 0.87 (6H, d, J=6.6 Hz), 0.87 (3H, s), 0.60 (3H, s).

Reference Example 9

3-(Methoxymethyloxy)-6,8-seco-7-norcholestan-6-oic acid-8-one (Compound P9)

Compound P8 (190.9 mg, 0.4300 mmol) obtained in Reference Example 8 and sodium periodate (410 mg, 1.92 mmol) were suspended in a mixed solvent of chloroform (5 mL)-acetonitrile (2.5 mL)-water (5 mL), and then a small amount of ruthenium chloride hydrate was added thereto, followed by stirring at room temperature for 18 hours. A small amount of isopropanol and water were added to the reaction mixture and then stirred, followed by extraction with chloroform (40 mL×3). The organic layer was sequentially washed with a saturated aqueous sodium sulfite solution and saturated brine, dried over anhydrous sodium sulfate, and concentrated. The resulting residue was dissolved in toluene (10 mL), and then lead acetate (1.20 g, 2.71 mmol) was added, followed by stirring at room temperature for 22 hours. A small amount of isopropanol was added to the reaction mixture and stirred, followed by filtration using celite. Water was added to the filtrate, followed by extraction with chloroform (20 mL×3). The organic layer was washed with saturated brine, dried over anhydrous sodium sulfate, and concentrated to yield a residue. The residue was purified by silica gel column chromatography (10 to 40% ethyl acetate/n-hexane) to obtain the title compound (48.5 mg, 24%). At that time, 68.2 mg of compound P8 (yield 36%) was recovered.

$^1$H NMR $\delta$(ppm, CDCl$_3$): 4.67 (2H, s), 3.45 (1H, m), 3.36 (3H, s), 2.67 (1H, dd, J=12.8, 3.9 Hz), 2.55-2.44 (2H, m), 2.27-1.12 (24H, m), 1.25 (3H, s), 0.93 (3H, d, J=5.5 Hz), 0.87 (3H, d, J=6.6 Hz), 0.86 (3H, d, J=6.6 Hz), 0.59 (3H, s).

Reference Example 10

3-(Methoxymethyloxy)-ergosta-5,7,22-triene (Compound P10)

Ergosterol (35.7 g, 90.0 mmol) was dissolved in dimethoxymethane (350 mL, 6.3 mol), and diphosphorous pentoxide (17.9 g, 126 mmol) was added thereto, followed by stirring at room temperature for 1 hour. Diatomaceous earth was added to the reaction mixture, followed by stirring for 30 minutes and filtration, and the filtrate was concentrated. Ethyl acetate was added to the resulting residue for trituration to obtain the title compound (35.1 g, 89%).

$^1$H NMR $\delta$(ppm, CDCl$_3$): 5.56 (1H, m), 5.38 (1H, m), 5.12-5.27 (2H, m), 4.71 (2H, s), 3.53 (1H, m), 3.38 (3H, s), 2.52 (1H, m), 2.32 (1H, m), 2.07-1.26 (18H, m), 1.03 (3H, d, J=6.6 Hz), 0.94 (3H, s), 0.91 (3H, d, J=6.8 Hz), 0.84 (3H, d, J=6.8 Hz), 0.82 (3H, d, J=6.8 Hz), 0.63 (3H, s).

Reference Example 11

3-(Methoxymethyloxy)-5,8-(1,2,3,4-tetrahydro-1,4-dioxophthalazin-2,3-diyl)-ergosta-6,22-diene (Compound P11)

Compound P10 (11.1 g, 25.3 mmol) obtained in Reference Example 10 and phthalhydrazide (10.3 g, 63.3 mmol) were dissolved in dichloromethane (150 mL), and a solution of lead acetate (14.6 g, 32.9 mmol) in dichloromethane (50 mL)-acetic acid (2.55 mL) was added dropwise at 0° C. thereto. After the mixture was stirred at 0° C. for 45 minutes, alumina (50 g) was added to stop the reaction. After filtration, the filtrate was washed with water, a saturated aqueous ammonium chloride solution and saturated brine, sequentially, and dried over anhydrous sodium sulfate, followed by purification by silica gel column chromatography (10 to 40% ethyl acetate/n-hexane) to obtain the title compound (8.0 g, 53%).

$^1$H NMR $\delta$(ppm, CDCl$_3$): 8.13 (2H, m), 7.68 (2H, m), 6.65 (1H, d, J=8.1 Hz), 6.27 (1H, d, J=8.1 Hz), 5.10-5.26 (2H, m), 4.72 (1H, d, J=6.6 Hz), 4.63 (1H, d, J=6.6 Hz), 4.07 (1H, dd, J=13.8, 8.9 Hz), 3.94 (1H, dd, J=11.9, 7.7 Hz), 3.54 (1H, m), 3.34 (3H, s), 2.11-1.34 (18H, m), 1.02 (3H, s), 1.01 (3H, d, J=6.1 Hz), 0.89 (3H, d, J=6.8 Hz), 0.84 (3H, s), 0.82 (3H, d, J=7.0 Hz), 0.81 (3H, d, J=6.8 Hz).

Reference Example 12

3-(Methoxymethyloxy)-5,8-(1,2,3,4-tetrahydro-1,4-dioxophthalazin-2,3-diyl)-pregna-6-en-22-al (Compound P11)

Compound P11 (8.00 g, 13.4 mmol) obtained in Reference Example 11 was dissolved in a mixed solvent of dichloromethane (120 mL) and pyridine (22.0 mL, 268 mmol), followed by passing through an ozone-oxygen stream at −78° C. for 60 minutes. Residual ozone was removed by passing through a nitrogen stream, and dimethylsulfide (5.0 mL, 68 mmol) was added dropwise at −78° C. thereto, followed by stirring for 30 minutes while increasing the temperature to room temperature. The reaction mixture was washed with dilute aqueous hydrochloric acid and saturated brine, and dried over anhydrous sodium sulfate. The residue obtained by concentration was purified by silica gel column chromatography (20 to 80% ethyl acetate/n-hexane) to obtain the title compound (5.3 g, 74%).

$^1$H NMR δ(ppm, CDCl$_3$): 9.56 (1H, d, J=3.5 Hz), 8.13 (2H, m), 7.70 (2H, m), 6.68 (1H, d, J=8.3 Hz), 6.25 (1H, d, J=8.3 Hz), 4.72 (1H, d, J=6.6 Hz), 4.64 (1H, d, J=6.6 Hz), 4.10-4.00 (2H, m), 3.55 (1H, m), 3.35 (3H, s), 2.35 (1H, m), 2.31-1.98 (4H, m), 1.94-1.25 (11H, m), 1.14 (3H, d, J=6.8 Hz), 1.03 (3H, s), 0.88 (3H, s).

Further, compound P12 may also be synthesized in accordance with methods as described in *Chemistry-A European Journal*, 2001, vol. 7, p. 2663-2670.

Reference Example 13

20-Hydroxymethyl-3-(methoxymethyloxy)-pregna-5,7-diene (Compound P13)

Compound P12 (230 mg, 0.432 mmol) obtained in Reference Example 12 and lithium aluminium hydride (163 mg, 4.30 mmol) were suspended in THF (50 mL), followed by stirring at 80° C. for 1 hour. The mixture was cooled to 0° C., and 1.0 mol/L potassium sodium tartrate was added dropwise thereto, followed by extraction with ethyl acetate (50 mL×2). The organic layer was washed with saturated brine, dried over anhydrous sodium sulfate, and concentrated to yield a residue (260 mg), which was purified by silica gel column chromatography (10 to 30% ethyl acetate/n-hexane) to obtain the title compound (116.5 mg, 72%).

$^1$H NMR δ(ppm, CDCl$_3$): 5.55 (1H, m), 5.37 (1H, m), 4.70 (2H, s), 3.63 (1H, dd, J=10.5, 3.1 Hz), 3.52 (1H, m), 3.37 (1H, m), 3.37 (3H, s), 2.51 (1H, m), 2.31 (1H, m), 2.08-1.26 (17H, m), 1.06 (3H, d, J=6.6 Hz), 0.93 (3H, s), 0.63 (3H, s).

Further, compound P13 may also be synthesized in accordance with methods as described in *Organic Letters* (2003), vol. 5, p. 1837-1839.

Reference Example 14

20-(Acetyloxymethyl)-3-(methoxymethyloxy)-pregna-5,7-diene (Compound P14)

Compound P13 (116.5 mg, 0.3110 mmol) obtained in Reference Example 13 was dissolved in dichloromethane (7 mL), and then pyridine (1.5 mL) and acetic anhydride (1.5 mL) were added thereto, followed by stirring at room temperature for 14 hours. The reaction mixture was concentrated under reduced pressure, followed by purification by silica gel column chromatography (0 to 20% ethyl acetate/n-hexane) to obtain the title compound (122.1 mg, 94%).

$^1$H NMR δ(ppm, CDCl$_3$): 5.57 (1H, m), 5.38 (1H, m), 4.70 (2H, s), 4.09 (1H, dd, J=3.5, 10.8 Hz), 3.79 (1H, dd, J=10.8, 7.5 Hz), 3.53 (1H, m), 3.38 (3H, s), 2.52 (1H, m), 2.32 (1H, m), 2.27-1.24 (16H, m), 2.06 (3H, s), 1.04 (3H, d, J=6.6 Hz), 0.94 (3H, s), 0.64 (3H, s).

Reference Example 15

20-(Acetyloxymethyl)-3-(methoxymethyloxy)-pregna-7-en-6-ol (Compound P15)

Compound P14 (122.1 mg, 0.2940 mmol) obtained in Reference Example 14 was treated with dimethyl sulfide-borane (0.20 mL, 2.11 mmol), 1.0 mol/L of a sodium hydroxide aqueous solution (0.25 mL) and 34.5% aqueous hydrogen peroxide (0.70 mL) in the same manner as Reference Example 2 to obtain the title compound (85.6 mg, 67%).

$^1$H NMR δ(ppm, CDCl$_3$): 5.16 (1H, br s), 4.68 (2H, m), 4.08 (1H, dd, J=10.6, 3.3 Hz), 3.76 (2H, m), 3.47 (1H, m), 3.35 (3H, s), 2.29 (1H, m), 2.03 (3H, s), 2.07-0.85 (19H, m), 1.00 (3H, d, J=6.6 Hz), 0.82 (3H, s), 0.54 (3H, s).

Reference Example 16

20-(Acetyloxymethyl)-3-(methoxymethyloxy)-pregna-7-en-6-one (Compound P16)

Compound P15 (85.6 mg, 0.197 mmol) obtained in Reference Example 15 was treated with manganese (IV) oxide (850 mg) in the same manner as Reference Example 8 to obtain the title compound (78.4 mg, 92%).

$^1$H NMR δ(ppm, CDCl$_3$): 5.69 (1H, br s), 4.70 (1H, d, J=6.8 Hz), 4.64 (1H, d, J=6.8 Hz), 4.05 (1H, dd, J=10.8, 3.5 Hz), 3.77 (1H, dd, J=10.8, 7.3 Hz), 3.49 (1H, m), 3.30 (3H, s), 2.26-1.22 (19H, m), 2.02 (3H, s), 1.01 (3H, d, J=6.6 Hz), 0.84 (3H, s), 0.59 (3H, s).

Reference Example 17

20-(Acetyloxymethyl)-3-(methoxymethyloxy)-6,8-seco-7-norpregnan-6-oic acid-8-one (Compound P17)

Compound P16 (130 mg, 0.300 mmol) obtained in Reference Example 16 was treated with a small amount of ruthenium chloride hydrate, sodium periodate (210 mg, 1.08 mmol) and lead acetate (400 mg, 0.902 mmol) in the same manner as Reference Example 5 to obtain the title compound (45.3 mg, 33%).

$^1$H NMR δ(ppm, CDCl$_3$): 4.65 (2H, s), 4.04 (1H, m), 3.78 (1H, m), 3.50 (1H, m), 3.34 (3H, s), 2.50-1.99 (20H, m), 2.04 (3H, s), 1.00 (3H, d, J=6.5 Hz), 0.93 (3H, s), 0.60 (3H, s).

Reference Example 18

3-(Methoxymethyloxy)-5,8-(1,2,3,4-tetrahydro-1,4-dioxophthalazin-2,3-diyl)-cholest-6-en-22-ol (Compound P18)

A THF solution (10 mL) of compound P12 (1.37 g, 2.58 mmol) obtained in Reference Example 12 was added dropwise at −78° C. to a THF-diethyl ether solution (10 mL) of 3-methylbutylmagnesium bromide prepared from 1-bromo-3-methylbutane (2.00 mL, 15.7 mmol) and magnesium foil (400 mg, 16.5 mmol), followed by stirring at room temperature for 1 hour. A saturated aqueous ammonium chloride solution was added to the reaction mixture, followed by extraction with ethyl acetate. The organic layer was washed with saturated brine, dried over anhydrous sodium sulfate, and concentrated to yield a residue. The residue was purified by silica gel column chromatography (10 to 70% ethyl acetate/n-hexane) to obtain the title compound (500 mg, 32%).

$^1$H NMR δ(ppm, CDCl$_3$): 8.16-8.11 (2H, m), 7.73-7.66 (2H, m), 6.66 (1H, d, J=8.1 Hz), 6.27 (1H, d, J=8.1 Hz), 4.73-4.62 (2H, m), 4.10-3.93 (2H, m), 3.64 (1H, m), 3.55 (1H, m), 3.35 (3H, s), 2.07-1.98 (4H, m), 1.97-1.25 (18H, m), 1.03 (3H, s), 0.91 (3H, d, J=6.6 Hz), 0.89 (6H, d, J=6.6 Hz), 0.85 (3H, s).

Reference Example 19

3-(Methoxymethyloxy)-cholest-5,7-dien-22-ol (Compound P19)

Compound P18 (500 mg, 0.828 mmol) obtained in Reference Example 18 was treated with lithium aluminium hydride (350 mg, 9.22 mmol) in the same manner as Reference Example 13 to obtain the title compound (216 mg, 59%).

$^1$H NMR δ(ppm, CDCl$_3$): 5.57 (1H, dd, J=5.7, 2.4 Hz), 5.39 (1H, m), 4.71 (2H, s), 3.64 (1H, m), 3.53 (1H, m), 3.38 (3H, s), 2.52 (1H, m), 2.32 (1H, m), 2.10-1.08 (22H, m), 0.95 (3H, s), 0.93 (3H, d, J=6.8 Hz), 0.90 (6H, d, J=6.6 Hz), 0.63 (3H, s).

Reference Example 20

3-(Methoxymethyloxy)-cholest-7-en-6,22-diol (Compound P20)

Compound P19 (216.4 mg, 0.4870 mmol) obtained in Reference Example 19 was treated with 1.0 mol/L of a borane-THF complex (2.0 mL, 2.0 mmol), 34.5% aqueous hydrogen peroxide (1.0 mL, 10 mmol) and 6 mol/L of an aqueous solution of sodium hydroxide (1 mL, 6 mmol) in the same manner as Reference Example 2 to obtain the title compound (111.2 mg, 49%).

$^1$H NMR δ(ppm, CDCl$_3$): 5.19 (1H, br s), 4.73-4.68 (2H, m), 3.80 (1H, m), 3.63 (1H, m), 3.50 (1H, m), 3.38 (3H, s), 2.31 (1H, m), 2.04-1.07 (25H, m), 0.91 (3H, d, J=6.6 Hz), 0.89 (6H, d, J=6.4 Hz), 0.85 (3H, s), 0.56 (3H, s).

Reference Example 21

3-(Methoxymethyloxy)-cholest-7-en-6-on-22-ol (Compound P21)

Compound P20 (55.0 mg, 0.119 mmol) obtained in Reference Example 20 was treated with manganese oxide (500 mg, 5.75 mmol) in the same manner as Reference Example 8 to obtain the title compound (35.6 mg, 65%).

$^1$H NMR δ(ppm, CDCl$_3$): 5.71 (1H, br s), 4.73-4.64 (2H, m), 3.62 (1H, m), 3.51 (1H, m), 3.36 (3H, s), 2.28-1.03 (25H, m), 0.91 (3H, d, J=6.8 Hz), 0.88 (6H, d, J=6.6 Hz), 0.85 (3H, s), 0.60 (3H, s).

Reference Example 22

3-(Methoxymethyloxy)-22-(tert-butyldimethylsilyloxy)-cholest-7-en-6-one (Compound P22)

Compound P21 (35.6 mg, 0.0774 mmol) obtained in Reference Example 21 was dissolved in dichloromethane (2 mL), and 2,6-lutidine (0.050 mL, 0.43 mmol) and tert-butyldimethylsilyl trifluoromethanesulfonate (0.050 mL, 0.22 mmol) were added at 0° C. thereto, followed by stirring for 1 hour. Saturated brine was added to the reaction mixture, followed by extraction with chloroform. The organic layer was dried over anhydrous sodium sulfate, followed by purification by silica gel column chromatography (5 to 20% ethyl acetate/n-hexane) to obtain the title compound (43.5 mg, 98%).

$^1$H NMR δ(ppm, CDCl$_3$): 5.72 (1H, m), 4.74-4.65 (2H, m), 3.58 (1H, dd, J=7.9, 5.9 Hz), 3.52 (1H, m), 3.37 (3H, s), 2.29-0.99 (24H, m), 0.88 (3H, d, J=6.6 Hz), 0.87 (12H, s), 0.87 (6H, d, J=6.6 Hz), 0.60 (3H, s), 0.03 (3H, s), 0.02 (3H, s).

Reference Example 23

3-(Methoxymethyloxy)-22-(tert-butyldimethylsilyloxy)-6,8-seco-7-norcholest-8-on-6-oic acid (Compound P23)

Compound P22 (43.5 mg, 0.0758 mmol) obtained in Reference Example 22, sodium periodate (40.0 mg, 0.187 mmol) and cerium chloride heptahydrate (10.0 mg, 0.00268 mmol) were suspended in a mixed solvent of ethyl acetate (3 mL)-acetonitrile (3 mL)-water (5 mL), and then a small amount of ruthenium chloride hydrate was added thereto, followed by stirring at room temperature for 2 hours. Anhydrous sodium sulfate was added to the mixture, followed by filtration, and then, the filtrate was sequentially washed with a saturated aqueous sodium sulfite solution and saturated brine, and dried over anhydrous sodium sulfate. The residue obtained by concentration was dissolved in toluene (1.5 mL), and potassium carbonate (29.1 mg, 0.211 mmol) and lead acetate (54.5 mg, 0.123 mmol) were added thereto, followed by stirring at room temperature for 30 minutes. The reaction mixture was diluted with ethyl acetate, isopropanol (0.2 mL) and anhydrous sodium sulfate were added thereto, and then the mixture was filtrated. The filtrate was sequentially washed with a saturated aqueous sodium sulfite solution and saturated brine, and dried over anhydrous sodium sulfate. The residue obtained by concentration was purified by silica gel column chromatography (10 to 30% ethyl acetate/n-hexane) to obtain the title compound (9.2 mg, 21%).

$^1$H NMR δ(ppm, CDCl$_3$): 4.67 (2H, s), 3.57 (1H, dd, J=7.9, 5.9 Hz), 3.45 (1H, m), 3.36 (3H, s), 2.68 (1H, dd, J=12.5, 3.3 Hz), 2.57-0.94 (24H, m), 0.89-0.86 (21H), 0.59 (3H, s), 0.04 (3H, s), 0.03 (3H, s).

Reference Example 24

3-(Methoxymethyloxy)-22-(tert-butyldimethylsilyloxy)-7-oxa-cholest-8(9)-en-6-one (Compound P24)

Compound P23 (9.2 mg, 0.016 mmol) obtained in Reference Example 23 was treated with acetic anhydride (1.5 mL) and sodium acetate (100 mg, 1.22 mmol) in the same manner as Example 46 to obtain the title compound (3.7 mg, 41%).

$^1$H NMR δ(ppm, CDCl$_3$): 4.73-4.66 (2H, m), 3.58 (1H, dd, J=8.0, 6.2 Hz), 3.52 (1H, m), 3.38 (3H, s), 2.39-1.00 (23H, m), 0.97 (3H, s), 0.89-0.86 (18H), 0.68 (3H, s), 0.034 (3H, s), 0.028 (3H, s).

Reference Example 25

3-(Methoxymethyloxy)-5,8-(1,2,3,4-tetrahydro-1,4-dioxophthalazin-2,3-diyl)-cholest-6,22-dien-24-one (Compound P25)

Compound P12 (5.40 g, 10.1 mmol) obtained in Reference Example 12 and triphenylphosphine isobutanonmethylene (11.0 g, 31.8 mmol) were dissolved in anhydrous dimethyl sulfoxide (100 mL), followed by stirring at 95° C. for 72 hours. After being left to cool, the reaction mixture was poured into water, followed by extraction with ethyl acetate (200 mL×2). The organic layer was washed with saturated brine, and dried over anhydrous sodium sulfate. The residue (about 13 g) obtained by concentration was purified by silica gel column chromatography (20 to 60% ethyl acetate/n-hexane) to obtain the title compound (5.0 g, 82%).

$^1$H NMR δ(ppm, CDCl$_3$): 8.15-8.11 (2H, m), 7.70-7.67 (2H, m), 6.69 (1H, dd, J=15.8, 8.8 Hz), 6.67 (1H, d, J=8.6 Hz), 6.25 (1H, d, J=8.6 Hz), 6.05 (1H, d, J=15.8 Hz), 4.73-4.62 (2H, m), 4.10-3.96 (2H, m), 3.54 (1H, m), 3.34 (3H, s), 2.86 (1H, m), 2.28 (1H, m), 2.14-1.97 (3H, m), 1.88-1.25 (12H, m), 1.11 (3H, d, J=6.6 Hz), 1.09 (6H, d, J=7.0 Hz), 1.03 (3H, s), 0.87 (3H, s).

Reference Example 26

3-(Methoxymethyloxy)-5,8-(1,2,3,4-tetrahydro-1,4-dioxophthalazin-2,3-diyl)-cholest-6-en-24-one (Compound P26) and 3-(methoxymethyloxy)-5,8-(1,2,3,4-tetrahydro-1,4-dioxophthalazin-2,3-diyl)-cholest-6-en-24-ol (Compound 27)

Compound P25 (4.95 g, 8.25 mmol) obtained in Reference Example 25 was dissolved in methanol (50 mL), and nickel chloride hexahydrate (250 mg, 1.05 mmol) was added thereto, followed by stirring at 0° C. for 10 minutes. Next, sodium borohydride (811 mg, 21.4 mmol) was added in a small amount thereto, followed by stirring at 0° C. for 1 hour. Water was added to the reaction mixture, followed by extraction with ethyl acetate, and The organic layer was washed with saturated brine, and dried over anhydrous sodium sulfate. The residue obtained by concentration was purified by silica gel column chromatography (20 to 50% ethyl acetate/n-hexane) to obtain compound P26 (944 mg, 19%) and compound P27 (1.59 g, 32%).

Compound P26; $^1$H NMR δ(ppm, CDCl$_3$): 8.16-8.11 (2H, m), 7.72-7.65 (2H, m), 6.65 (1H, d, J=8.3 Hz), 6.26 (1H, d, J=8.3 Hz), 4.72-4.61 (2H, m), 4.06 (1H, dd, J=13.4, 4.4 Hz), 3.94 (1H, dd, J=12.1, 7.7 Hz), 3.54 (1H, m), 3.34 (3H, s), 2.60 (1H, m), 2.51-2.31 (2H, m), 2.12-1.22 (18H, m), 1.09 (6H, d, J=7.0 Hz), 1.02 (3H, s), 0.92 (3H, d, J=6.2 Hz), 0.82 (3H, s).

Compound P27; $^1$H NMR δ(ppm, CDCl$_3$): 8.15-8.10 (2H, m), 7.71-7.64 (2H, m), 6.64 (1H, d, J=8.1 Hz), 6.26 (1H, d, J=8.1 Hz), 4.72-4.61 (2H, m), 4.05 (1H, dd, J=13.8, 4.0 Hz), 3.95 (1H, dd, J=11.0, 7.0 Hz), 3.53 (1H, m), 3.33 (3H, s), 3.28 (1H, m), 2.12-1.25 (22H, m), 1.01 (3H, s), 0.93-0.87 (9H), 0.82 (3H, s).

Reference Example 27

3-(Methoxymethyloxy)-cholest-5,7-dien-24-ol (Compound P28)

A mixture of Compounds P26 and P27 (3.78 g, 6.30 mmol) obtained in Reference Example 26 were treated with lithium aluminium hydride (2.50 g, 65.9 mmol) in the same manner as Reference Example 13 to obtain the title compound (2.48 g, 89%).

$^1$H NMR δ(ppm, CDCl$_3$): 5.53 (1H, m), 5.35 (1H, m), 4.67 (2H, s), 3.50 (1H, m), 3.34 (3H, s), 3.27 (1H, m), 2.48 (1H, m), 2.29 (1H, m), 2.08-1.16 (22H, m), 0.91 (3H, s), 0.94-0.85 (9H), 0.59 (3H, s).

Reference Example 28

3-(Methoxymethyloxy)-cholest-7-en-6,24-diol (Compound P29)

Compound P28 (246.4 mg, 0.5950 mmol) obtained in Reference Example 27 was treated with 1.0 mol/L of a borane-THF complex (3.0 mL, 3.0 mmol), 34.5% aqueous hydrogen peroxide (1.0 mL, 10 mmol) and 6.0 mol/L of an aqueous solution of sodium hydroxide (1 mL, 6 mmol) in the same manner as Reference Example 2 to obtain the title compound (145.0 mg, 53%).

$^1$H NMR δ(ppm, CDCl$_3$): 5.15 (1H, br s), 4.69-4.64 (2H, m), 3.75 (1H, d, J=8.1 Hz), 3.46 (1H, m), 3.34 (3H, s), 3.27 (1H, s), 2.28 (1H, m), 2.03-1.00 (25H, m), 0.92-0.85 (9H), 0.81 (3H, s), 0.52 (3H, s).

Reference Example 29

3-(Methoxymethyloxy)-cholest-7-en-6,24-dione (Compound P30)

Compound P29 (145.0 mg, 0.314 mmol) obtained in Reference Example 28 was dissolved in dichloromethane, and Molecular Sieves 4 Å (160 mg), N-methylmorpholine oxide (110 mg, 0.942 mmol) and a small amount of tetrapropylammonium perruthenate were added thereto, followed by stirring at room temperature for 2 hours. The reaction mixture was filtered by using celite, and the filtrate was concentrated, followed by purification by silica gel column chromatography (10 to 30% ethyl acetate/n-hexane) to obtain the title compound (108.2 mg, 75%).

$^1$H NMR δ(ppm, CDCl$_3$): 5.67 (1H, s), 4.69-4.61 (2H, m), 3.48 (1H, m), 3.33 (3H, s), 2.56 (1H, m), 2.48-2.28 (2H, m), 2.24-1.17 (21H, m), 1.04 (6H, d, J=7.0 Hz), 0.89 (3H, d, J=6.1 Hz), 0.82 (3H, s), 0.55 (3H s).

Reference Example 30

3-(Methoxymethyloxy)-6,8-seco-7-norcholest-8,24-dion-6-oic acid (Compound P31)

Compound P30 (102.9 mg, 0.2250 mmol) obtained in Reference Example 29 was treated with a small amount of ruthenium chloride monohydrate, sodium periodate (150 mg, 0.701 mmol), cerium chloride heptahydrate (15.0 mg, 0.0403 mmol) and lead acetate (80.0 mg, 0.180 mmol) in the same manner as Reference Example 5 to obtain the title compound (17.7 mg, 17%).

$^1$H NMR δ(ppm, CDCl$_3$): 4.66 (2H, s), 3.44 (1H, m), 3.35 (3H, s), 2.68-1.38 (25H, m), 1.23 (3H, s), 1.080 (6H, d, J=6.8 Hz), 1.076 (3H, d, J=7.0 Hz), 0.58 (3H, s).

Reference Example 31

3-(Methoxymethyloxy)-5,8-(1,2,3,4-tetrahydro-1,4-dioxophthalazin-2,3-diyl)-chol-6,23-diene-22-ol (Compound P32)

Compound P12 (13.2 g, 24.8 mmol) obtained in Reference Example 12 was dissolved in anhydrous THF (50 mL) and 1 mol/L of a vinylmagnesium bromide-THF solution (40 mL, 40 mmol) was slowly added thereto dropwise under cooling at −78° C. The reaction mixture was stirred at −78° C. for 1 hour, and then a saturated aqueous ammonium chloride solution was added to increase the temperature to room temperature, followed by extraction with ethyl acetate (200 mL×2). The organic layer was washed with saturated brine, and dried over anhydrous sodium sulfate. The residue (about 12 g) obtained by concentration was purified by silica gel column chromatography (20 to 80% ethyl acetate/n-hexane) to obtain the title compound (10.3 g, 74%).

$^1$H NMR δ(ppm, CDCl$_3$): 8.16-8.11 (2H, m), 7.73-7.66 (2H, m), 6.66 (1H, d, J=8.3 Hz), 6.28 (1H, d, J=8.3 Hz), 5.85 (1H, m), 5.24 (1H, d, J=17.2 Hz), 5.16 (1H, d, J=10.6 Hz), 4.73-4.62 (2H, m), 4.29 (1H, br s), 4.04 (2H, m), 3.54 (1H, m), 3.35 (3H, s), 2.15-1.40 (17H, m), 1.03 (3H, s), 0.89 (3H, d, J=6.8 Hz), 0.85 (3H, s).

Reference Example 32

Ethyl 3-(methoxymethyloxy)-5,8-(1,2,3,4-tetrahydro-1,4-dioxophthalazin-2,3-diyl)-cholest-6,22-dien-26-oate (Compound P33)

Compound P32 (10.3 g, 18.4 mmol) obtained in Reference Example 31, triethyl orthopropionate (35.0 mL, 174 mmol) and propionic acid (1.50 mL, 20.1 mmol) were dissolved in toluene (75 mL) and Molecular Sieves 4 Å (30 g) were added, followed by stirring at 145° C. for 2 hours. After being left to cool, the reaction mixture was filtered, and water was added to the filtrate, followed by extraction with ethyl acetate (150 mL×2). The organic layer was washed with a saturated aqueous sodium bicarbonate solution and saturated brine, and dried over anhydrous sodium sulfate, followed by purification by silica gel column chromatography (20 to 60% ethyl acetate/n-hexane) to obtain the title compound (8.4 g, 71%).
$^1$H NMR δ(ppm, CDCl$_3$): 8.16-8.11 (2H, m), 7.71-7.66 (2H, m), 6.65 (1H, d, J=8.2 Hz), 6.26 (1H, d, J=8.2 Hz), 5.33-5.22 (2H, m), 4.72-4.63 (2H, m), 4.10 (2H, q, J=7.1 Hz), 4.07 (1H, m), 3.95 (1H, dd, J=12.0, 7.0 Hz), 3.55 (1H, m), 3.35 (3H, s), 2.47-1.27 (19H, m), 1.24 (3H, t, J=7.1 Hz), 1.11 (3H, d, J=6.9 Hz), 1.03 (3H, s), 1.01 (3H, d, J=6.6 Hz), 0.84 (3H, s).

Reference Example 33

Ethyl 3-(methoxymethyloxy)-5,8-(1,2,3,4-tetrahydro-1,4-dioxophthalazin-2,3-diyl)-cholest-6-en-26-oate (Compound P34)

Compound P33 (4.00 g, 6.21 mmol) obtained in Reference Example 32 was dissolved in ethyl acetate (80 mL), and then 10% palladium-carbon powders (400 mg) were added thereto, followed by stirring at room temperature for 3 hours under a hydrogen atmosphere. The catalyst was separated by filtration, and the filtrate was concentrated to obtain the title compound.
$^1$H NMR δ(ppm, CDCl$_3$): 8.16-8.11 (2H, m), 7.72-7.65 (2H, m), 6.65 (1H, d, J=8.1 Hz), 6.27 (1H, d, J=8.1 Hz), 4.73-4.62 (2H, m), 4.10 (2H, q, J=7.2 Hz), 4.07 (1H, m), 3.93 (1H, m), 3.54 (1H, m), 3.34 (3H, s), 2.48-1.28 (23H, m), 1.25 (3H, t, J=7.2 Hz), 1.10 (3H, d, J=7.2 Hz), 1.02 (3H, s), 1.00 (3H, d, J=7.2 Hz), 0.83 (3H, s).

Reference Example 34

3-(Methoxymethyloxy)-cholest-5,7-dien-26-ol (Compound P35)

Compound P34 obtained in Reference Example 33 was treated with lithium aluminium hydride (3.10 g, 81.7 mmol) in the same manner as Reference Example 13 to obtain the title compound (1.53 g, 56% (2 steps)).
$^1$H NMR δ(ppm, CDCl$_3$): 5.57 (1H, m), 5.38 (1H, m), 4.71 (2H, s), 3.52 (2H, m), 3.44 (1H, m), 3.38 (3H, s), 2.52 (1H, m), 2.25 (1H, m), 2.06-1.25 (24H, m), 1.03 (3H, d, J=6.6 Hz), 0.94 (3H, s), 0.92 (3H, d, J=6.4 Hz), 0.63 (3H, s).

Reference Example 35

3-(Methoxymethyloxy)-cholest-7-en-6,26-diol (Compound P36)

Compound P35 (1.53 g, 3.45 mmol) obtained in Reference Example 34 was treated with 1.0 mol/L of a borane-THF complex/THF solution (16 mL, 16 mmol), 6.0 mol/L of an aqueous solution of sodium hydroxide (5.80 mL, 34.5 mmol) and 30% aqueous hydrogen peroxide (3.90 mL, 34.5 mmol) in the same manner as Reference Example 2 to obtain the title compound (690 mg, 43%).
$^1$H NMR δ(ppm, CDCl$_3$): 5.17 (1H, br s), 4.72-4.66 (2H, m), 3.78 (1H, br d, J=8.3 Hz), 3.52-3.39 (3H, m), 3.36 (3H, s), 2.30 (1H, m), 2.02 (1H, m), 1.80-1.04 (26H, m), 0.91 (3H, d, J=6.6 Hz), 0.90 (3H, d, J=6.6 Hz), 0.83 (3H, s), 0.53 (3H, s).

Reference Example 36

3-(Methoxymethyloxy)-cholest-7-en-6-on-26-ol (Compound P37)

Compound P36 (690 mg, 1.49 mmol) obtained in Reference Example 35 was oxidized with manganese oxide (5 g, 57.5 mmol) in the same manner as Reference Example 8 to obtain the title compound (380 mg, 55%).
$^1$H NMR δ(ppm, CDCl$_3$): 5.72 (1H, br s), 4.74-4.66 (2H, m), 3.61-3.42 (3H, m), 3.38 (3H, s), 2.29-1.25 (27H, m), 0.93 (3H, d, J=7.0 Hz), 0.91 (3H, d, J=7.0 Hz), 0.86 (3H, s), 0.59 (3H, s).

Reference Example 37

3-(Methoxymethyloxy)-26-(triisopropylsilyloxy)-cholest-7-en-6-one (Compound P38)

Imidazole (190 mg, 2.79 mmol) and triisopropylsilane chloride (0.30 mL, 1.40 mmol) were added to an anhydrous DMF solution (6 mL) containing compound P37 (290 mg, 0.630 mmol) obtained in Reference Example 36, followed by stirring at room temperature for 2 hours. The reaction mixture was poured into a saturated aqueous ammonium chloride solution, followed by extraction with ethyl acetate (50 mL×2). The organic layer was washed with water and saturated brine, and dried over anhydrous sodium sulfate. The residue obtained by concentration was purified by silica gel column chromatography (10 to 40% ethyl acetate/n-hexane) to obtain the title compound (381 mg, 98%).
$^1$H NMR δ(ppm, CDCl$_3$): 5.72 (1H, br s), 4.74-4.66 (2H, m), 3.56-3.43 (3H, m), 3.38 (3H, s), 2.24-1.25 (26H, m), 1.06-1.05 (21H, m), 0.93 (3H, d, J=6.6 Hz), 0.88 (3H, d, J=6.6 Hz), 0.87 (3H, s), 0.60 (3H, s).

Reference Example 38

3-(Methoxymethyloxy)-26-(triisopropylsilyloxy)-cholest-6-on-7,8-diol (Compound P39)

Ethyl acetate (1 mL) and acetonitrile (3 mL) were sequentially added to an aqueous solution (1 mL) containing sodium periodate (51.8 mg, 0.242 mmol) and cerium chloride heptahydrate (36.1 mg, 0.0969 mmol). Subsequently, 0.1 mol/L of an aqueous solution of ruthenium chloride (0.21 mL, 0.021 mmol) was added thereto, followed by stirring at 0° C. for 10 minutes. An ethyl acetate solution (2 mL) of compound P37 (49.2 mg, 0.0799 mmol) obtained in Reference Example 36 was added to the mixture at 0° C., followed by stirring at room temperature for 1 hour. Anhydrous sodium sulfate (10 g) was added to the reaction mixture, followed by filtration, and the filtrate was washed with a saturated aqueous sodium sulfite solution and saturated brine, and dried over anhydrous sodium sulfate, followed by purification by silica gel column chromatography (10 to 30% ethyl acetate/n-hexane) to obtain the title compound (37.2 mg, 72%).

¹H NMR δ(ppm, CDCl₃): 4.70-4.65 (2H, m), 4.26 (1H, s), 3.56-3.41 (3H, m), 3.36 (3H, s), 2.50-1.09 (28H, m), 1.05-1.03 (21H, m), 0.89 (3H, d, J=6.4 Hz), 0.86 (3H, s), 0.84 (3H, d, J=7.0 Hz), 0.59 (3H, s).

Reference Example 39

3-(Methoxymethyloxy)-26-(triisopropylsilyloxy)-6,8-seco-7-norcholest-8-on-6-oic acid (Compound P40)

Potassium carbonate (106.5 mg, 0.7710 mmol) and lead (IV) tetraacetate (138.6 mg, 0.3130 mmol) were added to anhydrous toluene solution (10 mL) containing compound P39 (40.7 mg, 0.0626 mmol) obtained in Reference Example 38 at 0° C. The mixture was stirred at room temperature for 20 minutes, and then sodium sulfate (10 g) was added, followed by filtration. The filtrate was concentrated, followed by purification by silica gel preparative thin layer chromatography (n-hexane-ethyl acetate (3:1)) to obtain 3-(methoxymethyloxy)-26-(triisopropylsilyloxy)-6,8-seco-7-norcholest-8-on-6-oic acid (7.9 mg, 20%) and 3-(methoxymethyloxy)-26-(triisopropylsilyloxy)-7-oxa-cholest-8(9)-en-6-one (2.5 mg, 6.5%).

3-(methoxymethyloxy)-26-(triisopropylsilyloxy)-6,8-seco-7-norcholest-8-on-6-oic acid;
¹H NMR δ(ppm, CDCl₃): 4.67 (2H, s), 3.54-3.42 (3H, m), 3.36 (3H, s), 2.67-1.35 (27H, m), 1.24 (3H, s), 1.06-1.04 (21H, m), 0.92 (3H, d, J=6.8 Hz), 0.88 (3H, d, J=6.8 Hz), 0.58 (3H, s).

Reference Example 40

3-(Methoxymethyloxy)-26-(triisopropylsilyloxy)-7-oxa-cholest-8(9)-en-6-one (Compound P41)

Pyridine (100 μL) and thionyl chloride (50 μL) were added to an anhydrous dichloromethane solution (2 mL) containing compound P40 (11.8 mg, 0.0186 mmol) obtained in Reference Example 39 at 0° C., followed by stirring for 15 minutes. The reaction mixture was poured into a saturated ammonium chloride solution, followed by extraction with chloroform. The organic layer was washed with saturated brine, and dried over anhydrous sodium sulfate, followed by purification by silica gel preparative thin layer chromatography (n-hexane-ethyl acetate (3:1)) to obtain the title compound (9.1 mg, 79%).
¹H NMR δ(ppm, CDCl₃): 4.73-4.66 (2H, m), 3.54-3.43 (3H, m), 3.38 (3H, s), 2.34-1.25 (25H, m), 1.05-1.03 (21H, m), 0.97 (3H, s), 0.93 (3H, d, J=6.2 Hz), 0.88 (3H, d, J=6.8 Hz), 0.67 (3H, s).

Reference Example 41

3-(Methoxymethyloxy)-20-(hydroxymethyl)-pregna-7-en-6-ol (Compound P42)

Compound P13 (340 mg, 0.909 mg) obtained in Reference Example 13 was treated with 1.0 mol/L of a borane-THF complex (3.6 mL, 3.6 mmol), 6.0 mol/L of an aqueous solution of sodium hydroxide (1.5 mL, 9.0 mmol) and 34.5% aqueous hydrogen peroxide (1.0 mL, 10 mmol) in the same manner as Reference Example 2 to obtain the title compound (310 mg, 87%).
¹H NMR δ(ppm, CDCl₃): 5.19 (1H, br s), 4.71 (2H, m), 3.81 (1H, m), 3.65 (1H, m), 3.50 (1H, m), 3.39 (1H, m), 3.38 (3H, s), 2.31 (1H, m), 2.03 (1H, m), 1.92-1.13 (19H, m), 1.06 (3H, d, J=6.6 Hz), 0.85 (3H, s), 0.57 (3H, s).

Reference Example 42

3-(Methoxymethyloxy)-20-carboxy-pregna-7-en-6-on-22-oic acid (Compound P43)

Compound P42 (141.7 mg, 0.3610 mmol) obtained in Reference Example 41 was dissolved in acetone (10 mL), and then Jones reagent [prepared by dissolving 26.7 g of chromium (VI) oxide in 23 mL of conc. sulfuric acid-40 mL of water, and diluting with water to be 100 mL of whole volume] was slowly added dropwise until the solution turned limegreen color under ice-cooling. After stirring at 0° C. for 30 minutes, isopropanol (about 2 mL) was added to decompose the excess of the oxidizing agent. The reaction mixture was diluted with water, followed by extraction with ethyl acetate. The organic layer was washed with saturated brine, dried over anhydrous sodium sulfate, and concentrated to yield a residue (about 110 mg), to which a mixed solvent of ethyl acetate/n-hexane was added for crystallization to obtain the title compound (91.6 mg, 63%).
¹H NMR δ(ppm, CDCl₃): 5.73 (1H, s), 4.71 (2H, m), 3.53 (1H, m), 3.38 (3H, s), 2.46 (1H, m), 2.30-1.37 (19H, m), 1.28 (3H, d, J=6.8 Hz), 0.87 (3H, s), 0.63 (3H, s).

Reference Example 43 tert-Butyl 3-(methoxymethyloxy)-20-carboxy-pregna-7-en-6-on-22-oate (Compound P44)

Compound P43 (148.9 mg, 0.3690 mmol) obtained in Reference Example 42 and N,N-dimethylformamide tert-butyl acetal (707 μL, 2.95 mmol) were dissolved in toluene (2 mL), followed by stirring at 80° C. for 2 hours. The reaction mixture was concentrated, followed by purification by silica gel column chromatography (10 to 30% ethyl acetate/n-hexane) to obtain the title compound (126.8 mg, 75%).
¹H NMR δ(ppm, CDCl₃): 5.67 (1H, br s), 4.67 (2H, m), 3.50 (1H, m), 3.35 (3H, s), 2.29-2.01 (6H, m), 1.84-1.25 (13H, m), 1.41 (9H, s), 1.14 (3H, d, J=6.8 Hz), 0.84 (3H, s), 0.58 (3H, s).

Reference Example 44 tert-Butyl 3-(methoxymethyloxy)-20-carboxy-6,8-seco-7-norpregna-8-on-6-oate (Compound P45)

Compound P44 (80.8 mg, 0.176 mmol) obtained in Reference Example 43 was dissolved in acetic acid (3 mL), and lead acetate (330 mg, 0.744 mmol) and a small amount of ruthenium chloride hydrate were added thereto, followed by stirring at room temperature for 1 hour. Isopropanol (2 mL) was added to the reaction mixture, followed by filtration using celite, and the filtrate was extracted with ethyl acetate. The organic layer was sequentially washed with a saturated aqueous sodium sulfite solution and saturated brine, and dried over anhydrous sodium sulfate. The residue obtained by concentration was purified by silica gel column chromatography (10 to 50% ethyl acetate/n-hexane) to obtain the title compound (30.1 mg, 36%).
¹H NMR δ(ppm, CDCl₃): 4.66 (2H, m), 3.44 (1H, m), 3.35 (3H, s), 2.65 (1H, dd, J=12.8, 3.3 Hz), 2.57-1.25 (19H, m), 1.42 (9H, s), 1.23 (3H, s), 1.15 (3H, d, J=6.8 Hz), 0.58 (3H, s).

Reference Example 45

3-(Acetyloxy)-ergosta-5,7,22-triene (Compound P46)

Ergosterol (5.00 g, 12.6 mmol) was dissolved in dichloromethane (100 mL), and pyridine (4 mL) and acetyl chloride (2 mL) were sequentially added at 0° C. thereto, followed by stirring at room temperature for 18 hours. The reaction mixture was concentrated to yield a residue and then methanol was added to the obtained residue for trituration to obtain the title compound (5.21 g, 94%).
$^1$H NMR δ(ppm, CDCl$_3$): 5.57 (1H, dd, J=6.1, 2.4 Hz), 5.38 (1H, m), 5.13-5.27 (2H, m), 4.70 (1H, m), 2.50 (1H, m), 2.36 (1H, m), 2.04 (3H, s), 2.05-1.25 (18H, m), 1.04 (3H, d, J=6.6 Hz), 0.95 (3H, s), 0.92 (3H, d, J=7.0 Hz), 0.84 (3H, d, J=6.8 Hz), 0.82 (3H, d, J=6.8 Hz), 0.63 (3H, s), 5.57 (1H, dd, J=6.1, 2.4 Hz), 5.38 (1H, m), 5.13-5.27 (2H, m), 4.70 (1H, m), 2.50 (1H, m), 2.36 (1H, m), 2.04 (3H, s), 2.05-1.25 (18H, m), 1.04 (3H, d, J=6.6 Hz), 0.95 (3H, s), 0.92 (3H, d, J=7.0 Hz), 0.84 (3H, d, J=6.8 Hz), 0.82 (3H, d, J=6.8 Hz), 0.63 (3H, s).

Reference Example 46

3-(Acetyloxy)-ergosta-7,22-dien-6-ol (Compound P47)

Compound P46 (500 mg, 1.14 mmol) obtained in Reference Example 45 was dissolved in THF (13 mL), and then 1.0 mol/L of a borane-THF complex (2.3 mL, 2.3 mmol) was added dropwise under ice-cooling, followed by stirring at room temperature for 16 hours. The reaction mixture was again ice-cooled, and then water (4 mL), 1.0 mol/L of an aqueous solution of sodium hydroxide (4 mL) and 34.5% aqueous hydrogen peroxide (2.0 mL) were sequentially added dropwise, followed by stirring at room temperature for 2.5 hours. Water was added to the reaction mixture, followed by extraction with ethyl acetate (40 mL×2). The organic layer was washed with saturated brine, dried over anhydrous sodium sulfate, and concentrated to yield a residue (600 mg), which was purified by silica gel column chromatography (20 to 40% ethyl acetate/n-hexane) to obtain the title compound (120 mg, 23%).
$^1$H NMR δ(ppm, CDCl$_3$): 5.26-5.12 (3H, m), 4.70 (1H, m), 3.79 (1H, d, J=9.4 Hz), 2.30 (1H, m), 2.03 (3H, s), 1.86-1.25 (21H, m), 1.02 (3H, d, J=6.6 Hz), 0.91 (3H, d, J=6.8 Hz), 0.86 (3H, s), 0.84 (3H, d, J=6.8 Hz), 0.82 (3H, d, J=6.6 Hz), 0.55 (3H, s).

Reference Example 47

3-(Acetyloxy)-ergosta-7,22-dien-6-one (Compound P48)

Compound P47 (170 mg, 0.373 mmol) obtained in Reference Example 46 was dissolved in dichloromethane (30 mL), and then manganese (IV) oxide (1.25 g, 14.4 mmol) was added thereto, followed by stirring at room temperature for 17 hours. After the mixture was filtrated, the filtrate was concentrated to yield a residue (270 mg), which was purified by silica gel column chromatography (10 to 20% ethyl acetate/n-hexane) to obtain the title compound (108 mg, 64%).
$^1$H NMR δ(ppm, CDCl$_3$): 5.71 (1H, s), 5.27-5.11 (2H, m), 4.71 (1H, m), 2.42-1.10 (21H, m), 2.03 (3H, s), 1.03 (3H, d, J=6.6 Hz), 0.91 (3H, d, J=6.8 Hz), 0.87 (3H, s), 0.84 (3H, d, J=6.6 Hz), 0.83 (3H, d, J=6.6 Hz), 0.60 (3H, s).

Reference Example 48

3-(Acetyloxy)-ergosta-7-en-6-one (Compound P49)

The compound P48 (45.5 mg, 0.100 mmol) obtained in Reference Example 47 was dissolved in ethyl acetate (5 mL), and then 10% palladium-carbon (48 mg) was added, followed by stirring at room temperature for 1 hour under a hydrogen atmosphere. After filtration of the mixture, the filtrate was concentrated to yield a residue. The residue was purified by silica gel column chromatography (5 to 10% ethyl acetate/n-hexane) to obtain the title compound (34.6 mg, 76%).
$^1$H NMR δ(ppm, CDCl$_3$): 5.71 (1H, s), 4.71 (1H, m), 2.29 (1H, dd, J=12.3, 3.7 Hz), 2.23-1.20 (24H, m), 2.02 (3H, s), 0.93 (3H, d, J=6.8 Hz), 0.86 (3H, s), 0.84 (3H, d, J=7.0 Hz), 0.77 (6H, d, J=6.8 Hz), 0.58 (3H, s).

Reference Example 49

3-(Acetyloxy)-6,8-seco-7-norergosta-8-on-6-oic acid (Compound P50)

Compound P49 (172.9 mg, 0.3790 mmol) obtained in Reference Example 48 was dissolved in a mixed solvent of chloroform (2 mL)-acetonitrile (1 mL)-water (1 mL), and then sodium periodate (350 mg, 1.64 mmol) and a small amount of ruthenium chloride hydrate were added thereto, followed by stirring at room temperature for 2.5 hours. Isopropanol (3 mL) was added to the reaction mixture and stirred, followed by filtration using celite. Water was added to the filtrate, followed by extraction with chloroform (25 mL×2). The organic layer was washed with saturated brine, dried over anhydrous magnesium sulfate, and concentrated to yield a residue (220 mg). The residue was dissolved in toluene (5 mL), and lead acetate (210 mg, 0.474 mmol) was added thereto, followed by stirring at room temperature for 6 hours. The reaction mixture was filtrated by using celite, and water was added to the filtrate, followed by extraction with chloroform (25 ml×2). The organic layer was washed with saturated brine and dried over anhydrous magnesium sulfate, followed by purification by silica gel column chromatography (10 to 20% ethyl acetate/n-hexane) to obtain the title compound (24.0 mg, 13%).
$^1$H NMR δ(ppm, CDCl$_3$): 4.62 (1H, m), 2.70 (1H, dd, J=12.7, 3.3 Hz), 2.58-2.44 (2H, m), 2.33-2.29 (2H, m), 2.16-1.05 (21H, m), 2.02 (3H, s), 1.24 (3H, s), 0.94 (3H, d, J=6.0 Hz), 0.85 (3H, d, J=6.8 Hz), 0.77 (6H, d, J=6.6 Hz), 0.58 (3H, s).

Reference Example 50

(3S,10R,13R,14R,17R)-3-Methoxymethoxy-17-[(S)-1-methoxypropan-2-yl]-10,13-dimethyl-2,3,4,9,10,11,12,13,14,15,16,17-dodecahydro-1H-cyclopenta[α]phenanthrene (Compound P51)

Compound P13 (5.51 g, 14.7 mmol) obtained in Reference Example 13 and iodomethane (60.0 mL, 958 mmol) were dissolved in DMF (150 mL), and sodium hydride (4.95 g, 124 mmol) was added thereto, followed by stirring at room temperature for 2.5 hours. The solution was cooled to 0° C., and a saturated aqueous ammonium chloride solution was added dropwise, followed by extraction with diethyl ether (100 mL×2). The organic layer was washed with saturated brine, dried over anhydrous sodium sulfate, and concentrated to yield a residue. The residue was purified by silica gel column chromatography (10 to 30% ethyl acetate/n-hexane) to obtain the title compound (5.72 g, 100%).

$^1$H NMR δ(ppm, CDCl$_3$): 5.57 (1H, m), 5.38 (1H, m), 4.70 (2H, s), 3.53 (1H, m), 3.40 (1H, m), 3.38 (3H, s), 3.32 (3H, s), 3.13 (1H, dd, J=7.3 Hz, 16.1 Hz), 2.52 (1H, m), 2.33 (1H, m), 2.10-1.20 (16H, m), 1.06 (3H, d, J=6.6 Hz), 0.94 (3H, s), 0.63 (3H, s).

Reference Example 51

(3S,5S,6S,10R,13R,14R,17R)-3-Methoxymethoxy-17-[(S)-1-methoxypropan-2-yl]-10,13-dimethyl-2,3,4,5,6,9,10,11,12,13,14,15,16,17-tetradecahydro-1H-cyclopenta[α]phenanthren-6-ol (Compound P52)

Compound P51 (5.72 g, 14.7 mmol) obtained in Reference Example 50 was dissolved in THF (150 mL), and then 1.0 mol/L of a borane-THF complex (44.1 mL, 44.1 mmol) was added dropwise thereto under ice-cooling, followed by stirring at room temperature for 1 hour. The reaction mixture was again ice-cooled, and then water (15 mL), 34.5% aqueous hydrogen peroxide (10 mL) and 1.0 mol/L of an aqueous solution of sodium hydroxide (10 mL) were sequentially added dropwise, followed by stirring at room temperature for 1 hour. Water was added to the reaction mixture, followed by extraction with ethyl acetate (150 mL×3). The organic layer was washed with saturated brine, dried over anhydrous magnesium sulfate, and concentrated to yield a residue. The residue was purified by silica gel column chromatography (20 to 40% ethyl acetate/n-hexane) to obtain the title compound (5.19 g, 87%).

$^1$H NMR δ(ppm, CDCl$_3$): 5.18 (1H, m), 4.72-4.68 (2H, m), 3.79 (1H, br s), 3.49 (1H, m), 3.38 (3H, s), 3.33 (1H, m), 3.31 (3H, s), 3.13 (1H, dd, J=7.1 Hz, 16.1 Hz), 2.30 (1H, m), 2.00-1.17 (29H, m), 1.03 (3H, d, J=6.6 Hz), 0.84 (3H, s), 0.56 (3H, s).

Reference Example 52

(3S,5S,10R,13R,14R,17R)-3-Methoxymethoxy-17-[(S)-1-methoxypropan-2-yl]-10,13-dimethyl-2,3,4,5,9,11,12,13,14,15,16,17-dodecahydro-1H-cyclopenta[α]phenanthren-6(10H)-one (Compound P53)

Compound P52 (5.19 g, 12.8 mmol) obtained in Reference Example 51 was dissolved in dichloromethane (128 mL), and then N-methylmorpholine oxide (4.49 g, 38.3 mmol) and tetrapropylammonium perruthenate (225 mg, 0.64 mmol) were added thereto, followed by stirring at room temperature for 30 minutes. The reaction mixture was filtered by using celite, and the filtrate was concentrated, followed by purification by silica gel column chromatography (10 to 30% ethyl acetate/n-hexane) to obtain the tilte compound (4.2 g, 70%).

$^1$H NMR δ(ppm, CDCl$_3$): 5.72 (1H, m), 4.72-4.68 (2H, m), 3.53 (1H, m), 3.38 (3H, s), 3.32 (1H, m), 3.32 (3H, s), 3.16 (1H, dd, J=6.8 Hz, J=9.0 Hz), 2.30-1.30 (19H, m), 1.06 (3H, d, J=6.6 Hz), 0.87 (3H, s), 0.61 (3H, s).

Reference Example 53

(3S,5S,7S,8S,10R,13R,14R,17R)-7,8-Dihydroxy-3-methoxymethoxy-17-[(S)-1-methoxypropan-2-yl]-10,13-dimethyltetradecahydro-1H-cyclopenta[α]phenanthren-6(10H)-one (Compound P54)

Compound P53 (1.79 g, 4.09 mmol) obtained in Reference Example 52, sodium periodate (5.24 g, 24.5 mmol) and cerium chloride heptahydrate (1.52 g, 4.09 mmol) were dissolved in a mixed solvent of acetonitrile (200 mL)-ethyl acetate (200 mL)-water (67 mL), and then ruthenium trichloride (254 mg, 1.23 mmol) was added thereto, followed by stirring at 0° C. for 30 minutes. A saturated aqueous sodium thiosulfate solution was added to the reaction mixture, followed by extraction with ethyl acetate (500 mL×3). The organic layer was washed with saturated brine, dried over anhydrous magnesium sulfate, and concentrated to obtain the title compound (1.25 g, 65%).

$^1$H NMR δ(ppm, CDCl$_3$): 4.71-4.67 (2H, m), 4.26 (1H, br s), 3.55 (1H, m), 3.47 (1H, br s), 3.39-3.30 (7H, m), 3.11 (1H, dd, J=7.2 Hz, 9.0 Hz), 2.49-1.21 (20H, m), 1.03 (3H, d, J=6.6 Hz), 0.91 (3H, s), 0.84 (3H, s).

Reference Example 54

(1S,2R,5S)-5-Methoxymethoxy-2{(1R,3aR,7aR)-1-[(S)-1-methoxypropan-2-yl]-7a-methyl-4-oxooctahydro-1H-inden-5-yl}-2-methylcyclohexanecarboxylic acid (Compound P55)

Compound P54 (1.25 g, 2.65 mmol) obtained in Reference Example 53 was dissolved in pyridine (50 mL), and lead tetraacetate (2.35 g, 5.30 mmol) was added thereto, followed by stirring at 0° C. for 30 minutes. A saturated aqueous sodium thiosulfate solution was added to the reaction mixture, followed by extraction with ethyl acetate (50 mL×3). The organic layer was washed with saturated sodium thiosulfate, and dried over anhydrous magnesium sulfate, followed by purification by silica gel column chromatography (20 to 33% ethyl acetate/n-hexane) to obtain the title compound (1.47 g).

$^1$H NMR δ(ppm, CDCl$_3$): 4.67 (2H, s), 3.36 (3H, s), 3.31 (3H, s), 3.30 (1H, m), 3.13 (1H, dd, J=6.4 Hz, 15.6 Hz), 2.67 (1H, m), 2.58-1.35 (20H, m), 1.25 (3H, s), 1.04 (3H, d, J=6.2 Hz), 0.60 (3H, s).

Reference Example 55

3-(Methoxymethyloxy)-5,8-(1,2,3,4-tetrahydro-1,4-dioxophthalazin-2,3-diyl)-pregna-6-en-22-ol (Compound P56)

Compound P12 (23.9 g, 44.8 mmol) obtained in Reference Example 12 was dissolved in a mixed solvent of THF (450 mL) and water (50 mL), and cooled to 0° C., and then sodium borohydride (1.69 g, 44.8 mmol) was added thereto, followed by stirring at 30 minutes. A saturated aqueous ammonium chloride solution was added to the reaction mixture, followed by extraction with ethyl acetate (300 mL×3). The organic layer was washed with saturated brine, and dried over anhydrous magnesium sulfate. The residue obtained by concentration was purified by silica gel column chromatography (30 to 50% ethyl acetate/n-hexane) to obtain the title compound (20.8 g, 87%).

$^1$H NMR δ(ppm, CDCl$_3$): 8.17-8.13 (2H, m), 7.71-7.68 (2H, m), 6.66 (1H, d, J=8.1 Hz), 6.30 (1H, d, J=8.3 Hz), 4.70-4.65 (2H, m), 4.10-3.93 (2H, m), 3.66 (1H, dd, J=3.1 Hz, 10.6 Hz), 3.56 (1H, m), 3.38 (1H, m), 3.35 (3H, s), 2.14-1.23 (17H, m), 1.06 (3H, d, J=6.6 Hz), 1.03 (3H, s), 0.86 (3H, s).

Reference Example 56

3-(Methoxymethyloxy)-5,8-(1,2,3,4-tetrahydro-1,4-dioxophthalazin-2,3-diyl)-pregna-6-en-22-methallyl ether (Compound P57)

Compound P56 (9.67 g, 18.1 mmol) obtained in Reference Example 55, methallyl bromide (9.00 mL, 90.5 mmol) and tetrabutylammonium iodide (6.70 g, 18.1 mmol) were dissolved in DMF (60 mL), and sodium hydride (2.20 g, 54.3 mmol) was added thereto, followed by stirring at room temperature for 4 hours. The mixture was cooled to 0° C., and then a saturated aqueous ammonium chloride solution was added to the reaction mixture, followed by extraction with diethyl ether (100 mL×3). The organic layer was washed with saturated brine, and dried over anhydrous magnesium sulfate. The residue obtained by concentration was purified by silica gel column chromatography (20 to 40% ethyl acetate/n-hexane) to obtain the title compound (3.26 g, 93%).

$^1$H NMR δ(ppm, CDCl$_3$): 8.17-8.13 (2H, m), 7.72-7.68 (2H, m), 6.66 (1H, d, J=8.3 Hz), 6.27 (1H, d, J=8.4 Hz), 3.55 (1H, m), 3.35 (3H, s), 1.06 (3H, d, J=6.6 Hz), 1.03 (3H, s), 0.85 (3H, s).

Reference Example 57

3-(Methoxymethyloxy)-5,8-(1,2,3,4-tetrahydro-1,4-dioxophthalazin-2,3-diyl)-pregna-6-en-22-isobutyl ether (Compound P58)

Compound P57 (3.26 g, 5.06 mmol) obtained in Reference Example 56 was dissolved in ethyl acetate (20 mL), and then 10% palladium-carbon (326 mg) was added thereto, followed by stirring at room temperature for 9 hours under a hydrogen atmosphere. The catalyst was separated by filtration, and the filtrate was concentrated to obtain the title compound (2.99 g, 85%).

$^1$H NMR δ(ppm, CDCl$_3$): 8.15-8.12 (2H, m), 7.71-7.68 (2H, m), 6.66 (1H, d, J=7.9 Hz), 6.27 (1H, d, J=8.1 Hz), 4.70-4.67 (2H, m), 4.13-3.93 (2H, m), 3.55 (1H, m), 3.40-3.35 (5H, m), 3.20-3.05 (2H, m), 2.14-1.20 (17H, m), 1.04 (3H, d, J=5.3 Hz), 1.03 (3H, s), 0.90 (6H, dd, J=3.1 Hz, 6.8 Hz), 0.85 (3H, s).

Reference Example 58

(10R,13R,14R,17R)-17-(2-Isobutoxyethyl)-3-methoxymethoxy-10,13-dimethyl-2,3,4,9,11,12,13,14,15,16,17-dodecahydro-1H-cyclopenta[α]phenanthrene (Compound P59)

Compound P58 (2.99 g, 5.06 mmol) obtained in Reference Example 57 was treated with lithium aluminium hydride (960 mg, 25.3 mmol) in the same manner as Reference Example 13 to obtain the title compound (1.31 g, 60%).

$^1$H NMR δ(ppm, CDCl$_3$): 5.57 (1H, m), 5.28 (1H, m), 4.71 (2H, s), 3.53 (1H, m), 3.37 (1H, m), 3.38 (3H, s), 3.20 (1H, dd, J=6.6 Hz, 9.4 Hz), 3.11-3.07 (2H, m), 2.52 (1H, m), 2.37-1.20 (18H, m), 1.06 (3H, d, J=6.4 Hz), 0.94 (3H, s), 0.90 (6H, dd, J=2.8 Hz, 6.6 Hz), 0.63 (3H, s).

Reference Example 59

(5S,6S,10R,13R,14R,17R)-17-(2-Isobutoxyethyl)-3-methoxymethoxy-10,13-dimethyl-2,3,4,5,6,9,10,11,12,13,14,15,16,17-tetradecahydro-1H-cyclopenta[α]phenanthren-6-ol (Compound P60)

Compound P59 (1.31 g, 3.03 mmol) obtained in Reference Example 58 was treated with 1.0 mol/L of a borane-THF complex (9.0 mL, 9.0 mmol) in the same manner as Reference Example 2 to obtain the title compound (0.73 g, yield 54%).

$^1$H NMR δ(ppm, CDCl$_3$): 5.18 (1H, m), 4.74-4.68 (2H, m), 3.80 (1H, br s), 3.50 (1H, m), 3.38 (1H, m), 3.38 (3H, s), 3.19 (1H, dd, J=6.6 Hz, 9.2 Hz), 3.11-3.07 (2H, m), 2.33 (1H, m), 2.06-1.20 (20H, m), 1.04 (3H, d, J=6.4 Hz), 0.84 (3H, s) 0.89 (6H, dd, J=2.8 Hz, 6.8 Hz), 0.56 (3H, s).

Reference Example 60

(5R,10R,13R,14R,17R)-17-(2-Isobutoxyethyl)-3-methoxymethoxy-10,13-dimethyl-2,3,4,5,9,11,12,13,14,15,16,17-dodecahydro-1H-cyclopenta[α]phenanthren-6(10H)-one (Compound P61)

Compound P60 (2.63 g, 5.86 mmol) obtained in Reference Example 59 was treated with N-methylmorpholine oxide (2.10 g, 17.6 mmol) and tetrapropylammonium perruthenate (103 mg, 0.293 mmol) in the same manner as Reference Example 4 to obtain the title compound (2.6 g, 100%).

$^1$H NMR δ(ppm, CDCl$_3$): 5.72 (1H, s), 4.72-4.68 (2H, m), 3.52 (1H, m), 3.38 (3H, s), 3.39-3.06 (4H, m), 2.29-1.20 (22H, m), 1.05 (3H, d, J=6.6 Hz), 0.91-0.89 (6H, m), 0.87 (3H, s), 0.62 (3H, s).

Reference Example 61

(5S,7S,8S,10R,13R,14R,17R)-7,8-Dihydroxy-17-(2-isobutyloxyethyl)-3-methoxymethoxy-10,13-dimethyl tetradecahydro-1H-cyclopenta[α]phenanthren-6(10H)-one (Compound P62)

Compound P61 (2.62 g, 5.86 mmol) obtained in Reference Example 60 was treated with sodium periodate (7.50 g, 35.2 mmol), cerium chloride heptahydrate (2.18 g, 5.86 mmol) and ruthenium chloride (365 mg, 1.76 mmol) in the same manner as Reference Example 5 to obtain the title compound (2.03 g, 72%).

$^1$H NMR δ(ppm, CDCl$_3$): 4.73-4.67 (2H, m), 4.27 (1H, s), 3.71-3.04 (8H, m), 2.47-2.37 (2H, m), 2.05-0.83 (35H, m).

Reference Example 62

(1S,2R)-2-[(1R,3aR,7aR)-1-(2-Isobutoxyethyl)-7a-methyl-4-oxooctahydro-1H-inden-5-yl]-5-methoxymethoxy-2-methylcyclohexanecarboxylic acid (Compound P63)

Compound P62 (2.03 g) obtained in Reference Example 61 was treated with lead tetraacetate (3.70 g, 8.45 mmol) in the same manner as Reference Example 39 to obtain a crude product (2.34 g) of the title compound.

Reference Example 63

(3S,5S,6S,10R,13R,14R)-3-Methoxymethoxy-10,13-dimethyl-17-[(S)-1-triisopropylsilyloxy propan-2-yl]-2,3,4,5,6,9,10,11,12,13,14,15,16,17-tetradecahydro-1H-cyclopenta[α]phenanthren-6-ol (Compound P82)

Compound P13 (3.66 g, 9.78 mmol) obtained in Reference Example 13 was dissolved in DMF (90 mL), and imidazole (1.99 g, 29.3 mmol), triisopropylsilyl chloride (4.20 mL, 19.6 mmol) and catalytic amount of 4-dimethylamino pyridine were added thereto, followed by stirring at room temperature for 12 hours. Water was added to the reaction mixture, followed by extraction with diethyl ether (100 mL×3). The organic layer was washed with saturated brine, dried over anhydrous magnesium sulfate, and concentrated. The resulting residue (5.3 g) was dissolved in THF (100 mL), and 1.0 mol/L of a borane-THF complex (30.0 mL, 30.0 mmol) was added dropwise thereto under ice-cooling, followed by stirring at room temperature for 1 hour. The reaction mixture was again ice-cooled, and then water (15 mL), 34.5% aqueous hydrogen peroxide (10.0 mL) and 1.0 mol/L of an aqueous solution of sodium hydroxide (10 mL) were sequentially added dropwise, followed by stirring at room temperature for 1 hour. Water was added to the reaction mixture, followed by extraction with ethyl acetate (100 mL×3). The organic layer was washed with saturated sodium thiosulfate and saturated brine, dried over anhydrous magnesium sulfate, and concentrated to yield a residue. The residue was purified by silica gel column chromatography (20 to 40% ethyl acetate/n-hexane) to obtain the title compound (2.63 g, 49% (2 steps)).

$^1$H NMR δ(ppm, CDCl$_3$): 5.18 (1H, m), 4.72-4.67 (2H, m), 3.80 (1H, br s), 3.67 (1H, dd, J=3.3 Hz, 9.4 Hz), 3.50 (1H, m), 3.38 (1H, m), 3.38 (3H, s), 2.31 (1H, m), 2.04 (1H, m), 1.90-1.19 (18H, m) 1.08-1.03 (24H, m), 0.85 (3H, s), 0.56 (3H, s).

Reference Example 64

(3S,5S,10R,13R,14R)-3-Methoxymethoxy-10,13-dimethyl-17-triisopropylsilyloxy propan-2-yl-2,3,4,5,9,11,12,13,14,15,16,17-dodecahydro-1H-cyclopenta[α]phenanthren-6(10H)-one (Compound P83)

Compound P82 (2.63 g, 4.79 mmol) obtained in Reference Example 63 was treated with N-methylmorpholine oxide (3.36 g, 18.7 mmol) and tetrapropylammonium perruthenate (84.0 mg, 0.239 mmol) in the same manner as Reference Example 4 to obtain the title compound (2.50 g, 93%).

$^1$H NMR δ(ppm, CDCl$_3$): 5.73 (1H, m), 4.72-4.67 (2H, m), 3.67 (1H, dd, J=3.1 Hz, 9.4 Hz), 3.53 (1H, m), 3.43 (1H, dd, J=6.4 Hz, 9.4 Hz), 3.38 (3H, s) 2.28 (1H, m), 2.20-1.23 (18H, m), 1.07-1.05 (24H, m), 0.87 (3H, s), 0.62 (3H, s).

Reference Example 65

(1S,2R,5S)-5-Methoxymethoxy-2-methyl-2-{(3aR,7aR)-7a-methyl-4-oxo-1-[(S)-1-triisopropylsilyloxy propan-2-yl]octahydro-1H-inden-5-yl}cyclohexanecarboxylic acid (Compound P84)

Compound P83 (812 mg, 1.485 mmol) obtained in Reference Example 64 was treated with sodium periodate (1.905 g, 8.908 mmol), cerium chloride heptahydrate (553 mg, 1.49 mmol) and ruthenium trichloride (92.0 mg, 0.446 mmol) in the same manner as Reference Example 5, followed by treating the resulting crude product with lead tetraacetate (984 mg, 2.00 mmol) to obtain the title compound (296 mg, 35% (2 steps)).

$^1$H NMR δ(ppm, CDCl$_3$): 4.67 (2H, s), 3.64 (1H, dd, J=2.8 Hz, 9.7 Hz), 3.47-3.36 (5H, m), 2.68 (1H, m), 2.57-1.35 (19H, m), 1.25 (3H, s), 1.14-0.97 (24H, m), 0.60 (3H, s).

Reference Example 66

(3aR,5aS,7S,9aS,11aR)-7-Methoxymethoxy-9a,11a-dimethyl-1-[(5)-1-triisopropylsilyloxy propan-2-yl]-1,2,3,3a,5a,6,7,8,9,9a,11,11a-dodecahydrobenzo[c]cyclopenta[h]chromen-5(10H)-one (Compound P85)

Compound P84 (295.7 mg, 0.5216 mmol) obtained in Reference Example 65 was dissolved in dichloromethane (5 mL), and triethylamine (0.73 mL, 5.22 mmol) and thionyl chloride (76 µL, 1.04 mmol) were added thereto at 0° C., followed by stirring for 10 minutes. Water was added to the reaction mixture, followed by extraction with chloroform (10 mL×3). The organic layer was washed with saturated brine, and dried over anhydrous magnesium sulfate. The residue obtained by concentration was purified by silica gel column chromatography (25% ethyl acetate/n-hexane) to obtain the title compound (125 mg, 47%).

$^1$H NMR δ(ppm, CDCl$_3$): 4.71-4.68 (2H, m), 3.67 (1H, dd, J=3.3 Hz, 9.5 Hz), 3.52 (1H, m), 3.41-3.36 (4H, m), 2.36-1.23 (18H, m), 1.14-0.97 (24H, m), 0.97 (3H, s), 0.69 (3H, s).

Reference Example 67

(10R,13R,14R)-3-Methoxymethoxy-10,13-dimethyl-17-[(S)-1-(2-methylallyloxy)propan-2-yl]-2,3,4,9,10,11,12,13,14,15,16,17-dodecahydro-1H-cyclopenta[α]phenanthrene (Compound P64)

Compound P57 (4.41 g, 7.49 mmol) obtained in Reference Example 56 was treated with lithium aluminium hydride (1.42 g, 37.5 mmol) in the same manner as Reference Example 13 to obtain the title compound (1.73 g, 54%).

$^1$H NMR δ(ppm, CDCl$_3$): 5.57 (1H, m), 5.38 (1H, m), 4.95 (1H, m), 4.87 (1H, m), 4.71 (2H, s), 3.88-3.83 (2H, m), 3.53 (1H, m), 3.37 (1H, m), 3.38 (3H, s), 3.13 (1H, dd, J=7.5 Hz, 9.0 Hz), 2.52 (1H, m), 2.36-2.32 (2H, m), 2.10-1.19 (18H, m), 1.08 (3H, d, J=6.6 Hz), 0.94 (3H, s), 0.63 (3H, s).

Reference Example 68

(5S,6S,10R,13R,14R)-17-[(2S)-1-(3-Hydroxy-2-methylpropoxy)propan-2-yl]-3-methoxymethoxy-10,13-dimethyl-2,3,4,5,6,9,10,11,12,13,14,15,16,17-tetradecahydro-1H-cyclopenta[α]phenanthren-6-ol (Compound P65)

Compound P64 (1.73 g, 4.03 mmol) obtained in Reference Example 67 was treated with 1.0 mol/L of a borane-THF complex (12 mL, 12 mmol) in the same manner as Reference Example 2 to obtain the title compound (960 mg, 51%).

$^1$H NMR δ(ppm, CDCl$_3$): 5.18 (1H, s), 4.73-4.67 (2H, m), 3.80 (1H, m), 3.60-3.19 (8H, m), 3.38 (3H, s), 2.86 (1H, m), 2.31 (1H, m), 2.08-2.03 (2H, m), 1.89-1.13 (17H, m), 1.03 (3H, d, J=6.6 Hz), 0.87-0.84 (3H, m), 0.84 (3H, s), 0.55 (3H, s).

Reference Example 69

(5S,10R,13R,14R)-17-[(2S)-1-(3-Hydroxy-2-methylpropoxy)propan-2-yl]-3-methoxymethoxy-10,13-dimethyl-2,3,4,5,9,11,12,13,14,15,16,17-dodecahydro-1H-cyclopenta[α]phenanthren-6(10H)-one (Compound P66)

Compound P65 (960 mg, 7.06 mmol) obtained in Reference Example 68 was dissolved in chloroform (80 mL), and manganese dioxide (17.9 g, 206 mmol) was added, followed by stirring at room temperature for 12 hours, and further stirring at 70° C. for 1 hour. The reaction mixture was filtered through a celite to obtain the title compound (955 mg, 100%).

$^1$H NMR δ(ppm, CDCl$_3$): 5.72 (1H, m), 4.74-4.65 (2H, m), 3.64-3.18 (7H, m), 3.38 (3H, s), 2.30-1.21 (16H, m), 1.05 (3H, d, J=6.6 Hz), 0.90-0.85 (6H, m), 0.61 (3H, s).

Reference Example 70

(5S,10R,13R,14R)-3-Methoxymethoxy-10,13-dimethyl-17-[(2S)-1-(2-methyl-3-triisopropylsilyloxypropoxy)propan-2-yl]-2,3,4,5,9,11,12,13,14,15,16,17-dodecahydro-1H-cyclopenta[α]phenanthren-6(10H)-one (Compound P67)

Compound P66 (955 mg, 2.06 mmol) obtained in Reference Example 69 was treated with triisopropylsilyl chloride (2.20 mL, 10.3 mmol) in the same manner as Reference Example 63 to obtain a crude product of the title compound (2.94 g).

Reference Example 71

(5S,7S,8S,10R,13R,14R)-7,8-Dihydroxy-3-methoxymethoxy-10,13-dimethyl-17-[(2S)-1-(2-methyl-3-triisopropylsilyloxypropoxy)propan-2-yl]tetradecahydro-1H-cyclopenta[α]phenanthren-6(10H)-one (Compound P68)

A crude product (2.94 g) of compound P67 obtained in Reference Example 70 was treated with ruthenium trichloride (126 mg, 0.620 mmol), sodium periodate (2.65 g, 12.4 mmol) and cerium chloride heptahydrate (770 mg, 2.06 mmol) in the same manner as Reference Example 5 to obtain the title compound (608 mg, 45% (2 steps)).

$^1$H NMR δ(ppm, CDCl$_3$): 4.74-4.67 (2H, m), 4.27 (1H, br s), 3.68-3.07 (9H, m), 3.38 (3H, s), 2.47-1.21 (19H, m), 1.09-1.01 (27H, m), 0.93 (3H, d, J=4.4 Hz), 0.85 (3H, s).

Reference Example 72

(1S,2R)-5-Methoxymethoxy-2-methyl-2-{(1R,3aR,7aR)-7a-methyl-1-[(2S)-1-(2-methyl-3-triisopropylsilyloxypropoxy)propan-2-yl}-4-oxooctahydro-1H-inden-5-yl]cycicohexanecarboxylic acid (Compound P69)

Compound P68 (608 mg, 0.93 mmol) obtained in Reference Example 71 was treated with lead tetraacetate (826 mg, 1.86 mmol) in the same manner as Reference Example 39 to obtain the title compound (370 mg, 60%).

$^1$H NMR δ(ppm, CDCl$_3$): 4.67 (2H, s), 3.63-3.08 (7H, m), 3.36 (3H, s), 2.71-1.18 (21H, m), 1.25 (3H, s), 1.06-1.04 (24H, m), 0.92 (3H, d, J=6.6 Hz), 0.60 (3H, s).

Reference Example 73

(1R,3aR,5aS,9aS,11aR)-7-Methoxymethoxy-9a,11a-dimethyl-1-[(2S)-1-(2-methyl-3-triisopropylsilyloxypropoxy)propan-2-yl]-1,2,3,3a,5a,6,7,8,9,9a,11,11a-dodecahydrobenzo[c]cyclopenta[h]chromen-5(10H)-one (Compound P70)

Compound P69 (23.7 mg, 0.0370 mmol) obtained in Reference Example 72 was treated with thionyl chloride (10.0 μL, 0.14 mmol) in the same manner as Reference Example 40 to obtain the title compound (13.6 mg, 59%).

$^1$H NMR δ(ppm, CDCl$_3$): 4.70 (2H, m), 3.63-3.11 (7H, m), 3.38 (3H, s), 2.37-1.25 (19H, m), 1.10-1.02 (24H, m), 0.97 (3H, s), 0.92 (3H, d, J=6.8 Hz), 0.69 (3H, s).

Reference Example 74

3-(Methoxymethyloxy)-5,8-(1,2,3,4-tetrahydro-1,4-dioxophthalazin-2,3-diyl)-chol-6,22-diene-24-propionic acid (Compound P71)

In THF (50 mL), 4-(carboxybutyl)triphenylphosphonium bromide (22.5 g, 50.7 mmol) was suspended, followed by addition of potassium tert-butoxide (11.4 g, 101 mmol). After the solution turned orange color, compound P12 (4.20 g, 7.90 mmol) obtained in Reference Example 12 was added, followed by stirring at room temperature for 30 minutes. The mixture was ice-cooled, and then 1.0 mol/L of an aqueous solution of hydrochloric acid was added, followed by extraction with ethyl acetate (100 mL×3). The organic layer was washed with saturated brine, and dried over anhydrous magnesium sulfate. The residue obtained by concentration was purified by silica gel column chromatography (33 to 50% ethyl acetate/n-hexane) to obtain the title compound (3.84 g, 80%).

$^1$H NMR δ(ppm, CDCl$_3$): 8.16-8.10 (2H, m), 7.74-7.68 (2H, m), 6.66 (1H, d, J=8.1 Hz), 6.27 (1H, d, J=8.3 Hz), 5.22-5.16 (2H, m), 4.72-4.68 (2H, m), 4.11-3.92 (2H, m), 3.55 (1H, m), 3.35 (3H, s), 2.39-1.33 (21H, m), 1.03 (3H, s), 0.97 (3H, d, J=6.6 Hz), 0.82 (3H, s).

Reference Example 75

3-(Methoxymethyloxy)-5,8-(1,2,3,4-tetrahydro-1,4-dioxophthalazin-2,3-diyl)-chol-6-ene-24-propionic acid (Compound P72)

Compound P71 (3.93 g, 6.37 mmol) obtained in Reference Example 74 was dissolved in ethyl acetate (227 mL). To the resulting solution, 10% palladium-carbon (390 mg) was added, followed by stirring at room temperature for 15 hours under a hydrogen atmosphere. The catalyst was separated by filtration, and then the filtrate was concentrated to obtain the title compound (3.7 g).

Reference Example 76

(7R)-7-[(3S,10R,13R,14R,17R)-3-Methoxymethoxy-10,13-dimethyl-2,3,4,9,10,11,12,13,14,15,16,17-dodecahydro-1H-cyclopenta[α]phenanthren-17-yl]octan-1-ol (Compound P73)

Compound P72 (3.7 g) obtained in Reference Example 75 was treated with lithium aluminium hydride (1.10 g, 29.3 mmol) in the same manner as Reference Example 13 to obtain the title compound (1.4 g, 54% (2 steps)).

$^1$H NMR δ(ppm, CDCl$_3$): 5.56 (1H, m), 5.39 (1H, m), 4.74-4.68 (2H, m), 3.70-3.60 (2H, m), 3.54 (1H, m), 3.38 (3H, s), 2.54-2.32 (3H, m), 2.05-1.19 (26H, m), 0.95-0.93 (6H, m), 0.62 (3H, s).

Reference Example 77

(7R)-7-[(3S,10R,13R,14R,17R)-3-Methoxymethoxy-10,13-dimethyl-2,3,4,9,10,11,12,13,14,15,16,17-dodecahydro-1H-cyclopenta[α]phenanthren-17-yl]octyl acetate (Compound P74)

Compound P73 (800 mg, 1.80 mmol) obtained in Reference Example 76 was dissolved in pyridine (5 mL) and acetic anhydride (4 mL), followed by stirring at room temperature for 3.5 hours. The resulting mixture was concentrated to obtain a crude product (841 mg) of the title compound.

Reference Example 78

(7R)-7-[(3S,5S,6S,10R,13R,14R,17R)-6-Hydroxy-3-methoxymethoxy-10,13-dimethyl-2,3,4,5,6,9,10,11,12,13,14,15,16,17-tetradecahydro-1H-cyclopenta[α]phenanthren-17-yl]octyl acetate (Compound P75)

Compound P74 (841 mg) obtained in Reference Example 77 was treated with 1.0 mol/L of a borane-THF complex (8.6 mL, 8.6 mmol) in the same manner as Reference Example 2 to obtain the title compound (241 mg, 48% (2 steps)).
$^1$H NMR δ(ppm, CDCl$_3$): 5.34 (0.2H, br s), 5.18 (0.8H, br s), 4.75-4.68 (2H, m), 4.05 (2H, t, J=6.6 Hz), 3.81 (1H, m), 3.50 (1H, m), 3.38 (3H, s), 2.40-1.08 (33H, m), 0.92 (3H, d, J=6.2 Hz), 0.85 (3H, s), 0.54 (3H, s).

Reference Example 79

(7R)-7-[(3S,5S,10R,13R,14R,17R)-3-Methoxymethoxy-10,13-dimethyl-6-oxo-2,3,4,5,6,9,10,11,12,13,14,15,16,17-tetradecahydro-1H-cyclopenta[α]phenanthren-17-yl]octyl acetate (Compound P76)

Compound P75 (240.7 mg, 0.4769 mmol) obtained in Reference Example 78 was treated with N-methylmorpholine oxide (83.8 mg, 0.715 mmol) and catalytic amount of tetrapropylammonium perruthenate in the same manner as Reference Example 4 to obtain the title compound (186 mg, 78%).
$^1$H NMR δ(ppm, CDCl$_3$): 5.73 (1H, m), 4.74-4.68 (2H, m), 4.06 (2H, t, J=6.6 Hz), 3.53 (1H, m), 3.39 (3H, s), 2.31-1.14 (32H, m), 0.94 (3H, d, J=6.1 Hz), 0.87 (3H, s), 0.60 (3H, s).

Reference Example 80

(7R)-7-[(3S,5S,7S,8S,10R,13R,14R,17R)-7,8-Dihydroxy-3-methoxymethoxy-10,13-dimethyl-6-oxohexadecahydro-1H-cyclopenta[α]phenanthren-17-yl]octyl acetate (Compound P77)

Compound P76 (32.9 mg, 0.0654 mmol) obtained in Reference Example 79 was treated with cerium chloride heptahydrate (24.0 mg, 0.0654 mmol), sodium periodate (84.0 mg, 0.392 mmol) and catalytic amount of ruthenium chloride in the same manner as Reference Example 5 to obtain the title compound (28 mg, 75%).
$^1$H NMR δ(ppm, CDCl$_3$): 4.75-4.65 (2H, m), 4.26 (1H, br s), 4.04 (2H, t, J=6.6 Hz), 3.56 (1H, m), 3.47 (1H, s), 3.37-3.32 (1H, m), 3.36 (3H, s), 2.52-2.40 (1H, m), 2.03 (3H, s), 2.14-1.10 (27H, m), 0.92-0.89 (6H, m), 0.83 (3H, s).

Reference Example 81

2-[1-(8-Acetoxyoctan-2-yl)-7a-methyl-4-oxooctahydro-1H-inden-5-yl]-5-methoxymethoxy-2-methylcyclohexane carboxylic acid (Compound P78)

Compound P77 (28.8 mg, 0.0537 mmol) obtained in Reference Example 80 was treated with lead tetraacetate (48.0 mg, 0.107 mmol) in the same manner as Reference Example 39 to obtain the title compound (17.8 mg, 60%).
$^1$H NMR δ(ppm, CDCl$_3$): 4.73 (2H, s), 4.05 (2H, t, J=6.6 Hz), 3.45 (1H, m), 3.37 (3H, s), 2.67-0.83 (39H, m), 0.59 (3H, s).

Reference Example 82

(1S,2R,5S)-2-{(1R,3aR,7aR)-1-[(R)-8-Hydroxyoctan-2-yl]-7a-methyl-4-oxooctahydro-1H-inden-5-yl}-5-methoxymethoxy-2-methylcyclohexanecarboxylic acid (Compound P79)

Compound P78 (35.7 mg, 0.079 mmol) obtained in Reference Example 81 was dissolved in methanol (3 mL), and then catalytic amount of potassium carbonate was added thereto, followed by stirring at room temperature for 5 hours. Water was added to the reaction mixture, followed by extraction with ethyl acetate (10 mL×3). The organic layer was dried over anhydrous magnesium sulfate, and concentrated to yield a residue. The residue was purified by silica gel column chromatography (50% ethyl acetate/n-hexane) to obtain the title compound (19.4 mg, 51%).
$^1$H NMR δ(ppm, CDCl$_3$): 4.71 (2H, s), 3.64 (2H, t, J=6.6 Hz), 3.45 (1H, m), 3.36 (3H, s), 2.67-0.81 (37H, m), 0.59 (3H, s).

Reference Example 83

(1S,2R,5S)-2-{(1R,3aR,7aR)-1-[(R)-8-tert-Butyldimethylsiloxyoctan-2-yl]-7a-methyl-4-oxooctahydro-1H-inden-5-yl}-5-methoxymethoxy-2-methylcyclohexanecarboxylic acid (Compound P80)

Compound P79 (19.4 mg, 0.0400 mmol) obtained in Reference Example 82 was dissolved in DMF (3 mL), and imidazole (54.0 mg, 0.80 mmol) and tert-butyldimethylsilyl chloride (60.0 mg, 0.40 mmol) were added thereto, followed by stirring at room temperature for 3.5 hours. Water was added to the reaction mixture, followed by extraction with diethyl ether (10 mL×3). The organic layer was washed with saturated brine, dried over anhydrous magnesium sulfate, and concentrated to yield a residue. The residue was purified by silica gel column chromatography (33% ethyl acetate/n-hexane) to obtain the title compound (11.4 mg, 48%).
$^1$H NMR δ(ppm, CDCl$_3$): 4.62 (2H, s), 3.55 (2H, t, J=6.6 Hz), 3.32 (3H, s), 2.60-1.05 (31H, m), 0.86-0.85 (21H, m), 0.54 (3H, s).

Reference Example 84

(1R,3aR,5aR,7S,9aS,11aR)-1-[(R)-8-tert-Butyldimethylsiloxyoctan-2-yl-7-methoxymethoxy]-9a,11a-dimethyl-1,2,3,3a,5a,6,7,8,9,9a,11,11a-dodecahydrobenzo[c]cyclopenta[h]chromen-5(10H)-one (Compound P81)

Compound P80 (11.4 mg; 0.0190 mmol) obtained in Reference Example 83 was treated with thionyl chloride (7.0 μL, 0.095 mmol) in the same manner as Reference Example 40 to obtain the title compound (0.9 mg, 8%).
$^1$H NMR δ(ppm, CDCl$_3$): 4.75-4.65 (2H, m), 3.62-3.50 (3H, m), 3.38 (3H, s), 2.37-1.20 (28H, m), 0.94-0.90 (15H, m), 0.67 (3H, s), 0.05 (6H, s).

Reference Example 85

7-Oxa-ergosta-8(9),24(28)-dien-6-on-3-ol

As the first seed medium and second seed medium, a medium comprising glucose (20 g/L), mashed potatoes (30 g/L) and dry yeast extract (5 g/L) (pH 6.5) was used, and as the main fermentation medium, a medium comprising sucrose (30 g/L), soluble starch (20 g/L), corn steep liquor (CSL) (30 g/L) and calcium carbonate (5 g/L) (pH 5.0) was used. A piece of agar containing *Penicillium* sp. CND1007 (FERM BP-10917) was inoculated into the first seed medium (10 mL) which had been added into a 70 mL capacity test tube, followed by shaking culturing at 28° C. for 72 hours. Next, 25 mL per flask of the first seed culture liquid was inoculated into the second seed medium (475 mL) which had been added into each of 2 L capacity conical flasks, followed by shaking for 72 hours in the same manner. Subsequently, 900 mL per fermenter of the second seed culture liquid was inoculated into the main fermentation medium (about 54 L) which had been dispensed into three 30 L capacity jar fermenters, followed by agitation culturing (the number of revolutions 250 rpm) at 25° C. for 8 days. Additionally, 25 mL per flask of the second seed culture liquid was inoculated into the main fermentation medium (about 10 L) which had been dispensed into 20 conical flasks each having 2 L capacity, followed by agitation culturing (the number of revolutions 220 rpm) at 25° C. for 8 days.

A filter aid (Radiolite #600, manufactured by Showa Chemical Industry) was added at a ratio of 10% by weight to the thus obtained fermentation culture liquid (64 L) and then the culture filtrate and cells were separated by suction filtration. The separated cells were mixed with 15 L of methanol, followed by extraction twice at room temperature. The extract (30 L) was concentrated to 10 L under reduced pressure and applied to a column filled with 2 L of Diaion HP 20 (manufactured by Mitsubishi Chemical Corp.) to adsorb the desired compound. After washing with water, 40% methanol and 70% methanol, the desired compound was eluted with 100% methanol and 30% acetone/methanol. The eluate (6 L) was concentrated to 1 L under reduced pressure and then extracted three times with chloroform (1 L). The residue (15 g) obtained by concentrating the extract under reduced pressure was applied to a column filled with 500 mL of silica gel and eluted stepwise using n-hexane, ethyl acetate, methanol and a mixed solvent thereof. Components contained in each eluate was detected by thin layer chromatography, and eluates containing the same component were combined to obtain fractions of 20 to 40% ethyl acetate/n-hexane elution fraction (fraction 1), 60% ethyl acetate/n-hexane elution fraction (fraction 2), 60 to 80% ethyl acetate/n-hexane elution fraction (fraction 3), 80% ethyl acetate/n-hexane to ethyl acetate elution fraction (fraction 4), ethyl acetate to 25% methanol/ethyl acetate elution fraction (fraction 5) and 25% methanol/ethyl acetate elution fraction (fraction 6).

The fraction 2 (300 mg) was applied to a column filled with 20 mL of silica gel, followed by elution with n-hexane and ethyl acetate. Fractions containing the compounds of interest were collected and concentrated, and the thus obtained residue (200 mg) was separated and purified by fractional high performance liquid chromatography [column SunFire™ Prep C18 OBD 10 μm, ϕ19×250 mm, column temperature 40° C., flow rate 10 mL/min, stepwise elution with 85 to 100% methanol aqueous solution] to obtain 7-oxa-ergosta-8(9),24(28)-dien-6-on-3-ol (44.6 mg).

Example 1

(S)-7-Oxa-8-cholesten-3,6-dione (Compound 1)

Compound P5 (167 mg, 0.399 mmol) obtained in Reference Example 5 was dissolved in dichloromethane (4.0 mL), and triethylamine (166 μL, 1.20 mmol) and thionyl chloride (43.7 μL, 0.598 mmol) were added thereto at room temperature, followed by stirring for 20 minutes. A saturated aqueous sodium bicarbonate solution was added to the reaction mixture, followed by extraction with chloroform twice. The organic layer was washed with saturated brine, dried over anhydrous magnesium sulfate, and concentrated under reduced pressure to yield a residue. The residue was purified by silica gel column chromatography to obtain the title compound (133 mg, 83%).

$^1$H NMR (CDCl$_3$) δ(ppm): 0.71 (s, 3H), 0.86 (d, J=7.0 Hz, 3H), 0.88 (d, J=7.0 Hz, 3H), 0.94 (d, J=6.6 Hz, 3H), 0.99-2.63 (m, 26H), 2.70-2.82 (m, 2H).

Example 2

(3S,5S)-3-Hydroxy-7-oxa-8-cholesten-6-one (Compound 2)

Compound 1 (400 mg, 0.999 mmol) obtained in Example 1 was dissolved in a mixed solvent of methanol (6.0 mL) and dichloromethane (4.0 mL), and sodium borohydride (37.8 mg, 0.999 mmol) was added thereto at 0° C., followed by stirring at 20 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain the title compound (363 mg, 90%).

$^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.3 Hz, 3H), 0.97 (s, 3H), 1.00-2.43 (m, 25H), 3.57-3.69 (m, 1H).

Example 3

(S)-3-Hydroxyimino-7-oxa-8-cholesten-6-one (Compound 3)

Compound 1 (172 mg, 0.429 mmol) obtained in Example 1 was dissolved in ethanol (4.0 mL), and hydroxyamine hydrochloride (89.5 mg, 1.29 mmol) and triethylamine (178 μL, 1.29 mmol) were added thereto at room temperature, followed by stirring for 20 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain the title compound (160 mg, 90%) as a mixture of E-form and Z-form.

ESI-MS: m/z 416 [M+H]$^+$, $^1$H NMR (CDCl$_3$) δ(ppm): 0.69 (s, 3H), 0.86 (d, J=6.4 Hz, 3H), 0.88 (d, J=6.4 Hz, 3H), 0.93 (d, J=6.3 Hz, 3H), 0.98-2.80 (m, 27H), 3.30-3.40 (m, 0.5H), 3.68-3.78 (m, 0.5H), 6.77 (s, 0.5H), 6.81 (s, 0.5H).

Example 4

(S)-7-Oxa-1,8-cholestadien-3,6-dione (Compound 4) and 7-oxa-4,8-cholestadien-3,6-dione (Compound 5)

Compound 1 (207 mg, 0.516 mmol) obtained in Example 1 was dissolved in THF (5.0 mL), and chlorotrimethylsilane (197 μL, 1.55 mmol) and 1.0 mol/L of a lithium bis(trimethylsilylamide)/THF solution (723 μL, 0.723 mmol) were added thereto at 0° C., followed by stirring for 1 hour. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure. The resulting resiude was suspended in acetonitrile (20 mL), and then palladium acetate (232 mg, 1.03 mmol) was added thereto, followed by stirring at room temperature for 3.5 hours. The reaction mixture was filtrated through a celite, and the filtrate was concentrated under reduced pressure to yield a residue. The residue was purified by silica gel column chromatography to obtain compound 4 (98.2 mg, 48%) and compound 5 (47.3 mg, 23%).

Compound 4; ESI-MS: m/z 399 [M+H]$^+$, $^1$H NMR (CDCl$_3$) δ(ppm): 0.72 (s, 3H), 0.86 (d, J=6.6 Hz, 3H), 0.88 (d, J=6.6 Hz, 3H), 0.95 (d, J=6.6 Hz, 3H), 1.00-1.83 (m, 16H), 1.94-2.05 (m, 1H), 2.10-2.19 (m, 1H), 2.31-2.43 (m, 3H), 2.66 (dd, J=13.8, 18.0 Hz, 1H), 2.89 (dd, J=4.4, 18.0 Hz, 1H), 3.16 (dd, J=4.4, 13.8 Hz, 1H), 6.00 (d, J=9.9 Hz, 1H), 7.08 (d, J=9.9 Hz, 1H).

Compound 5; ESI-MS: m/z 399 [M+H]$^+$, $^1$H NMR (CDCl$_3$) δ(ppm): 0.74 (s, 3H), 0.86 (d, J=6.6 Hz, 3H), 0.88 (d, J=6.6 Hz, 3H), 0.94 (d, J=6.6 Hz, 3H), 0.98-1.60 (m, 15H), 1.76-1.87 (m, 1H), 1.95-2.13 (m, 4H), 2.17-2.26 (m, 2H), 2.32-2.40 (m, 1H), 2.52-2.61 (m, 2H), 6.72 (s, 1H).

Example 5

(1R,2R,5S)-1,2-Epoxy-7-oxa-8-cholesten-3,6-dione (Compound 6)

Compound 4 (11.0 mg, 0.0276 mmol) obtained in Example 4 was dissolved in THF (1.0 mL), and 30% aqueous hydrogen peroxide (8.5 µL, 0.0828 mmol) and 10% aqueous sodium hydroxide solution (20.1 µL, 0.0551 mmol) were added thereto at 0° C., followed by stirring at room temperature for 40 minutes. A saturated aqueous ammonium chloride solution and a saturated aqueous sodium thiosulfate solution were added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (4.0 mg, 35%).

ESI-MS: m/z 415 [M+H]$^+$, $^1$H NMR (CDCl$_3$) δ(ppm): 0.72 (s, 3H), 0.86 (d, J=6.7 Hz, 3H), 0.88 (d, J=6.7 Hz, 3H), 0.96 (d, J=6.6 Hz, 3H), 0.98-1.60 (m, 15H), 1.72-1.82 (m, 1H), 1.94-2.05 (m, 1H), 2.10-2.19 (m, 1H), 2.28-2.57 (m, 4H), 2.74 (dd, J=6.3, 19.8 Hz, 1H), 3.25 (dd, J=6.3, 12.6 Hz, 1H), 3.36 (d, J=4.3 Hz, 1H), 3.62 (d, J=4.3 Hz, 1H).

Example 6

(S)-3-Methylen-7-oxa-8-cholesten-6-one (Compound 7) and (R)-3-methylen-7-oxa-8-cholesten-6-one (Compound 9)

Methyl triphenylphosphonium bromide (58.0 mg, 0.162 mmol) was suspended in THF (1.0 mL), followed by adding 1.0 mol/L of a lithium bis(trimethylsilylamide)/THF solution (225 µL, 0.225 mmol) at 0° C. Subsequently, a THF solution (0.5 mL) of compound 1 (50.0 mg, 0.125 mmol) obtained in Example 1 was added thereto, followed by stirring at room temperature for 1 hour. Water was added to the reaction mixture, followed by extraction with ethyl acetate twice. The organic layer was washed with saturated brine, dried over anhydrous sodium sulfate, and concentrated under reduced pressure to yield a residue. The residue was purified by preparative thin layer chromatography to obtain compound 7 (10.3 mg, 21%) and compound 9 (13.1 mg, 26%).

Compound 7; ESI-MS: m/z 399 [M+H]$^+$, $^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.6 Hz, 3H), 0.97-1.54 (m, 16H), 1.69-1.78 (m, 2H), 1.90-2.44 (m, 9H), 2.59-2.65 (m, 1H), 4.71-4.76 (m, 2H).

Compound 9; ESI-MS: m/z 399 [M+H]$^+$, NMR (CDCl$_3$) δ(ppm): 0.70 (s, 3H), 0.86 (d, J=6.6 Hz, 3H), 0.88 (d, J=6.6 Hz, 3H), 0.94 (d, J=6.6 Hz, 3H), 0.98-1.57 (m, 17H), 1.70-2.27 (m, 8H), 2.31-2.45 (m, 3H), 4.71-4.76 (m, 2H).

Example 7

(Z)-3-Hydroxyimino-7-oxa-4,8-cholestadien-6-one (Compound 8)

The title compound (14.4 mg, 51%) was obtained by using Compound 5 (27.4 mg, 0.0687 mmol) obtained in Example 4 in the same manner as Example 3.

ESI-MS: m/z 414 [M+H]$^+$, $^1$H NMR (CDCl$_3$) δ(ppm): 0.73 (s, 3H), 0.86 (d, J=6.6 Hz, 3H), 0.88 (d, J=6.6 Hz, 3H), 0.94 (d, J=6.3 Hz, 3H), 0.98-2.10 (m, 21H), 2.17-2.38 (m, 4H), 3.06-3.14 (m, 1H), 7.21 (s, 1H).

Example 8

(3R,5S)-3-Ethylamino-7-oxa-8-cholesten-6-one (Compound 10) and (3S,5S)-3-ethylamino-7-oxa-8-cholesten-6-one (Compound 11)

Compound 1 (19.7 mg, 0.0492 mmol) obtained in Example 1 was dissolved in THF (5.0 mL), and 2.0 mol/L of an ethylamine/THF solution (1.0 mL, 2.00 mmol) and powered Molecular Sieves 4 Å (1.0 g) were added thereto at room temperature, followed by stirring overnight. Subsequently, sodium triacetoxyborohydride (208 mg, 0.492 mmol) was added to the reaction mixture, followed by stirring for 30 minutes. A saturated aqueous ammonium chloride solution was added to the reaction mixture and filtered through a cotton plug, followed by extraction with chloroform five times. The organic layer was dried over anhydrous magnesium sulfate, and concentrated under reduced pressure to yield a residue. The residue was purified by preparative thin layer chromatography to obtain compound 10 (4.1 mg, 19%) and compound 11 (4.8 mg, 23%).

Compound 10; $^1$H NMR (CDCl$_3$) δ(ppm): 0.67 (s, 3H), 0.86 (d, J=7.0 Hz, 3H), 0.88 (d, J=7.0 Hz, 3H), 0.92 (d, J=6.6 Hz, 3H), 0.95 (s, 3H), 0.99-2.37 (m, 27H), 2.53-2.65 (m, 2H), 2.93 (dd, J=3.3, 12.9 Hz, 1H), 3.00-3.06 (m, 1H).

Compound 11; ESI-MS: m/z 430 [M+H]$^+$, $^1$H NMR (CDCl$_3$) δ(ppm): 0.67 (s, 3H), 0.86 (d, J=7.0 Hz, 3H), 0.88 (d, J=7.0 Hz, 3H), 0.92 (d, J=6.6 Hz, 3H), 0.95 (s, 3H), 0.99-1.83 (m, 21H), 1.90-2.56 (m, 8H), 2.60-2.80 (m, 2H).

Example 9

(R)-7-Oxa-1,8-cholesten-3,6-dione (Compound 12)

Compound 4 (30.0 mg, 0.0753 mmol) obtained in Example 4 was dissolved in THF (2.0 mL), and 1,8-diazabicyclo[5.4.0]undeca-7-ene (80.0 µL, 0.534 mmol) was added thereto at room temperature, followed by stirring for 2 hours. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (22.3 mg, 74%).

¹H NMR (CDCl₃) δ(ppm): 0.76 (s, 3H), 0.86 (d, J=7.0 Hz, 3H), 0.88 (d, J=7.0 Hz, 3H), 0.94 (d, J=6.6 Hz, 3H), 0.99-1.85 (m, 16H), 1.95-2.21 (m, 3H), 2.26-2.43 (m, 2H), 2.63 (dd, J=4.0, 16.5 Hz, 1H), 2.92 (dd, J=8.8, 16.5 Hz, 1H), 3.01 (dd, J=4.0, 8.8 Hz, 1H), 5.98 (d, J=9.9 Hz, 1H), 6.65 (d, J=9.9 Hz, 1H).

Example 10

(3S,5S)-3-Amino-7-oxa-8-cholesten-6-one (Compound 13) and (3R,5S)-3-hydroxy-7-oxa-8-cholesten-6-one (Compound 105)

Step 1; Compound 1 (359 mg, 0.896 mmol) obtained in Example 1 was dissolved in THF (10 mL), and 1.0 mol/L of a potassium tri(sec-butyl)borohydride/THF solution (1.61 mL, 1.61 mmol) was added thereto at −78° C., followed by stirring for 50 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain compound 105 (157 mg, 39%).

¹H NMR (CDCl₃) δ(ppm): 0.67 (s, 3H), 0.86 (d, J=6.6 Hz, 3H), 0.88 (d, J=6.6 Hz, 3H), 0.93 (d, J=6.6 Hz, 3H), 0.94 (s, 3H), 0.99-2.42 (m, 24H), 2.91 (dd, J=3.6, 12.6 Hz, 1H), 4.22 (m, 1H).

Step 2; (3R,5S)-3-Hydroxy-7-oxa-8-cholesten-6-one (70.0 mg, 0.174 mmol) obtained in the Step 1 and triphenylphosphine (73.0 mg, 0.278 mmol) were dissolved in toluene (1.5 mL), and 2.2 mol/L of an diethyl azodicarboxylate/toluene solution (119 µL, 0.261 mmol) and diphenyl phosphorazidate (112 µL, 0.522 mmol) were added thereto at 0° C., followed by stirring for 1 hour. Subsequently, 2.2 mol/L of an diethyl azodicarboxylate/toluene solution (39.7 µL, 0.0869 mmol) and triphenylphosphine (22.8 mg, 0.0869 mmol) were further added, followed by stirring for 20 minutes, and then stirring at room temperature for 1 hour. The residue obtained by concentration under reduced pressure was purified by silica gel column chromatography to obtain (3S,5S)-3-azido-7-oxa-8-cholesten-6-one (33.5 mg, 45%).

¹H NMR (CDCl₃) δ(ppm): 0.76 (s, 3H), 0.86 (d, J=6.6 Hz, 3H), 0.88 (d, J=6.6 Hz, 3H), 0.93 (d, J=6.6 Hz, 3H), 0.97 (s, 3H), 1.00-1.79 (m, 17H), 1.88-2.43 (m, 8H), 3.25-3.36 (m, 1H).

Step 3; (3S,5S)-3-Azido-7-oxa-8-cholesten-6-one (33.5 mg, 0.0783 mmol) obtained in the Step 2 was dissolved in a mixed solvent of THF (1.0 mL) and water (0.1 mL), and triphenylphosphine (41.0 mg, 0.157 mmol) was added thereto at room temperature, followed by stirring overnight. The residue obtained by concentration under reduced pressure was purified by silica gel column chromatography to obtain compound 13 (27.3 mg, 87%).

ESI-MS: m/z 402 [M+H]⁺, ¹H NMR (CDCl₃) δ(ppm): 0.67 (s, 3H), 0.86 (d, J=7.0 Hz, 3H), 0.88 (d, J=7.0 Hz, 3H), 0.93 (d, J=6.6 Hz, 3H), 0.95 (s, 3H), 0.97-1.60 (m, 15H), 1.63-1.82 (m, 3H), 1.90-2.43 (m, 7H), 2.65-2.75 (m, 1H).

Example 11

(3S,5S)-3-N-Methanesulfonylamino-7-oxa-8-cholesten-6-one (Compound 14)

Compound 13 (7.0 mg, 0.017 mmol) obtained in the Step 3 of Example 10 was dissolved in dichloromethane (0.5 mL), and triethylamine (3.6 µL, 0.026 mmol) and methanesulfonyl chloride (2.0 µL, 0.026 mmol) were added thereto at room temperature, followed by stirring for 20 minutes. A saturated aqueous ammonium chloride solution was added to the reaction mixture, followed by extraction with chloroform twice. The organic layer was washed with saturated brine, dried over anhydrous magnesium sulfate, and concentrated under reduced pressure to yield a residue. The residue was purified by preparative thin layer chromatography to obtain the title compound (6.2 mg, 74%).

ESI-MS: m/z 480 [M+H]⁺, ¹H NMR (CDCl₃) δ(ppm): 0.67 (s, 3H), 0.86 (d, J=6.6 Hz, 3H), 0.88 (d, J=6.6 Hz, 3H), 0.93 (d, J=6.6 Hz, 3H), 0.95 (s, 3H), 0.98-1.75 (m, 17H), 1.92-2.47 (m, 8H), 3.01 (s, 3H), 3.27-3.38 (m, 1H), 4.29-4.33 (m, 1H).

Example 12

(3S,5S)-3-N-Phenylcarbamoylamino-7-oxa-8-cholesten-6-one (Compound 15)

The title compound (5.0 mg, 67%) was obtained by using Compound 13 (5.8 mg, 0.014 mmol) obtained in the Step 3 of Example 10 and phenyl isocyanate (2.4 µL, 0.022 mmol) in the same manner as Example 11.

ESI-MS: m/z 521 [M+H]⁺, ¹H NMR (CDCl₃) δ(ppm): 0.67 (s, 3H), 0.86 (d, J=6.6 Hz, 3H), 0.88 (d, J=6.6 Hz, 3H), 0.91 (s, 3H), 0.94 (d, J=6.6 Hz, 3H), 0.98-1.79 (m, 17H), 1.90-2.45 (m, 8H), 3.63-3.73 (m, 1H), 4.93-4.98 (m, 1H), 6.68 (s, 1H), 7.01-7.11 (m, 1H), 7.28-7.31 (m, 4H).

Example 13

(3S,5S)-3-N-Benzoylamino-7-oxa-8-cholesten-6-one (Compound 16)

The title compound (7.1 mg, 87%) was obtained by using Compound 13 (6.5 mg, 0.016 mmol) obtained in the Step 3 of Example 10 and benzoyl chloride (2.8 µL, 0.024 mmol) in the same manner as Example 11.

ESI-MS: m/z 506 [M+H]⁺, ¹H NMR (CDCl₃) δ(ppm): 0.68 (s, 3H), 0.86 (d, J=6.6 Hz, 3H), 0.88 (d, J=6.6 Hz, 3H), 0.94 (d, J=6.6 Hz, 3H), 0.98 (s, 3H), 1.00-1.78 (m, 17H), 1.92-2.56 (m, 8H), 3.96-4.07 (m, 1H), 6.03-6.09 (m, 1H), 7.40-7.53 (m, 3H), 7.71-7.78 (m, 2H).

Example 14

(3S,5S)-3-N-Acetylamino-7-oxa-8-cholesten-6-one (Compound 17)

Compound 13 (4.2 mg, 0.0105 mmol) obtained in the Step 3 of Example 10 was dissolved in a mixed solvent of acetic anhydride (0.5 mL) and pyridine (0.25 mL), followed by stirring for 50 minutes. The residue obtained by concentration under reduced pressure was purified by preparative thin layer chromatography to obtain the title compound (4.0 mg, 86%).

ESI-MS: m/z 444 [M+H]⁺, ¹H NMR (CDCl₃) δ(ppm): 0.67 (s, 3H), 0.86 (d, J=6.6 Hz, 3H), 0.88 (d, J=6.6 Hz, 3H), 0.93 (d, J=6.6 Hz, 3H), 0.95 (s, 3H), 0.99-1.78 (m, 17H), 1.90-2.49 (m, 11H), 3.75-3.84 (m, 1H), 5.34-5.39 (m, 1H).

Example 15

(1R,2R,5S)-1,2-Dihydroxy-7-oxa-8-cholesten-3,6-dione (Compound 18)

Compound 4 (61.7 mg, 0.155 mmol) obtained in Example 4 was dissolved in a mixed solvent of tert-butyl alcohol (4.8 mL) and water (0.8 mL), and 1% of an aqueous solution of potassium permanganate (2.39 mL, 0.155 mmol) was added thereof at 0° C., followed by stirring at 15 minutes. A saturated aqueous sodium thiosulfate solution was added to the reaction mixture, followed by filtering through a celite, and the filtrate was extracted with ethyl acetate twice. The organic layer was washed with saturated brine, dried over anhydrous magnesium sulfate, and concentrated under reduced pressure to yield a residue. The residue was purified by preparative thin layer chromatography to obtain the title compound (22.5 mg, 34%).

ESI-MS: m/z 433 [M+H]$^+$, $^1$H NMR (CDCl$_3$) δ(ppm): 0.71 (s, 3H), 0.86 (d, J=6.6 Hz, 3H), 0.88 (d, J=6.6 Hz, 3H), 0.94 (d, J=6.6 Hz, 3H), 0.97-1.79 (m, 15H), 1.92-2.11 (m, 2H), 2.17-2.30 (m, 1H), 2.35-2.46 (m, 1H), 2.50-2.79 (m, 3H), 2.95 (dd, J=4.4, 15.8 Hz, 1H), 3.41 (dd, J=4.4, 13.2 Hz, 1H), 3.75-3.85 (br s, 1H), 4.19 (d, J=2.9 Hz, 1H), 4.28 (d, J=2.9 Hz, 1H).

Example 16

(3S,5S)-3-Hydroxy-7-oxa-1,8-cholestadien-6-one (Compound 19)

Compound 4 (19 mg, 0.048 mmol) obtained in Example 4 was suspended in methanol (1.0 mL), and cerium chloride heptahydrate (36 mg, 0.096 mmol) and sodium borohydride (0.9 mg, 0.024 mmol) were added thereof at 0° C., followed by stirring at room temperature for 10 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (17 mg, 91%).

ESI-MS: m/z 401 [M+H]$^+$, $^1$H NMR (CDCl$_3$) δ(ppm): 0.69 (s, 3H), 0.86 (d, J=6.6 Hz, 3H), 0.88 (d, J=6.6 Hz, 3H), 0.94 (d, J=6.6 Hz, 3H), 0.97-2.12 (m, 19H), 2.25-2.36 (m, 3H), 2.52-2.60 (m, 1H), 2.69 (dd, J=2.4, 13.2 Hz, 1H), 4.32-4.41 (m, 1H), 5.62-5.69 (m, 1H), 5.83 (dd, J=2.0, 10.2 Hz, 1H).

Example 17

(3S,5R)-3-Hydroxy-5-methyl-7-oxa-8-cholesten-6-one (Compound 20), (3S,5R)-3-methoxy-5-methyl-7-oxa-8-cholesten-6-one (Compound 22), and (3S,5S)-3-methoxy-5-methyl-7-oxa-8-cholesten-6-one (Compound 23)

Compound 2 (67 mg, 0.17 mmol) obtained in Example 2 was dissolved in DMF (2.0 mL), and silver oxide (120 mg, 0.50 mmol), iodomethane (52 μL, 0.84 mmol) and potassium iodide (83 mg, 0.50 mmol) were added under light shading at room temperature, followed by stirring for 1 hour. Ethyl acetate was added until the reaction mixture became white turbidity, followed by filtration through a celite. The filtrate was washed with water and saturated brine, dried over anhydrous magnesium sulfate, and concentrated under reduced pressure to yield a residue. The residue was purified by preparative thin layer chromatography to obtain compound 20 (3.6 mg, 5%), compound 22 (44 mg, 61%), and compound 23 (20 mg, 28%).

Compound 20; ESI-MS: m/z 417 [M+H]$^+$, $^1$H NMR (CDCl$_3$) δ(ppm): 0.78 (s, 3H), 0.86 (d, J=6.6 Hz, 3H), 0.88 (d, J=6.6 Hz, 3H), 0.93 (d, J=6.6 Hz, 3H), 0.98-1.85 (m, 24H), 1.92-2.33 (m, 5H), 2.41-2.48 (m, 1H), 3.82-3.93 (m, 1H).

Compound 22; ESI-MS: m/z 431 [M+H]$^+$, $^1$H NMR (CDCl$_3$) δ(ppm): 0.77 (s, 3H), 0.86 (d, J=6.6 Hz, 3H), 0.88 (d, J=6.6 Hz, 3H), 0.94 (d, J=6.3 Hz, 3H), 0.98-2.34 (m, 29H), 2.50-2.57 (m, 1H), 3.32-3.45 (m, 1H), 3.38 (s, 3H).

Compound 23; ESI-MS: m/z 431 [M+H]$^+$, $^1$H NMR (CDCl$_3$) δ(ppm): 0.68 (s, 3H), 0.86 (d, J=7.0 Hz, 3H), 0.88 (d, J=7.0 Hz, 3H), 0.93 (d, J=6.6 Hz, 3H), 0.98-1.82 (m, 23H), 1.90-2.28 (m, 5H), 2.31-2.48 (m, 2H), 3.35-3.46 (m, 1H), 3.36 (s, 3H).

Example 18

(1S,5S)-1-Hydroxy-7-oxa-2,8-cholestadien-6-one (Compound 21)

Compound 6 (9.0 mg, 0.022 mmol) obtained in Example 5 was dissolved in ethanol (0.5 mL), and hydrazine monohydrate (10 μL) and acetic acid (10 μL) were added thereto at room temperature, followed by stirring for 1 hour. Water was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (6.2 mg, 71%).

ESI-MS: m/z 401 [M+H]$^+$, $^1$H NMR (CDCl$_3$) δ(ppm): 0.69 (s, 3H), 0.86 (d, J=7.0 Hz, 3H), 0.88 (d, J=7.0 Hz, 3H), 0.90 (s, 3H), 0.94 (d, J=6.3 Hz, 3H), 0.97-1.81 (m, 13H), 1.91-2.09 (m, 2H), 2.17-2.59 (m, 5H), 3.02 (dd, J=6.0, 11.4 Hz, 1H), 3.92-3.98 (m, 1H), 5.84-5.98 (m, 2H).

Example 19

(3S,5R)-3-Hydroxy-5-allyl-7-oxa-8-cholesten-6-one (Compound 24) and (3S,5S)-3-hydroxy-5-allyl-7-oxa-8-cholesten-6-one (Compound 30)

Step 1; Compound 2 (109 mg, 0.270 mmol) obtained in Example 2 was dissolved in dichloromethane (1.0 mL), and imidazole (36.8 mg, 0.541 mmol) and chlorotriethylsilane (68.1 μL, 0.406 mmol) were added thereto at room temperature, followed by stirring for 20 minutes. A saturated aqueous ammonium chloride solution was added to the reaction mixture, followed by extraction with chloroform twice. The organic layer was washed with saturated brine, dried over anhydrous magnesium sulfate, and concentrated under reduced pressure to yield a residue. The residue was purified by silica gel column chromatography to obtain (3S,5S)-3-triethylsiloxy-7-oxa-8-cholesten-6-one (124 mg, 89%).

$^1$H NMR (CDCl$_3$) δ(ppm): 0.59 (q, J=7.9 Hz, 6H), 0.67 (s, 3H), 0.86 (d, J=7.0 Hz, 3H), 0.88 (d, J=7.0 Hz, 3H), 0.91-0.99 (m, 15H), 1.01-1.79 (m, 19H), 1.90-2.40 (m, 6H), 3.51-3.63 (m, 1H).

Step 2; By using (3S,5S)-3-triethylsiloxy-7-oxa-8-cholesten-6-one (42.0 mg, 0.0812 mmol) obtained in the Step 1, silver oxide (56.4 mg, 0.243 mmol), allyl bromide (35.2 μL, 0.406 mmol) and potassium iodide (40.0 mg, 0.243 mmol), (3S,5R)-3-tiethylsiloxy-5-allyl-7-oxa-8-cholesten-6-one (22.1 mg, 49%) and (3S,5S)-3-triethylsiloxy-5-allyl-7-oxa-8-cholesten-6-one (11.0 mg, 24%) were obtained in the same manner as Example 17.

(3S,5R)-3-Tiethylsiloxy-5-allyl-7-oxa-8-cholesten-6-one;
$^1$H NMR (CDCl$_3$) δ(ppm): 0.62 (q, J=7.8 Hz, 6H), 0.79 (s, 3H), 0.86 (d, J=6.6 Hz, 3H), 0.88 (d, J=6.6 Hz, 3H), 0.93 (d, J=6.3 Hz, 3H), J=7.8 Hz, 9H), 1.01-2.32 (m, 27H), 2.41-2.51 (m, 2H), 3.75-3.86 (m, 1H), 4.95-5.01 (m, 2H), 5.59-5.74 (m, 1H).

(3S,5S)-3-Triethylsiloxy-5-allyl-7-oxa-8-cholesten-6-one;

$^1$H NMR (CDCl$_3$) δ(ppm): 0.57 (q, J=7.8 Hz, 6H), 0.68 (s, 3H), 0.86 (d, J=7.0 Hz, 3H), 0.88 (d, J=7.0 Hz, 3H), 0.91-1.00 (m, 12H), 1.06-1.81 (m, 21H), 1.91-2.53 (m, 8H), 3.74-3.84 (m, 1H), 5.04-5.14 (m, 2H), 5.58-5.72 (m, 1H).

Step 3; (3S,5R)-3-Triethylsiloxy-5-allyl-7-oxa-8-cholesten-6-one (4.0 mg, 0.0072 mmol) obtained in the Step 2 was dissolved in a mixed solvent of ethanol (0.8 mL) and water (0.1 mL), and sodium periodate (4.6 mg, 0.022 mmol) was added thereto at room temperature, followed by stirring for 30 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain compound 24 (1.8 mg, 57%).

ESI-MS: m/z 443 [M+H]$^+$, $^1$H NMR (CDCl$_3$) δ(ppm): 0.80 (s, 3H), 0.86 (d, J=6.8 Hz, 3H), 0.88 (d, J=6.8 Hz, 3H), 0.94 (d, J=6.6 Hz, 3H), 1.01-2.35 (m, 27H), 2.46-2.57 (m, 2H), 3.82-3.96 (m, 1H), 4.98-5.12 (m, 2H), 5.59-5.72 (m, 1H).

Step 4; (3S,5S)-3-Triethylsiloxy-5-allyl-7-oxa-8-cholesten-6-one (5.0 mg, 0.0090 mmol) obtained in the Step 2 was dissolved in THF (1.0 mL), and acetic acid (1.0 μL, 0.018 mmol) and 1.0 mol/L of a tetrabutylammonium fluoride/THF solution (18 μL, 0.018 mmol) were added thereto at room temperature, followed by stirring for 2 hours. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain compound 30 (3.1 mg, 78%).

ESI-MS: m/z 443 [M+H]$^+$, $^1$H NMR (CDCl$_3$) δ(ppm): 0.69 (s, 3H), 0.86 (d, J=7.0 Hz, 3H), 0.88 (d, J=7.0 Hz, 3H), 0.93 (d, J=6.6 Hz, 3H), 0.99-2.53 (m, 29H), 3.80-3.92 (m, 1H), 5.04-5.14 (m, 2H), 5.59-5.73 (m, 1H).

Example 20

(3S,5R)-3-Hydroxy-5-ethyl-7-oxa-8-cholesten-6-one (Compound 25)

Step 1; By using (3S,5S)-3-triethylsiloxy-7-oxa-8-cholesten-6-one (9.0 mg, 0.017 mmol) obtained in the Step 1 of Example 19, silver oxide (8.0 mg, 0.035 mmol), iodoethane (14 μL, 0.174 mmol) and potassium iodide (5.8 mg, 0.035 mmol), (3S,5R)-3-triethylsiloxy-5-ethyl-7-oxa-8-cholesten-6-one (4.9 mg, 52%) was obtained in the same manner as Example 17.

$^1$H NMR (CDCl$_3$) δ(ppm): 0.63 (q, J=8.1 Hz, 6H), 0.76 (s, 3H), J=7.7 Hz, 3H), 0.86 (d, J=6.9 Hz, 3H), 0.88 (d, J=6.9 Hz, 3H), 0.93 (d, J=6.6 Hz, 3H), 0.97 (t, J=8.1 Hz, 9H), 1.01 (s, 3H), 1.05-1.84 (m, 20H), 1.91-2.32 (m, 5H), 2.45-2.53 (m, 1H), 3.75-3.87 (m, 1H).

Step 2; By using (3S,5R)-3-triethylsiloxy-5-ethyl-7-oxa-8-cholesten-6-one (4.9 mg, 0.0090 mmol) obtained in the Step 1, compound 25 (3.0 mg, 77%) was obtained in the same manner as the Step 4 of Example 19.

ESI-MS: m/z 431 [M+H]$^+$, $^1$H NMR (CDCl$_3$) δ(ppm): 0.77 (s, 3H), 0.83 (t, J=7.0 Hz, 3H), 0.86 (d, J=7.0 Hz, 3H), 0.88 (d, J=7.0 Hz, 3H), 0.93 (d, J=6.6 Hz, 3H), 1.01-2.32 (m, 28H), 2.55-2.63 (m, 1H), 3.83-3.97 (m, 1H).

Example 21

(3S,5S)-3-Hydroxy-5-(2,3-dihydroxy)propyl-7-oxa-8-cholesten-6-one (Compound 26 and Compound 27)

Step 1; (3S,5R)-3-Triethylsiloxy-5-allyl-7-oxa-8-cholesten-6-one (23 mg, 0.042 mmol) obtained in the Step 2 of Example 19 was dissolved in a mixed solvent of tert-butyl alcohol (0.8 mL) and water (0.2 mL), and 4-methylmorpholin-N-oxide (7.3 mg, 0.062 mmol) and 2.5% of an osmium tetroxide/tert-butyl alcohol solution (26 μL, 0.00207 mmol) were added thereto at room temperature, followed by stirring overnight at room temperature. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to isolate each of the stereoisomer of (3S,5R)-3-triethylsiloxy-5-(2,3-dihydroxy)propyl-7-oxa-8-cholesten-6-one (Low polar compound; 8.3 mg, 34%, High polar compound; 12 mg, 48%).

Low polar compound; $^1$H NMR (CDCl$_3$) δ(ppm): 0.63 (q, J=7.8 Hz, 6H), 0.79 (s, 3H), 0.86 (d, J=7.0 Hz, 3H), 0.88 (d, J=7.0 Hz, 3H), 0.91-1.00 (m, 15H), 1.04-1.82 (m, 18H), 1.89-2.35 (m, 7H), 2.47-2.57 (m, 1H), 3.36 (dd, J=8.1, 10.6 Hz, 1H), 3.49 (dd, J=4.0, 10.6 Hz, 1H), 3.76-3.98 (m, 2H).

High polar compound; $^1$H NMR (CDCl$_3$) δ(ppm): 0.63 (q, J=8.1 Hz, 6H), 0.73 (s, 3H), 0.86 (d, J=7.0 Hz, 3H), 0.88 (d, J=7.0 Hz, 3H), 0.93 (d, J=6.6 Hz, 3H), 0.97 (t, J=8.1 Hz, 9H), 0.99-2.34 (m, 28H), 2.65-2.78 (m, 1H), 3.33 (dd, J=7.3, 11.0 Hz, 1H), 3.44-3.52 (m, 1H), 3.62-3.72 (m, 1H), 3.74-3.86 (m, 1H).

Step 2; By using the stereoisomer (Low polar compound; 5.5 mg, 0.0093 mmol) of (3S,5R)-3-triethylsiloxy-5-(2,3-dihydroxy)propyl-7-oxa-8-cholesten-6-one obtained in the Step 1, (3S,5S)-3-hydroxy-5-(2,3-dihydroxy)propyl-7-oxa-8-cholesten-6-one (Compound 26 or Compound 27) (3.6 mg, 81%) was obtained in the same manner as the Step 4 of Example 19.

ESI-MS: m/z 477 [M+H]$^+$, $^1$H NMR (CDCl$_3$) δ(ppm): 0.80 (s, 3H), 0.86 (d, J=7.0 Hz, 3H), 0.88 (d, J=7.0 Hz, 3H), 0.93 (d, J=6.6 Hz, 3H), 0.98-2.35 (m, 28H), 2.58-2.68 (m, 1H), 3.38 (dd, J=7.6, 10.9 Hz, 1H), 3.50 (dd, J=4.0, 10.9 Hz, 1H), 3.84-3.98 (m, 2H).

Step 3; By using the stereoisomer (High polar compound; 6.0 mg, 0.010 mmol) of (3S,5R)-3-triethylsiloxy-5-(2,3-dihydroxy)propyl-7-oxa-8-cholesten-6-one obtained in the Step 1, (3S,5S)-3-hydroxy-5-(2,3-dihydroxy)propyl-7-oxa-8-cholesten-6-one (Compound 27 or Compound 26) (3.7 mg, 76%) was obtained in the same manner as the Step 4 of Example 19.

ESI-MS: m/z 477 [M+H]$^+$, $^1$H NMR (CDCl$_3$) δ(ppm): 0.73 (s, 3H), 0.86 (d, J=7.0 Hz, 3H), 0.88 (d, J=7.0 Hz, 3H), 0.93 (d, J=6.6 Hz, 3H), 0.98-2.34 (m, 28H), 2.45-2.55 (m, 1H), 3.28-4.00 (m, 4H).

Example 22

(3S,5R)-3-Hydroxy-5-(2hydroxy)ethyl-7-oxa-8-cholesten-6-one (Compound 28)

(3S,5R)-3-Triethylsiloxy-5-(2,3-dihydroxy)propyl-7-oxa-8-cholesten-6-one (High polar compound; 5.0 mg, 0.0085 mmol) obtained in the Step 1 of Example 21 was dissolved in a mixed solvent of ethanol (0.9 mL) and water (0.15 mL), and then sodium periodate (7.2 mg, 0.034 mmol) was added thereto at room temperature, followed by stirring at 40° C. for 1 hour. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure. The resulting residue was dissolved in ethanol (1.0 mL), and sodium borohydride (0.6 mg, 0.0169 mmol) was added at 0° C., followed by stirring for 40 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (2.4 mg, 64%).

ESI-MS: m/z 447 [M+H]+, $^1$H NMR (CDCl$_3$) δ(ppm): 0.79 (s, 3H), 0.86 (d, J=7.0 Hz, 3H), 0.88 (d, J=7.0 Hz, 3H), 0.93 (d, J=6.3 Hz, 3H), 0.98-2.34 (m, 28H), 2.57-2.67 (m, 1H), 3.64-3.71 (m, 2H), 3.82-3.94 (m, 1H).

Example 23

(3S,5S)-3-Hydroxy-5-methyl-7-oxa-8-cholesten-6-one (Compound 29)

Step 1; By using (3S,5S)-3-triethylsiloxy-7-oxa-8-cholesten-6-one (30 mg, 0.058 mmol) obtained in the Step 1 of Example 19, silver oxide (40 mg, 0.17 mmol), iodomethane (36 μL, 0.58 mmol) and potassium iodide (29 mg, 0.17 mmol), (3S,5S)-3-triethylsiloxy-5-methyl-7-oxa-8-cholesten-6-one (8.9 mg, 29%) was obtained in the same manner as Example 17.

$^1$H NMR (CDCl$_3$) δ(ppm): 0.59 (q, J=8.1 Hz, 6H), 0.67 (s, 3H), 0.85 (d, J=7.0 Hz, 3H), 0.88 (d, J=7.0 Hz, 3H), 0.93 (d, J=6.3 Hz, 3H), 0.96 (t, J=8.1 Hz, 9H), 1.01-1.82 (m, 24H), 1.91-2.16 (m, 5H), 2.28-2.38 (m, 1H), 3.78-3.90 (m, 1H).

Step 2; Compound 29 (3.6 mg, 55%) was obtained by using (3S,5S)-3-triethylsiloxy-5-methyl-7-oxa-8-cholesten-6-one (8.9 mg, 0.017 mmol) obtained in the Step 1 in the same manner as the Step 4 of Example 19.

ESI-MS: m/z 417 [M+H]+, $^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.6 Hz, 3H), 1.00-1.80 (m, 24H), 1.85-2.16 (m, 5H), 2.28-2.38 (m, 1H), 3.82-3.94 (m, 1H).

Example 24

(3S,5S)-3-(2,3-Dihydroxy)propoxy-7-oxa-8-cholesten-6-one (Compound 35)

Step 1; Compound 2 (230 mg, 0.571 mmol) obtained in Example 2 was dissolved in dichloromethane (6.0 mL), and O-allyl-2,2,2-trichloroacetimidate (130 μL, 0.857 mmol) and boron trifluoride—ethyl ether complex (36.1 μL, 0.286 mmol) were added thereto at 0° C., followed by stirring for 3 hours. Subsequently, O-allyl-2,2,2-trichloroacetimidate (43.3 μL, 0.286 mmol) and boron trifluoride—ethyl ether complex (18.1 μL, 0.143 mmol) were further added thereto, followed by stirring for 4 hours. A saturated aqueous sodium bicarbonate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain (3S,5S)-3-allyloxy-7-oxa-8-cholesten-6-one (145 mg, 57%).

$^1$H NMR (CDCl$_3$) δ(ppm): 0.67 (s, 3H), 0.86 (d, J=7.0 Hz, 3H), 0.88 (d, J=7.0 Hz, 3H), 0.93 (d, J=6.3 Hz, 3H), 0.97 (s, 3H), 1.01-1.60 (m, 15H), 1.66-1.80 (m, 2H), 1.90-2.47 (m, 8H), 3.23-3.35 (m, 1H), 3.96-4.17 (m, 2H), 5.14-5.32 (m, 2H), 5.84-6.00 (m, 1H).

Step 2; (3S,5S)-3-Allyloxy-7-oxa-8-cholesten-6-one (71 mg, 0.16 mmol) obtained in the Step 1 was dissolved in a mixed solvent of tert-butyl alcohol (3.0 mL), THF (0.3 mL) and water (0.3 mL), and 4-methylmorpholin-N-oxide (9.4 mg, 0.081 mmol) and 2.5% of an osmium tetroxide/tert-butyl alcohol solution (100 μL, 0.0081 mmol) were added thereto at room temperature, followed by stirring for 90 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain compound 35 (16 mg, 21%).

ESI-MS: m/z 477 [M+H]+, $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.3 Hz, 3H), 0.97 (s, 3H), 1.01-1.79 (m, 17H), 1.91-2.47 (m, 8H), 2.55-2.75 (br s, 1H), 3.23-3.35 (m, 1H), 3.49-3.75 (m, 4H), 3.81-3.90 (m, 1H).

Example 25

(3S,5S)-3-(2-Hydroxy)ethoxy-7-oxa-8-cholesten-6-one (Compound 31)

Step 1; Compound 35 (60.0 mg, 0.126 mmol) obtained in the Step 2 of Example 24 was dissolved in a mixed solvent of ethanol (3.0 mL) and water (1.0 mL), and sodium periodate (80.8 mg, 0.378 mmol) was added thereto at room temperature, followed by stirring for 30 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain (3S,5S)-3-(formyl)methoxy-7-oxa-8-cholesten-6-one (46.6 mg, 83%).

Step 2; (3S,5S)-3-(Formyl)methoxy-7-oxa-8-cholesten-6-one (11.0 mg, 0.0247 mmol) obtained in the Step 1 was dissolved in ethanol (1.0 mL), and sodium borohydride (0.9 mg, 0.239 mmol) was added thereto at 0° C., followed by stirring for 15 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain compound 31 (7.2 mg, 67%).

ESI-MS: m/z 447 [M+H]+, $^1$H NMR (CDCl$_3$) δ(ppm): 0.68 (s, 3H), 0.86 (d, J=7.0 Hz, 3H), 0.88 (d, J=7.0 Hz, 3H), 0.93 (d, J=6.9 Hz, 3H), 0.97 (s, 3H), 1.00-2.47 (m, 25H), 3.24-3.36 (m, 1H), 3.48-3.77 (m, 4H).

Example 26

(1R,2S,3S,5R)-1,2,3-Trihydroxy-7-oxa-8-cholesten-6-one (Compound 33) and (1R,2S,3R,5S)-1,2,3-trihydroxy-7-oxa-8-cholesten-6-one (Compound 32)

Compound 18 (510 mg, 1.18 mmol) obtained in Example 15 was dissolved in THF (10 mL), and sodium triacetoxyborohydride (750 mg, 3.54 mmol) was added thereto at room temperature, followed by stirring for 4 hours. A saturated aqueous ammonium chloride solution was added to the reaction mixture, followed by extraction with ethyl acetate twice. The organic layer was washed with saturated brine, dried over anhydrous sodium sulfate, and concentrated under reduced pressure to yield a residue. The residue was purified by preparative high-speed liquid chromatography to obtain compound 33 (154 mg, 30%) and compound 32 (180 mg, 35%).

Compound 33; ESI-MS: m/z 435 [M+H]$^+$, $^1$H NMR (CDCl$_3$) δ(ppm): 0.68 (s, 3H), 0.86 (d, J=7.0 Hz, 3H), 0.88 (d, J=7.0 Hz, 3H), 0.94 (d, J=6.3 Hz, 3H), 0.99 (s, 3H), 1.00-1.60 (m, 12H), 1.68-2.24 (m, 5H), 2.36-2.57 (m, 3H), 2.82-2.95 (br s, 2H), 3.19 (dd, J=3.6, 13.2 Hz, 1H), 3.35-3.42 (m, 1H), 3.64-3.72 (m, 1H), 3.82-3.90 (m, 1H), 4.15-4.22 (m, 1H).

Compound 32; ESI-MS: m/z 435 [M+H]$^+$, $^1$H NMR (CDCl$_3$) δ(ppm): 0.68 (s, 3H), 0.86 (d, J=7.0 Hz, 3H), 0.88 (d, J=7.0 Hz, 3H), 0.93 (d, J=6.6 Hz, 3H), 0.97-1.76 (m, 18H), 1.90-2.40 (m, 5H), 2.50-2.72 (m, 2H), 3.09 (dd, J=3.3, 12.8 Hz, 1H), 3.62-3.69 (m, 1H), 3.81-3.95 (m, 2H).

Example 27

(1R,3aR,5aS,10aS,12aR)-10a,12a-Dimethyl-1-[(R)-6-methylheptan-2-yl]-1,2,3,3a,5a,6,9,10,10a,11,12,12a-dodecahydro-8-azacyclohepta[c]cyclopenta[h]chromen-5,7-dione (Compound 34)

Compound 3 (41.5 mg, 0.0999 mmol) obtained in Example 3 was dissolved in 1,4-dioxane (3.0 mL), and thionyl chloride (21.9 µL, 0.300 mmol) was added thereto at room temperature, followed by stirring for 1 hour. A saturated aqueous sodium bicarbonate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (11.6 mg, 28%).

$^1$H NMR (CDCl$_3$) δ(ppm): 0.67 (s, 3H), 0.86 (d, J=7.0 Hz, 3H), 0.88 (d, J=7.0 Hz, 3H), 0.93 (d, J=6.6 Hz, 3H), 0.98-1.83 (m, 18H), 1.91-2.40 (m, 5H), 2.59-2.79 (m, 2H), 3.05-3.22 (m, 2H), 3.33-3.46 (m, 1H), 6.48-6.55 (br s, 1H).

Example 28

(3S,5S)-3-(2-N-Methylamino)ethoxy-7-oxa-8-cholesten-6-one (Compound 36)

(3S,5S)-3-(Formyl)methoxy-7-oxa-8-cholesten-6-one (3.9 mg, 0.0088 mmol) obtained in the Step 1 of Example 25 was dissolved in a mixed solvent of THF (0.5 mL) and acetic acid (0.025 mL), and 2.0 mol/L of a methylamine/THF solution (13 µL, 0.026 mmol) and sodium triacetoxyborohydride (3.7 mg, 0.018 mmol) were added thereto at 0° C., followed by stirring at room temperature for 30 minutes. A saturated aqueous sodium bicarbonate solution was added to the reaction mixture, followed by extraction with chloroform four times. The organic layer was dried over anhydrous magnesium sulfate, and concentrated under reduced pressure to yield a residue. The residue was purified by preparative thin layer chromatography to obtain the title compound (2.0 mg, 50%).

ESI-MS: m/z 460 [M+H]$^+$, $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.6 Hz, 3H), 0.96 (s, 3H), 1.01-1.60 (m, 16H), 1.65-1.79 (m, 2H), 1.91-2.42 (m, 7H), 2.45 (s, 3H), 2.71-2.76 (m, 2H), 3.19-3.30 (m, 1H), 3.52-3.59 (m, 1H), 3.63-3.71 (m, 1H).

Example 29

(3S,5S)-3-[2-(4-Morphoryl)]ethoxy-7-oxa-8-cholesten-6-one (Compound 37)

By using (3S,5S)-3-(formyl)methoxy-7-oxa-8-cholesten-6-one (12.6 mg, 0.0283 mmol) obtained in the Step 1 of Example 25 and morpholine (12.4 µL, 0.142 mmol), the title compound (10.0 mg, 69%) was obtained in the same manner as Example 28.

ESI-MS: m/z 516 [M+H]$^+$, $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.6 Hz, 3H), 0.96 (s, 3H), 1.00-1.57 (m, 16H), 1.63-1.80 (m, 2H), 1.86-2.62 (m, 13H), 3.18-3.30 (m, 1H), 3.54-3.75 (m, 6H).

Example 30

(3S,5S)-3-(2-Amino)ethoxy-7-oxa-8-cholesten-6-one (Compound 38)

Step 1; By using compound 31 (31.5 mg, 0.705 mmol) obtained in the Step 2 of Example 25, (3S,5S)-3-(2-azido)ethoxy-7-oxa-8-cholesten-6-one (25.5 mg, 77%) was obtained in the same manner as the Step 2 of Example 10.

Step 2; Compound 38 (18.3 mg, 76%) was obtained by using (3S,5S)-3-(2-azido)ethoxy-7-oxa-8-cholesten-6-one (25.5 mg, 0.0541 mmol) obtained in the Step 1 in the same manner as the Step 3 of Example 10.

$^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.3 Hz, 3H), 0.97 (s, 3H), 1.01-1.57 (m, 16H), 1.64-1.80 (m, 2H), 1.92-2.48 (m, 7H), 2.82-2.88 (m, 2H), 3.20-3.32 (m, 1H), 3.44-3.52 (m, 1H), 3.54-3.65 (m, 1H).

Example 31

(3S,5S)-3-(2-N-Acetylamino)ethoxy-7-oxa-8-cholesten-6-one (Compound 39)

Compound 38 (4.6 mg, 0.010 mmol) obtained in the Step 2 of Example 30 was dissolved in dichloromethane (0.5 mL), and acetic anhydride (2.9 µL, 0.031 mmol) and triethylamine (4.3 µL, 0.031 mmol) were added thereto at room temperature, followed by stirring for 3 hours. A saturated aqueous ammonium chloride solution was added to the reaction mixture, followed by extraction with chloroform twice. The organic layer was dried over anhydrous magnesium sulfate, and concentrated under reduced pressure to yield a residue. The residue was purified by preparative thin layer chromatography to obtain the title compound (3.7 mg, 74%).

ESI-MS: m/z 488 [M+H]$^+$, $^1$H NMR (CDCl$_3$) δ(ppm): 0.67 (s, 3H), 0.86 (d, J=7.0 Hz, 3H), 0.88 (d, J=7.0 Hz, 3H), 0.93 (d, J=6.6 Hz, 3H), 0.97 (s, 3H), 1.01-1.60 (m, 16H), 1.65-1.78 (m, 2H), 1.90-2.41 (m, 10H), 3.20-3.31 (m, 1H), 3.39-3.49 (m, 2H), 3.52-3.62 (m, 2H), 5.79-5.84 (br s, 1H).

Example 32

(3S,5S)-3-(2-N-Methanesulfonylamino)ethoxy-7-oxa-8-cholesten-6-one (Compound 40)

By using compound 38 (4.1 mg, 0.010 mmol) obtained in the Step 2 of Example 30 and methanesulfonyl chloride (1.1

μL, 0.014 mmol), the title compound (3.8 mg, 79%) was obtained in the same manner as Example 31.

ESI-MS: m/z 524 [M+H]$^+$, $^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.6 Hz, 3H), 0.96 (s, 3H), 1.01-1.60 (m, 16H), 1.66-1.78 (m, 2H), 1.90-2.44 (m, 7H), 2.99 (s, 3H), 3.25-3.37 (m, 3H), 3.54-3.62 (m, 1H), 3.65-3.73 (m, 1H), 4.60-4.70 (br s, 1H).

Example 33

(3S,5S)-3-(4-Pyridyl)oxy-7-oxa-8-cholesten-6-one (Compound 41)

Compound 105 (29 mg, 0.072 mmol) obtained in the Step 1 of Example 10, 4-hydroxypyridine (21 mg, 0.22 mmol) and triphenylphosphine (76 mg, 0.29 mmol) were dissolved in toluene (1.0 mL), and 2.2 mol/L of an diethyl azodicarboxylate/toluene solution (66 μL, 0.14 mmol) was added thereto at room temperature, followed by stirring for 3 hours. The residue obtained by concentration under reduced pressure was purified by silica gel column chromatography to obtain the title compound (5.2 mg, 15%).

$^1$H NMR (CDCl$_3$) δ(ppm): 0.69 (s, 3H), 0.86 (d, J=6.6 Hz, 3H), 0.88 (d, J=6.6 Hz, 3H), 0.94 (d, J=6.6 Hz, 3H), 0.97-1.85 (m, 21H), 1.90-2.55 (m, 7H), 4.25-4.41 (m, 1H), 6.77 (dd, J=1.5, 4.8 Hz, 2H), 8.41 (dd, J=1.5, 4.8 Hz, 2H).

Example 34

(3S,5S)-3-(3-Pyridyl)oxy-7-oxa-8-cholesten-6-one (Compound 42)

By using compound 105 (46.3 mg, 0.115 mmol) obtained in the Step 1 of Example 10 and 3-hydroxypyridine (21.9 mg, 0.230 mmol), the title compound (12.4 mg, 22%) was obtained in the same manner as Example 33.

ESI-MS: m/z 480 [M+H]$^+$, $^1$H NMR (CDCl$_3$) δ(ppm): 0.69 (s, 3H), 0.87 (d, J=6.6 Hz, 3H), 0.87 (d, J=6.6 Hz, 3H), 0.94 (d, J=6.3 Hz, 3H), 0.97-1.83 (m, 20H), 1.91-2.39 (m, 6H), 2.43-2.56 (m, 2H), 4.23 (m, 1H), 7.17-7.21 (m, 2H), 8.22 (m, 1H), 8.30 (m, 1H).

Example 35

(3S,5S)-3-(2-N-Phenylcarbamoylamino)ethoxy-7-oxa-8-cholesten-6-one (Compound 43)

By using compound 38 (5.5 mg, 0.012 mmol) obtained in the Step 2 of Example 30 and phenyl isocyanate (1.6 μL, 0.015 mmol), the title compound (4.1 mg, 59%) was obtained in the same manner as Example 31.

ESI-MS: m/z 565 [M+H]$^+$, $^1$H NMR (CDCl$_3$) δ(ppm): 0.68 (s, 3H), 0.86 (d, J=6.6 Hz, 3H), 0.88 (d, J=6.6 Hz, 3H), 0.93 (d, J=6.6 Hz, 3H), 0.96 (s, 3H), 1.01-1.60 (m, 17H), 1.66-1.78 (m, 2H), 1.90-2.44 (m, 7H), 2.99 (s, 3H), 3.25-3.37 (m, 3H), 3.57 (m, 1H), 3.68 (m, 1H), 4.65 (br s, 1H).

Example 36

(3S,5S)-3-(2-Hydroxy)propoxy-7-oxa-8-cholesten-6-one (1:1 diastereomer mixture, Compound 44) and (3S,5S)-3-(3-hydroxy)propoxy-7-oxa-8-cholesten-6-one (Compound 45)

Step 1; (3S,5S)-3-Allyloxy-7-oxa-8-cholesten-6-one (50.8 mg, 0.115 mmol) obtained in the Step 1 of Example 24 was dissolved in a mixed solvent of DMF (2.1 mL) and water (0.3 mL), and palladium chloride (10.2 mg, 0.0574 mmol) and cupric acetate monohydrate (22.9 mg, 0.115 mmol) were added thereto at room temperature, followed by stirring overnight. Subsequently, palladium chloride (10.2 mg, 0.0574 mmol) and cupric acetate monohydrate (22.9 mg, 0.115 mmol) were added, followed by stirring overnight. To the reaction mixture, 10% aqueous ammonia was added, followed by extraction with ethyl acetate twice. The organic layer was washed with saturated brine, dried over anhydrous magnesium sulfate, and concentrated under reduced pressure to yield a residue. The residue was purified by silica gel column chromatography to obtain a mixture (14.8 mg, 28%) of (3S,5S)-3-(2-oxo)propoxy-7-oxa-8-cholesten-6-one and (3S,5S)-3-(2-formyl)ethoxy-7-oxa-8-cholesten-6-one.

Step 2; A mixture (15 mg, 0.032 mmol) of (3S,5S)-3-(2-oxo)propoxy-7-oxa-8-cholesten-6-one and (3S,5S)-3-(2-formyl)ethoxy-7-oxa-8-cholesten-6-one obtained in the Step 1 was dissolved in methanol (1.0 mL), and sodium borohydride (1.2 mg, 0.032 mmol) was added thereto at 0° C., followed by stirring for 10 minutes. A saturated aqueous ammonium chloride solution was added to the reaction mixture, followed by extraction with ethyl acetate twice. The organic layer was washed with saturated brine, dried over anhydrous sodium sulfate, and concentrated under reduced pressure to yield a residue. The residue was purified by preparative thin layer chromatography to obtain compound 44 (13 mg, 84%) and compound 45 (1.8 mg, 12%).

Compound 44; $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.3 Hz, 3H), 0.96 (s, 3H), 1.01-1.78 (m, 21H), 1.90-2.46 (m, 7H), 3.16-3.37 (m, 2H), 3.48 (dd, J=3.3, 9.2 Hz, 0.5H), 3.57 (dd, J=3.3, 9.2 Hz, 0.5H), 3.89 (m, 1H).

Compound 45; $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.3 Hz, 3H), 0.97 (s, 3H), 1.01-1.57 (m, 18H), 1.65-1.87 (m, 4H), 1.91-2.50 (m, 7H), 3.20-3.31 (m, 1H), 3.59-3.67 (m, 1H), 3.73-3.81 (m, 1H).

Example 37

(3S,5S)-3-Glucopyranosiloxy-7-oxa-8-cholesten-6-one (1:1 diastereomer mixture, Compound 46)

Step 1; By using compound 2 (15.0 mg, 0.0373 mmol) obtained in Example 2 and 2,3,4,6-tetra-O-benzyl-α-D-glucopyranosyl trichloroacetimidate (38.3 mg, 0.0559 mmol), (3S,5S)-3-(2,3,4,6-tetra-O-benzyloxyglucopyranosyl)oxy-7-oxa-8-cholesten-6-one (1:1 diastereomer mixture) (15.4 mg, 45%) was obtained in the same manner as the Step 1 of Example 24.

$^1$H NMR (CDCl$_3$) δ(ppm): 0.67 (s, 3H), 0.86 (d, J=7.0 Hz, 3H), 0.88 (d, J=7.0 Hz, 3H), 0.94 (d, J=6.3 Hz, 3H), 0.97 (s, 3H), 1.01-1.79 (m, 18H), 1.84-2.50 (m, 7H), 3.44-4.00 (m, 7H), 4.40-5.01 (m, 9H), 7.11-7.40 (m, 20H).

Step 2; (3S,5S)-3-(2,3,4,6-Tetra-O-benzyloxyglucopyranosyl)oxy-7-oxa-8-cholesten-6-one (15.4 mg, 0.0167 mmol) obtained in the Step 1 was dissolved in ethanol (1.0 mL), and 10% palladium-carbon (10.0 mg) was added thereto at room temperature, followed by stirring for 6 hours under a hydrogen atmosphere. The reaction mixture was filtered through a celite, and the filtrate was concentrated under reduced pressure to yield a residue. The residue was purified by preparative thin layer chromatography to obtain compound 46 (4.4 mg, 47%).

ESI-MS: m/z 565 [M+H]+, 1H NMR (DMSO-d6) δ(ppm): 0.64 (s, 1.5H), 0.73 (s, 1.5H), 0.83-0.93 (m, 12H), 1.00-2.60 (m, 25H), 2.85-3.69 (m, 7H), 4.22-4.95 (m, 5H).

Example 38

(3S,5S)-3-Benzyloxy-7-oxa-8-cholesten-6-one
(Compound 47)

By using compound 2 (48.0 mg, 0.119 mmol) obtained in Example 2 and O-benzyl 2,2,2-trichloroacetamidate (33.2 μL, 0.179 mmol), the title compound (20.0 mg, 34%) was obtained in the same manner as the Step 1 of Example 24.

ESI-MS: m/z 493 [M+H]+, 1H NMR (CDCl3) δ(ppm): 0.67 (s, 3H), 0.86 (d, J=6.6 Hz, 3H), 0.88 (d, J=6.6 Hz, 3H), 0.93 (d, J=6.3 Hz, 3H), 0.97 (s, 3H), 1.01-1.80 (m, 18H), 1.84-2.37 (m, 6H), 2.45-2.55 (m, 1H), 3.30-3.41 (m, 1H), 4.53 (d, J=11.7 Hz, 1H), 4.65 (d, J=11.7 Hz, 1H), 7.12-7.38 (m, 5H).

Example 39

(2R,5S)-2-Hydroxy-7-oxa-8-cholesten-3,6-dione
(Compound 48) and (4S,5R)-4-hydroxy-7-oxa-8-
cholesten-3,6-dione (Compound 51)

Compound 1 (200 mg, 0.500 mmol) obtained in Example 1 was dissolved in a mixed solvent of acetonitrile (3.0 mL) and dichloromethane (1.5 mL), and hexamethyldisilazane (315 μL, 1.50 mmol), sodium iodide (150 mg, 0.999 mmol) and chlorotrimethylsilane (95.0 μL, 0.749 mmol) were added thereto at 0° C., followed by stirring at room temperature for 1 hour. Subsequently, chlorotrimethylsilane (31.7 μL, 0.250 mmol) was further added thereto, followed by stirring for 30 minutes. A saturated aqueous sodium bicarbonate solution was added to the reaction mixture, followed by extraction with ethyl acetate twice. The organic layer was washed with saturated brine, dried over anhydrous magnesium sulfate, and concentrated under reduced pressure. The resulting residue was dissolved in diethyl ether (4.0 mL), and 4-methylmorpholin-N-oxide (87.7 mg, 0.749 mmol), 4% of an aqueous solution of osmium tetroxide (153 μL, 0.0250 mmol) and water (2.0 mL) were added thereto at room temperature, followed by stirring for 4 hours. A saturated aqueous sodium thiosulfate solution was added to the reaction mixture, followed by extraction with ethyl acetate twice. The organic layer was washed with saturated brine, dried over anhydrous sodium sulfate, and concentrated under reduced pressure to yield a residue. The residue was purified by silica gel column chromatography to obtain compound 48 (121 mg, 58%) and compound 51 (3.3 mg, 2%).

Compound 48; ESI-MS: m/z 417 [M+H]+, 1H NMR (CDCl3) δ(ppm): 0.70 (s, 3H), 0.86 (d, J=6.6 Hz, 3H), 0.88 (d, J=6.6 Hz, 3H), 0.94 (d, J=6.3 Hz, 3H), 0.98-1.81 (m, 17H), 1.92-2.47 (m, 6H), 2.66-2.85 (m, 2H), 2.95 (dd, J=3.3, 13.6 Hz, 1H), 3.50-3.53 (m, 1H), 4.24-4.34 (m, 1H).

Compound 51; ESI-MS: m/z 417 [M+H]+, 1H NMR (CDCl3) δ(ppm): 0.70 (s, 3H), 0.86 (d, J=6.6 Hz, 3H), 0.88 (d, J=6.6 Hz, 3H), 0.94 (d, J=6.3 Hz, 3H), 0.98-1.87 (m, 17H), 1.92-2.40 (m, 6H), 2.57-2.70 (m, 3H), 3.74-3.82 (br s, 1H), 4.54 (d, J=10.6 Hz, 1H).

Example 40

(2R,3S,5S)-2,3-Dihydroxy-7-oxa-8-cholesten-6-one
(Compound 50) and (2R,3R,5S)-2,3-hydroxy-7-oxa-
8-cholesten-6-one (Compound 49)

Compound 48 (3.1 mg, 0.0074 mmol) obtained in Example 39 was dissolved in a mixed solvent of methanol (0.5 mL) and dichloromethane (0.25 mL), and sodium borohydride (0.6 mg, 0.015 mmol) was added thereto at 0° C., followed by stirring for 10 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain compound 50 (0.5 mg, 16%) and compound 49 (2.1 mg, 67%).

Compound 50; ESI-MS: m/z 419 [M+H]+, 1H NMR (CDCl3) δ(ppm): 0.67 (s, 3H), 0.86 (d, J=6.6 Hz, 3H), 0.88 (d, J=6.6 Hz, 3H), 0.94 (d, J=6.3 Hz, 3H), 0.98 (s, 3H), 1.01-2.39 (m, 22H), 2.88 (dd, J=3.3, 12.8 Hz, 1H), 3.80 (m, 1H), 4.09 (m, 1H).

Compound 49; ESI-MS: m/z 419 [M+H]+, 1H NMR (CDCl3) δ(ppm): 0.67 (s, 3H), 0.86 (d, J=6.6 Hz, 3H), 0.88 (d, J=6.6 Hz, 3H), 0.94 (d, J=6.3 Hz, 3H), 0.98-1.78 (m, 17H), 1.91-2.41 (m, 8H), 2.51 (dd, J=3.3, 12.8 Hz, 1H), 3.44 (m, 1H), 3.65 (m, 1H).

Example 41

(2R,3R,5S)-2-Hydroxy-3-methoxymethoxy-7-oxa-8-
cholesten-6-one (Compound 52)

Step 1; Compound 48 (570 mg, 1.37 mmol) obtained in Example 39 was dissolved in dichloromethane (10 mL), and imidazole (186 mg, 2.74 mmol) and chlorotriethylsilane (344 μL, 2.05 mmol) were added thereto at room temperature, followed by stirring for 5 hours. A saturated aqueous ammonium chloride solution was added to the reaction mixture, followed by extraction with chloroform twice. The organic layer was dried over anhydrous magnesium sulfate, and concentrated under reduced pressure to yield a residue. The residue was purified by silica gel column chromatography to obtain (2R,5S)-2-triethylsiloxy-7-oxa-8-cholesten-3,6-dione (676 mg, 93%).

ESI-MS: m/z 531 [M+H]+, 1H NMR (CDCl3) δ(ppm): 0.63 (q, J=8.1 Hz, 6H), 0.70 (s, 3H), 0.86 (d, J=6.6 Hz, 3H), 0.88 (d, J=6.6 Hz, 3H), 0.94 (d, J=6.3 Hz, 3H), 0.96 (t, J=8.1 Hz, 9H), 1.00-1.57 (m, 16H), 1.69-1.80 (m, 2H), 1.93-2.41 (m, 6H), 2.55-2.66 (m, 1H), 2.80 (m, 1H), 4.31 (m, 1H).

Step 2; (2R,5S)-2-Triethylsiloxy-7-oxa-8-cholesten-3,6-dione (37.2 mg, 0.0701 mmol) obtained in the Step 1 was dissolved in THF (1.0 mL), and sodium triacetoxyborohydride (29.7 mg, 0.140 mmol) was added thereof at room temperature, followed by stirring overnight. A saturated aqueous sodium bicarbonate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain (2R,3R,5S)-2-triethylsiloxy-3-hydroxy-7-oxa-8-cholesten-6-one (30.9 mg, 83%).

1H NMR (CDCl3) δ(ppm): 0.63 (q, J=8.1 Hz, 6H), 0.67 (s, 3H), 0.86 (d, J=6.6 Hz, 3H), 0.88 (d, J=6.6 Hz, 3H), 0.93 (d, J=6.6 Hz, 3H), 0.98 (t, J=8.1 Hz, 9H), 1.00-1.85 (m, 18H), 1.92-2.23 (m, 4H), 2.30-2.53 (m, 4H), 3.40 (m, 1H), 3.62 (m, 1H).

Step 3; (2R,3R,5S)-2-Triethylsiloxy-3-hydroxy-7-oxa-8-cholesten-6-one (5.9 mg, 0.011 mmol) obtained in the Step 2 was dissolved in dichloromethane (0.5 mL), and N,N-diisopropylethylamine (77.1 μL, 0.442 mmol) and chloromethylmethyl ether (13.5 μL, 0.177 mmol) were added thereto at room temperature, followed by stirring overnight. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain (2R,3R,5S)-2-triethylsiloxy-3-methoxymethoxy-7-oxa-8-cholesten-6-one (4.6 mg, 72%).

$^1$H NMR (CDCl$_3$) δ(ppm): 0.61 (q, J=8.1 Hz, 6H), 0.67 (s, 3H), 0.86 (d, J=6.6 Hz, 3H), 0.88 (d, J=6.6 Hz, 3H), 0.93 (d, J=6.6 Hz, 3H), 0.96 (t, J=8.1 Hz, 9H), 0.99 (s, 3H), 1.02-1.84 (m, 15H), 1.92-2.48 (m, 8H), 3.37 (m, 1H), 3.40 (s, 3H), 3.72 (m, 1H), 4.68 (d, J=6.6 Hz, 1H), 4.80 (d, J=6.6 Hz, 1H).

Step 4; By using (2R,3R,5S)-2-triethylsiloxy-3-methoxymethoxy-7-oxa-8-cholesten-6-one (4.6 mg, 0.00797 mmol) obtained in the Step 3, compound 52 (3.3 mg, 89%) was obtained in the same manner as the Step 4 of Example 19.

$^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.6 Hz, 3H), 0.99-1.78 (m, 18H), 1.92-2.48 (m, 8H), 3.29 (m, 1H), 3.44 (s, 3H), 3.58 (br s, 1H), 3.68 (m, 1H), 4.74 (d, J=7.0 Hz, 1H), 4.78 (d, J=7.0 Hz, 1H).

Example 42

(2R,3R,5S)-2,3-Dihydroxy-7-oxa-8-cholesten-6-one (Compound 53)

Step 1; (2R,3R,5S)-2-Triethylsiloxy-3-hydroxy-7-oxa-8-cholesten-6-one (30.9 mg, 0.0580 mmol) obtained in the Step 2 of Example 41 was dissolved in dichloromethane (1.0 mL), and 2,6-lutidine (20.2 μL, 0.174 mmol) and tert-butyldimethyl silyl trifluoromethanesulfonate (24.0 μL, 0.104 mmol) were added at 0° C., followed by stirring at room temperature for 15 minutes. A saturated aqueous sodium bicarbonate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain (2R,3R,5S)-2-triethylsiloxy-3-(tert-butyldimethylsiloxy)-7-oxa-8-cholesten-6-one (20.5 mg, 55%).

$^1$H NMR (CDCl$_3$) δ(ppm): 0.07 (s, 6H), 0.62 (q, J=8.1 Hz, 6H), 0.67 (s, 3H), 0.86 (d, J=6.6 Hz, 3H), 0.88 (d, J=6.6 Hz, 3H), 0.90 (s, 9H), 0.93 (d, J=6.3 Hz, 3H), 0.97 (t, J=8.1 Hz, 9H), 1.00 (s, 3H), 1.02-1.85 (m, 16H), 1.91-2.47 (m, 7H), 3.41 (m, 1H), 3.63 (m, 1H).

Step 2; By using (2R,3R,5S)-2-triethylsiloxy-3-(tert-butyldimethylsiloxy)-7-oxa-8-cholesten-6-one (7.5 mg, 0.012 mmol) obtained in the Step 1, (2R,3R,5S)-2-hydroxy-3-(tert-butyldimethylsiloxy)-7-oxa-8-cholesten-6-one (5.3 mg, 86%) was obtained in the same manner as the Step 3 of Example 19.

$^1$H NMR (CDCl$_3$) δ(ppm): 0.11 (s, 3H), 0.12 (s, 3H), 0.67 (s, 3H), 0.86 (d, J=6.6 Hz, 3H), 0.88 (d, J=6.6 Hz, 3H), 0.91 (s, 9H), 0.93 (d, J=6.3 Hz, 3H), 0.98-1.78 (m, 18H), 1.92-2.10 (m, 3H), 2.14-2.40 (m, 4H), 2.49 (dd, J=3.3, 12.8 Hz, 1H), 3.39 (m, 1H), 3.61 (m, 1H).

Step 3; (2R,3R,5S)-2-Hydroxy-3-(tert-butyldimethylsiloxy)-7-oxa-8-cholesten-6-one (12.0 mg, 0.0225 mmol) obtained in the Step 2 was dissolved in dichloromethane (1.0 mL), and 4-methylmorpholine N-oxide (5.3 mg, 0.045 mmol) and tetrapropylammonium perruthenate (1.6 mg, 0.045 mmol) were added thereto at room temperature, followed by stirring for 2 hours at room temperature. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain (3R,5S)-3-(tert-butyldimethylsiloxy)-7-oxa-8-cholesten-2,6-dione (11.0 mg, 92%).

$^1$H NMR (CDCl$_3$) δ(ppm): 0.03 (s, 3H), 0.14 (s, 3H), 0.66 (s, 3H), 0.86 (d, J=6.6 Hz, 3H), 0.88 (d, J=6.6 Hz, 3H), 0.90 (s, 9H), 0.93 (d, J=6.3 Hz, 3H), 0.94 (s, 3H), 1.01-1.59 (m, 14H), 1.76 (m, 1H), 1.93-2.18 (m, 5H), 2.38 (m, 1H), 2.67 (m, 1H), 2.98 (dd, J=3.6, 12.9 Hz, 1H), 4.22 (m, 1H).

Step 4; (3R,5S)-3-(Tert-butyldimethylsiloxy)-7-oxa-8-cholesten-2,6-dione (7.0 mg, 0.013 mmol) obtained in the Step 3 was dissolved in a mixed solvent of methanol (0.5 mL) and dichloromethane (0.25 mL), and sodium borohydride (1.5 mg, 0.040 mmol) was added thereto at 0° C., followed by stirring for 40 minutes at room temperature. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure. Compound 53 (2.5 mg, 45%) was obtained by using the resulting residue in the same manner as the Step 4 of Example 39.

ESI-MS: m/z 419 [M+H]$^+$, $^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.6 Hz, 3H), 0.98-1.78 (m, 19H), 1.85-2.43 (m, 9H), 3.72 (m, 1H), 4.07 (m, 1H).

Example 43

(3R,5S)-3-Hydroxy-7-oxa-8-cholesten-2,6-dione (Compound 54)

The title compound (2.8 mg, 70%) was obtained by using compound 52 (4.0 mg, 0.0087 mmol) obtained in the Step 4 of Example 41 in the same manner as the Step 3 of Example 42.

$^1$H NMR (CDCl$_3$) δ(ppm): 0.67 (s, 3H), 0.86 (d, J=6.6 Hz, 3H), 0.88 (d, J=6.6 Hz, 3H), 0.93 (d, J=6.3 Hz, 3H), 0.94 (s, 3H), 0.98-1.81 (m, 15H), 1.93-2.18 (m, 5H), 2.35 (m, 1H), 2.77 (m, 1H), 2.98 (dd, J=4.0, 12.9 Hz, 1H), 3.41 (s, 3H), 4.27 (m, 1H), 4.74 (s, 2H).

Example 44

(2R,5S)-2-Hydroxy-3-hydroxyimino-7-oxa-8-cholesten-6-one (Compound 55)

The title compound (10.2 mg, 68%) was obtained as a single geometric isomer by using compound 48 (14.6 mg, 0.0350 mmol) obtained in Example 39 in the same manner as Example 3.

$^1$H NMR (CDCl$_3$) δ(ppm): 0.69 (s, 3H), 0.86 (d, J=6.6 Hz, 3H), 0.88 (d, J=6.6 Hz, 3H), 0.93 (d, J=6.3 Hz, 3H), 0.94 (s, 3H), 0.98-1.82 (m, 16H), 1.91-2.40 (m, 6H), 2.57 (dd, J=4.3, 13.5 Hz, 1H), 2.98 (dd, J=4.0, 12.9 Hz, 1H), 3.78 (dd, J=4.6, 15.8 Hz, 1H), 4.39 (m, 1H).

Example 45

7-Oxa-1,4,8-cholestatrien-3,6-dione (Compound 57)

Compound 4 (5.8 mg, 0.015 mmol) obtained in Example 4 and N-fluorobenzenesulfonimide (6.0 mg, 0.019 mmol) were dissolved in THF (0.5 mL), and 1.0 mol/L of a lithium bis(trimethylsilyl)amide/THF solution (18.9 μL, 0.0189 mmol) was added thereto at 0° C., followed by stirring for 40 minutes. A saturated aqueous ammonium chloride solution was added to the reaction mixture, followed by extraction with ethyl acetate twice. The organic layer was washed with saturated brine, dried over anhydrous magnesium sulfate, and concentrated under reduced pressure to yield a residue. The residue was purified by preparative thin layer chromatography to obtain the title compound (1.9 mg, 33%).

ESI-MS: m/z 397 [M+H]$^+$, $^1$H NMR (CDCl$_3$) δ(ppm): 0.74 (s, 3H), 0.85 (d, J=6.6 Hz, 3H), 0.86 (d, J=6.6 Hz, 3H), 0.92 (d, J=6.3 Hz, 3H), 0.96-2.53 (m, 21H), 6.35 (m, 1H), 6.90 (m, 1H), 7.04 (d, J=10.2 Hz, 1H).

Example 46

3-(Methoxymethyloxy)-7-oxa-cholest-8(9)-en-6-one (Compound 56)

Compound P9 (48.5 mg, 0.105 mmol) obtained in Reference Example 9 was dissolved in acetic anhydride (3 mL), and sodium acetate (200 mg, 2.44 mmol) was added thereto, followed by stirring at 105° C. for 2 hours. After being left to cool, water was added to the reaction mixture, followed by extraction with ethyl acetate (20 mL×3). The organic layer was washed with water and saturated brine, and dried over anhydrous sodium sulfate. The residue obtained by concentration was purified by silica gel column chromatography (5 to 20% ethyl acetate/n-hexane) to obtain the title compound (16.2 mg, 35%).

$^1$H NMR δ(ppm, CDCl$_3$): 4.73-4.66 (2H, m), 3.53 (1H, m), 3.38 (3H, s), 2.37-1.01 (22H, m), 1.25 (3H, s), 0.97 (3H, s), 0.93 (3H, d, J=6.4 Hz), 0.87 (3H, d, J=6.6 Hz), 0.87 (3H, d, J=6.6 Hz), 0.68 (3H, s).

Example 47

20-(Acetyloxymethyl)-3-(methoxymethyloxy)-7-oxa-pregn-8(9)-en-6-one (Compound 58)

Compound P17 (45.3 mg, 0.100 mmol) obtained in Reference Example 17 was treated with sodium acetate (250 mg, 3.05 mmol) and acetic anhydride (1 mL) in the same manner as Example 46 to obtain the title compound (8.3 mg, 19%).

$^1$H NMR δ(ppm, CDCl$_3$): 4.71 (2H, m), 4.11 (1H, m), 3.72 (1H, m), 3.50 (1H, m), 3.38 (3H, s), 2.05 (3H, s), 2.50-1.10 (18H, m), 1.00 (3H, d, J=6.6 Hz), 0.95 (3H, s), 0.65 (3H, s).

Example 48

20-(Acetyloxymethyl)-7-oxa-pregn-8(9)-en-6-on-3-ol (Compound 77)

Compound P58 (8.3 mg, 0.019 mmol) obtained in Example 47 was treated with pyrimidium p-toluenesulfonate (14.4 mg, 0.0573 mmol) and tert-butanol (1 mL) in the same manner as Example 63 to obtain the title compound (1.2 mg, 16%).

$^1$H NMR δ(ppm, CDCl$_3$): 4.08 (1H, dd, J=10.8, 3.5 Hz), 3.79 (1H, dd, J=10.8, 7.5 Hz), 3.65 (1H, m), 2.39 (1H, dd, J=12.7, 3.3 Hz), 2.06 (3H, s), 2.33-1.25 (18H, m), 1.03 (3H, d, J=6.6 Hz), 0.97 (3H, s), 0.70 (3H, s).

Example 49

3-(Methoxymethyloxy)-7-oxa-cholest-8(9)-en-6-on-22-ol (Compound 60)

Compound P24 (3.7 mg, 0.0064 mmol) obtained in Reference Example 24 was dissolved in THF (1 mL), and a hydrogen fluoride-pyridine complex (0.5 mL) was added thereto, followed by stirring at room temperature for 20 minutes. A saturated aqueous sodium bicarbonate solution was added to the reaction mixture, followed by extraction with chloroform. The organic layer was washed with saturated brine, dried over anhydrous sodium sulfate, followed by purification by silica gel preparative thin layer chromatography (2:1 n-hexane-ethyl acetate) to obtain the title compound (2.3 mg, 78%).

$^1$H NMR δ(ppm, CDCl$_3$): 4.70 (2H, m), 3.62 (1H, m), 3.53 (1H, m), 3.38 (3H, s), 2.39-1.15 (24H, m), 0.97 (3H, s), 0.92 (3H, d, J=7.5 Hz), 0.90 (6H, d, J=6.6 Hz), 0.69 (3H, s).

Example 50

3-(Methoxymethyloxy)-7-oxa-cholest-8(9)-en-6,24-dione (Compound 61) and 3-(methoxymethyloxy)-7-oxa-cholest-8(14)-en-6,24-dione (Compound 92)

Compound P31 (17.7 mg, 0.0370 mmol) obtained in Reference Example 30 was treated with sodium acetate (100 mg, 0.209 mmol) and acetic acid (1 mL) in the same manner as Example 46 to obtain compound 61 (4.6 mg, 27%) and compound 92 (1.8 mg, 11%).

Compound 61; $^1$H NMR δ(ppm, CDCl$_3$): 4.73-4.66 (2H, m), 3.52 (1H, m), 3.38 (3H, s), 2.61 (1H, m), 2.52-1.19 (22H, m), 1.10 (3H, d, J=7.0 Hz), 1.09 (3H, d, J=6.8 Hz), 0.97 (3H, s), 0.93 (3H, d, J=6.2 Hz), 0.67 (3H, s).

Compound 92; $^1$H NMR δ(ppm, CDCl$_3$): 4.73-4.66 (2H, m), 3.53 (1H, m), 3.38 (3H, s), 2.61 (1H, m), 2.52-1.20 (22H, m), 1.09 (6H, d, J=6.8 Hz), 0.94 (3H, s), 0.93 (3H, d, J=6.6 Hz), 0.84 (3H, s).

Example 51

7-Oxa-cholest-8(9)-en-6,24-dion-3-ol (Compound 78)

Compound 61 (4.6 mg, 0.010 mmol) obtained in Example 50 was treated with pyrimidium p-toluenesulfonate (25 mg, 0.10 mmol) and tert-butanol (1 mL) in the same manner as Example 63 to obtain the title compound (2.6 mg, 63%).

$^1$H NMR δ(ppm, CDCl$_3$): 3.63 (1H, m), 2.61 (1H, m), 2.53-1.22 (23H, m), 1.09 (6H, d, J=7.0 Hz), 0.97 (3H, s), 0.93 (3H, d, J=6.4 Hz), 0.67 (3H, s).

Example 52

3-(Methoxymethyloxy)-7-oxa-cholest-8(9)-en-6-on-26-ol (Compound 62)

To an anhydrous THF solution (12.5 mL) containing compound P41 (16.7 mg, 0.0270 mmol) obtained in Reference Example 40 was added hydrogen fluoride-pyridine complex (1.0 mL), followed by stirring at room temperature for 30 minutes. The reaction mixture was poured into a saturated aqueous sodium bicarbonate solution, followed by extraction with chloroform. The organic layer was washed with saturated brine, dried over anhydrous sodium sulfate, and concentrated to yield a residue. The residue was purified by silica gel column chromatography (20 to 60% ethyl acetate/n-hexane) to obtain the title compound (10.8 mg, 87%).

$^1$H NMR δ(ppm, CDCl$_3$): 4.73-4.66 (2H, m), 3.57-3.40 (3H, m), 3.38 (3H, s), 2.37-1.25 (26H, m), 0.97 (3H, s), 0.93 (3H, d, J=6.4 Hz), 0.91 (3H, d, J=6.4 Hz), 0.67 (3H, s).

Example 53

7-Oxa-cholest-8(9)-en-6-on-3,26-diol (Compound 79) and 7-oxa-cholest-8(14)-en-6-on-3,26-diol (Compound 90)

To a tert-butanol solution (1 mL) containing compound 62 (1.5 mg, 0.0033 mmol) obtained in Example 52 was added pyrimidium p-toluenesulfonate (17.5 mg, 0.0696 mmol), followed by stirring at 100° C. for 3 hours. The reaction mixture was concentrated, followed by purification by silica gel preparative thin layer chromatography (chloroform-methanol (9:1)) to obtain compound 79 (0.6 mg, 49%) and compound 90 (0.5 mg, 41%).

Compound 79; $^1$H NMR δ(ppm, CDCl$_3$): 3.64 (1H, m), 3.53-3.40 (2H, m), 2.39 (1H, dd, J=12.7, 3.5 Hz), 2.33-1.00 (26H, m), 0.97 (3H, s), 0.94 (3H, d, J=6.0 Hz), 0.92 (3H, d, J=6.6 Hz), 0.67 (3H, s).

Compound 90; $^1$H NMR δ(ppm, CDCl$_3$): 3.64 (1H, m), 3.53-3.43 (2H, m), 2.43-1.00 (27H, m), 0.93 (3H, d, J=6.5 Hz), 0.92 (3H, s), 0.91 (3H, d, J=6.5 Hz), 0.84 (3H, s).

Example 54

3-(Methoxymethyloxy)-7-oxa-cholest-8(9)-en-6-on-26-al (Compound 63)

To a dichloromethane solution (2 mL) containing compound 62 (10.8 mg, 0.0234 mmol) obtained in Example 52, Molecular Sieves 4 Å (200 mg), 4-methylmorpholin-N-oxide (10 mg, 0.085 mmol) and tetrapropylammonium perruthenate (3.0 mg, 0.0085 mmol) were added, followed by stirring at room temperature for 15 minutes. The reaction mixture was filtered, and the filtrate was concentrated, followed by purification by silica gel column chromatography (20 to 50% ethyl acetate/n-hexane) to obtain the title compound (4.5 mg, 42%).

$^1$H NMR δ(ppm, CDCl$_3$): 9.61 (1H, d, J=2.0 Hz), 4.73-4.66 (2H, m), 3.52 (1H, m), 3.38 (3H, s), 2.37-1.23 (25H, m), 1.09 (3H, d, J=7.0 Hz), 0.97 (3H, s), 0.93 (3H, d, J=6.4 Hz), 0.67 (3H, s).

Example 55

3-(Methoxymethyloxy)-7-oxa-cholest-8(9)-en-6-on-26-oic acid (Compound 64)

Compound 63 (4.5 mg, 0.0098 mmol) obtained in Example 54, 2-methyl-2-butene (50 μL, 0.47 mmol) and sodium dihydrogenphosphate (20 mg, 0.13 mmol) were dissolved in a mixed solvent of tert-butanol (2 mL) and water (0.5 mL), and sodium chlorite (80%; 20 mg, 0.18 mmol) was added thereto, followed by stirring for 15 minutes. The reaction mixture was poured into a saturated aqueous ammonium chloride solution, followed by extraction with chloroform (10 mL×3). The organic layer was dried over anhydrous sodium sulfate, and concentrated, followed by purification by silica gel column chromatography (5 to 10% methanol/chloroform) to obtain the title compound (2.9 mg, 62%).

$^1$H NMR δ(ppm, CDCl$_3$): 4.73-4.66 (2H, m), 3.52 (1H, m), 3.38 (3H, s), 2.51-1.25 (26H, m), 1.18 (3H, d, J=7.0 Hz), 0.97 (3H, s), 0.93 (3H, d, J=6.6 Hz), 0.67 (3H, s).

Example 56

7-Oxa-3-hydroxy-cholest-8(9)-en-6-on-26-acid (Compound 80)

To a tert-butanol solution containing compound 64 (2.9 mg, 0.0061 mmol) obtained in Example 55 was added pyrimidium p-toluenesulfonate (5.0 mg, 0.020 mmol), followed by stirring at 110° C. for 2.5 hours. The reaction mixture was concentrated, followed by purification by silica gel preparative thin layer chromatography (chloroform-methanol (9:1)) to obtain the title compound (1.1 mg, 42%).

$^1$H NMR δ(ppm, CDCl$_3$): 3.64 (1H, m), 2.48-1.25 (27H, m), 1.18 (3H, d, J=6.8 Hz), 0.95 (3H, d, J=7.0 Hz), 0.92 (3H, s), 0.67 (3H, s).

Example 57 tert-Butyl 3-(methoxymethyloxy)-20-carboxy-7-oxa-pregna-8(14)-en-6-on-22-ate (Compound 59)

Compound P45 (30.1 mg, 0.0627 mmol) obtained in Reference Example 44 was treated with sodium acetate (205 mg, 2.50 mmol) and acetic anhydride (1 mL) in the same manner as Example 46 to obtain the title compound (8.8 mg, 30%).

$^1$H NMR δ(ppm, CDCl$_3$): 4.69 (2H, m), 3.52 (1H, m), 3.38 (3H, s), 2.39-2.12 (5H, m), 1.99-1.86 (2H, m), 1.81-1.61 (2H, m), 1.56-1.45 (9H, m), 1.44 (9H, s), 1.16 (3H, d, J=6.8 Hz), 0.97 (3H, s), 0.68 (3H, s).

Example 58 tert-Butyl 20-carboxy-7-oxa-pregna-8(14)-en-6-on-22-ate (Compound 87)

Compound 59 (2.6 mg, 0.0056 mmol) obtained in Example 57 was treated with pyrimidium p-toluenesulfonate (14.5 mg, 0.0577 mmol) and tert-butanol (1 mL) in the same manner as Example 63 to obtain the title compound (1.3 mg, 55%).

$^1$H NMR δ(ppm, CDCl$_3$): 3.63 (1H, m), 2.44 (1H, dd, J=12.5, 3.3 Hz), 2.34-2.22 (2H, m), 2.00-1.80 (2H, m), 1.76-1.60 (2H, m), 1.59-1.25 (12H, m), 1.44 (9H, s), 1.16 (3H, d, J=6.8 Hz), 0.97 (3H, s), 0.68 (3H, s).

Example 59

20-Carboxy-7-oxa-pregna-8(14)-en-6-on-22-acid (Compound 88)

Compound 59 (8.8 mg, 0.019 mmol) obtained in Example 57 was dissolved in dichloromethane (2 mL), and a dichloromethane solution (0.2 mL) of B-bromocatecholborane (9.0 mg, 0.045 mmol) was added thereto, followed by stirring at room temperature for 69 hours. Water was added to the reaction mixture, followed by extraction with chloroform. The organic layer was washed with saturated brine, dried over anhydrous sodium sulfate, followed by purification by silica gel preparative thin layer chromatography (chloroform-methanol (10:1)) to obtain the title compound (6.0 mg, 87%).

$^1$H NMR δ(ppm, CDCl$_3$): 3.64 (1H, m), 2.58-2.21 (4H, m), 1.97-1.39 (16H, m), 1.26 (3H, d, J=7.0 Hz), 0.96 (3H, s), 0.85 (3H, s).

Example 60

20-Carboxy-7-oxa-pregna-8(14)-en-6-on-22-acid tert-butyl N-(2-aminoethyl)carbamate (Compound 89)

Compound 88 (1.3 mg, 0.0036 mmol) obtained in Example 59, N-(tert-butoxycarbonyl)ethylene diamine (1.5 mg, 0.0094 mmol), 1-hydroxybenzotriazole (3.0 mg, 0.022 mmol) and triethylamine (1.0 μL, 0.0072 mmol) were dissolved in dichloromethane (1.2 mL), and N-(3-dimethylaminopropyl)-N'-ethylcarbodiimide hydrochloride (2.0 mg, 0.010 mmol) was added thereto, followed by stirring at room temperature for 20 hours. A saturated aqueous ammonium chloride solution was added to the reaction mixture, followed by extraction with chloroform. The organic layer was washed with saturated brine, dried over anhydrous sodium sulfate, and concentrated to yield a residue. The residue was purified by silica gel preparative thin layer chromatography (chloroform-methanol (10:1)) to obtain the title compound (1.5 mg, 83%).

$^1$H NMR δ(ppm, CDCl$_3$): 6.18 (1H, br s), 4.89 (1H, br s), 3.65 (1H, m), 3.37-3.25 (4H, m), 2.52-2.38 (2H, m), 2.26-2.21 (3H, m), 2.12 (1H, m), 2.07-1.25 (13H, m), 1.44 (9H, s), 1.19 (3H, d, J=6.8 Hz), 0.93 (3H, s), 0.84 (3H, s).

Example 61

7-Oxa-ergosta-8(9)-en-6-on-3-ol (Compound 76)

7-Oxa-ergosta-8(9),24(28)-dien-6-on-3-ol (4.0 mg, 0.0097 mmol) obtained in Reference Example 85 was dissolved in ethyl acetate (2 mL), and 10% palladium-carbon (2.4 mg) was added thereto, followed by stirring at room temperature for 1 hour under a hydrogen atmosphere. The catalyst was separated by filtration, and the filtrate was concentrated to obtain the title compound (3.6 mg, 90%).

$^1$H NMR δ(ppm, CDCl$_3$): 3.63 (1H, m), 2.39 (1H, dd, J=12.7, 3.3 Hz), 2.33-1.00 (24H, m), 0.97 (3H, s), 0.93 (3H, d, J=6.4 Hz), 0.85 (3H, d, J=6.6 Hz), 0.78 (3H, d, J=7.0 Hz), 0.77 (3H, d, J=7.0 Hz), 0.67 (3H, s).

Example 62

3-(Acetyloxy)-7-oxa-ergosta-8(9)-en-6-one (Compound 91)

Compound P50 (24.0 mg, 0.0504 mmol) obtained in Reference Example 49 was dissolved in acetic anhydride (1 mL), and sodium acetate (150 mg, 1.83 mmol) was added thereto, followed by stirring at 90° C. to 95° C. for 1 hour. The reaction mixture was cooled to room temperature, followed by adding ethyl acetate (5 mL) then filtration. Water was added to the filtrate, followed by extraction with ethyl acetate (20 mL×2). The organic layer was washed with a saturated aqueous sodium bicarbonate solution and saturated brine, and dried over anhydrous magnesium sulfate, followed by purification by silica gel column chromatography (5 to 15% ethyl acetate/n-hexane) to obtain the title compound 7 (13.7 mg, 59%).

$^1$H NMR δ(ppm, CDCl$_3$): 4.71 (1H, m), 2.43 (1H, dd, J=13.0, 3.3 Hz), 2.35-1.90 (4H, m), 2.04 (3H, s), 1.74-1.19 (19H, m), 0.98 (3H, s), 0.94 (3H, d, J=6.4 Hz), 0.86 (3H, d, J=7.0 Hz), 0.78 (6H, d, J=6.8 Hz), 0.67 (3H, s).

Example 63

(1R,3aR,5aS,7S,9aS,11aR)-7-Methoxymethoxy-1-[(S)-1-methoxypropan-2-yl]-9a,11a-dimethyl-1,2,3,3a,5a,6,7,8,9,9a,11,11a-dodecahydrobenzo[c]cyclopenta[h]chromen-5(10H)-one (Compound 67)

Compound P55 (1.47 g) obtained in Reference Example 54 was dissolved in acetic anhydride (53 mL), and sodium acetate (326 mg, 3.97 mmol) was added thereto, followed by stirring at 105° C. for 2 hours. The reaction mixture was left to cool, and then a saturated aqueous ammonium chloride solution was added, followed by extraction with ethyl acetate (50 mL×3). The organic layer was washed with water and saturated brine, and dried over anhydrous sodium sulfate. The residue obtained by concentration was purified by silica gel column chromatography (5 to 20% ethyl acetate/n-hexane) to obtain the title compound (582 mg, 54% (2 steps)).

$^1$H NMR δ(ppm, CDCl$_3$): 4.69 (2H, m), 3.51 (1H, m), 3.38 (3H, s), 3.33 (1H, m), 3.32 (3H, s), 3.14 (1H, dd, J=6.8 Hz, 15.8 Hz), 2.38-1.21 (18H, m), 1.05 (3H, d, J=6.6 Hz), 0.97 (3H, s), 0.69 (3H, s).

Example 64

(1R,3aR,5aS,7S,9aS,11aR)-7-Hydroxy-1-[(S)-1-methoxypropan-2-yl]-9a,11a-dimethyl-1,2,3,3a,5a,6,7,8,9,9a,11,11a-dodecahydrobenzo[c]cyclopenta[h]chromen-5(10H)-one (Compound 82)

Compound 67 (581.6 mg, 1.431 mmol) obtained in Example 63 was dissolved in tert-butanol (48 mL), and pyrimidium p-toluenesulfonate (3.6 g; 14 mmol) was added thereto, followed by stirring at 105° C. for 4 hours. The reaction mixture was cooled to 0° C., a saturated aqueous ammonium chloride solution was added, followed by extraction with ethyl acetate (50 mL×3). The organic layer was washed with saturated brine, dried over anhydrous magnesium sulfate, and concentrated to yield a residue. The residue was purified by silica gel column chromatography, followed by purification by high-speed liquid chromatography (60 to 100% acetonitrile/water) to obtain the title compound (150 mg, 29%).

$^1$H NMR δ(ppm, CDCl$_3$): 3.63 (1H, m), 3.35-3.30 (1H, m), 3.32 (3H, s), 3.14 (1H, dd, J=6.8 Hz, 16 Hz), 2.40-1.36 (19H, m), 1.05 (3H, d, J=6.4 Hz), 0.97 (3H, s), 0.69 (3H, s).

Example 65

(1R,3aR,5aS,7S,9aS,11aR)-1-[(S)-1-Isobutoxypropan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 65) A crude product (2.34 g) of compound P63 obtained in Reference Example 62 was treated with sodium acetate (520 mg, 6.34 mmol) in the same manner as Reference Example 46 to obtain the title compound (1.10 g).

Example 66

(1R,3aR,5aS,7S,9aS,11aR)-7-Hydroxy-1-[(S)-1-isobutyloxypropan-2-yl]-9a,11a-dimethyl-1,2,3,3a,5a,6,7,8,9,9a,11,11a-dodecahydrobenzo[c]cyclopenta[h]chromen-5(10H)-one (Compound 81)

Compound 65 (1.10 g) obtained in Example 65 was treated with pyrimidium p-toluenesulfonate (5.3 g, 21 mmol) in the same manner as Example 63 to obtain the title compound (134 mg, 8.5%).

$^1$H NMR δ(ppm, CDCl$_3$): 3.64 (1H, m), 3.37 (1H, dd, J=3.1 Hz, 9.0 Hz), 3.22-3.05 (3H, m), 2.42-1.25 (19H, m), 1.05 (3H, d, J=6.6 Hz), 0.97 (3H, s), 0.89 (6H, dd, J=2.4 Hz, 6.6 Hz), 0.69 (3H, s).

Example 67

(1R,3aR,5aS,7S,9aS,11aR)-7-Hydroxy-1-[(S)-1-hydroxypropan-2-yl]-9a,11a-dimethyl-1,2,3,3a,5a,6,7,8,9,9a,11,11a-dodecahydrobenzo[c]cyclopenta[h]chromen-5(10H)-one (Compound 95)

Compound P85 (126.8 mg, 0.2310 mmol) obtained in Reference Example 66 was dissolved in THF (8 mL), and acetic acid (2.4 mL, 42 mmol) and 1.0 mol/L of a tetrabutylammoniumfluoride-THF solution (10.5 mL, 10.5 mmol) were added thereto, followed by stirring at room temperature for 6 days. A saturated aqueous sodium bicarbonate solution which had been cooled to 0° C. was added to the reaction mixture, followed by extraction with ethyl acetate (30 mL×3). The organic layer was washed with saturated sodium chloride, dried over anhydrous magnesium sulfate, and concentrated to yield a residue. The residue was purified by silica gel column chromatography (33% to 200% ethyl acetate/n-hexane) to obtain the title compound (71 mg, 79%).

$^1$H NMR δ(ppm, CDCl$_3$): 4.74-4.65 (2H, m), 3.65 (1H, dd, J=3.1 Hz, 10.5 Hz), 3.52 (1H, m), 3.42-3.38 (4H, m), 2.38-1.22 (19H, m), 1.07 (3H, d, J=6.6 Hz), 0.97 (3H, s), 0.70 (3H, s).

Example 68

(1R,3aR,5aS,7S,9aS,11aR)-1-[(S)-1-Allyloxypropan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 66)

Compound 95 (16.7 mg, 0.0425 mmol) obtained in Example 67 was dissolved in allylbromide (2 mL), and silver oxide (986 mg, 4.25 mmol) was added thereto, followed by stirring under light shading at room temperature for 14 hours. Silver oxide was separated by filtration, the filtrate was concentrated, and the residue was purified by silica gel column chromatography (33% ethyl acetate/n-hexane) to obtain the title compound (3.7 mg, 21%).

$^1$H NMR δ(ppm, CDCl$_3$): 5.93 (1H, m), 5.32-5.15 (2H, m), 4.73-4.66 (2H, m), 3.96 (1H, d, J=5.7 Hz), 3.94 (1H, d, J=5.9 Hz), 3.50 (1H, m), 3.36 (3H, s), 3.35 (1H, m), 3.17 (1H, dd, J=7.3 Hz, 9.0 Hz), 2.30-1.13 (18H, m), 1.07 (3H, d, J=6.6 Hz), 0.97 (3H, s), 0.88 (3H, s).

Example 69

(1R,3aR,5aS,7S,9aS,11aR)-7-Methoxymethoxy-9a,11a-dimethyl-1-[(S)-1-propoxypropan-2-yl]-1,2,3,3a,5a,6,7,8,9,9a,11,11a-dodecahydrobenzo[c]cyclopenta[h]chromen-5(10H)-one (Compound 68)

Compound 66 (3.7 mg, 0.0086 mmol) obtained in Example 68 was dissolved in ethyl acetate (2 mL), and 10% palladium-carbon (2.0 mg) was added thereto, followed by stirring at room temperature for 2 hours under a hydrgen atmosphere. The catalyst was sparated by filtration, followed by concentrating the filtrate to obtain the title compound (2.8 mg, 76%).

$^1$H NMR δ(ppm, CDCl$_3$): 4.66-4.60 (2H, m), 3.32 (1H, m), 3.20 (3H, s), 3.30-3.18 (3H, m), 3.02 (1H, dd, J=7.7 Hz, J=9.2 Hz), 2.32-1.15 (20H, m), 0.98 (3H, d, J=6.4 Hz), 0.87 (3H, s), 0.84 (3H, t, J=7.3 Hz), 0.62 (3H, s).

Example 70

(1R,3aR,5aS,7S,9aS,11aR)-7-Methoxymethoxy-9a,11a-dimethyl-1-[(S)-1-(2-methylallyloxy)propan-2-yl]-1,2,3,3a,5a,6,7,8,9,9a,11,11a-dodecahydrobenzo[c]cyclopenta[h]chromen-5(10H)-one (Compound 96)

Compound 95 (7.6 mg, 0.019 mmol) obtained in Example 67 was dissolved in allylbromide (0.5 mL), and silver oxide (986 mg, 4.25 mmol) was added thereto, followed by stirring under light shading at room temperature for 12 hours. Silver oxide was separated by filtration, the filtrate was concentrated, and then the residue was purified by silica gel column chromatography (33% ethyl acetate/n-hexane) to obtain the title compound (4.2 mg, 48%).

$^1$H NMR δ(ppm, CDCl$_3$): 5.68 (1H, s), 5.10 (1H, s), 4.95-4.88 (2H, m), 4.75-4.65 (2H, m), 3.90-3.80 (2H, m), 3.52 (1H, m), 3.38 (3H, s), 3.36-3.11 (2H, m), 2.37-1.25 (19H, m), 1.07 (3H, d, J=6.6 Hz), 0.97 (3H, s), 0.69 (3H, s).

Example 71

(1R,3aR,5aS,7S,9aS,11aR)-1-[(2S)-1-(3-Hydroxy-2-methylpropoxy)propane-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 70)

Compound P70 (13.6 mg, 0.0219 mmol) obtained in Reference Example 73 was treated with 1.0 mol/L of a tetrabutylammonium fluoride-THF solution and acetic acid in the same manner as Reference Example 3 to obtain the title compound (8.6 mg, 84%).

$^1$H NMR δ(ppm, CDCl$_3$): 4.75-4.65 (2H, m), 3.38 (3H, s), 3.61-3.15 (7H, m), 2.81 (1H, m), 2.37-1.32 (19H, m), 1.04 (3H, d, J=6.6 Hz), 0.97 (3H, s), 0.86 (3H, dd, J=2.2 Hz, 7.0 Hz), 0.68 (3H, s).

Example 72

(1R,3aR,5aS,7S,9aS,11aR)-1-[(29-1-(3-Methoxy-2-methylpropoxy)propan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 71)

Compound 70 (15.1 mg, 0.0325 mmol) obtained in Example 71 was treated with silver oxide (1.50 g, 6.49 mmol) and methyl iodide (3.0 mL) instead of allylbromide in the same manner as Example 67 to obtain the title compound (6.3 mg, 40%).

$^1$H NMR δ(ppm, CDCl$_3$): 4.75-4.65 (2H, m), 3.52 (1H, m), 3.38 (3H, s), 3.33 (3H, s), 3.37-3.08 (6H, m), 2.37-1.25 (19H, m), 1.04 (3H, d, J=6.4 Hz), 0.97 (3H, s), 0.94 (3H, d, J=6.8 Hz), 0.69 (3H, s).

Example 73

(R)-[(1R,3aR,5aS,7S,9aS,11aR)-7-Methoxymethoxy-9a,11a-dimethyl-5-oxo-1,2,3,3a,5,5a,6,7,8,9,9a,10,11,11a-tetradecahydrobenzo[c]cyclopenta[h]chromen-1-yl]octyl acetate (Compound 73)

Compound P78 (17.8 mg, 0.0340 mmol) obtained in Reference Example 81 was dissolved in dichloromethane (3.4 mL), and triethylamine (20.0 μL, 0.143 mmol) and carbonyldiimidazole (8.3 mg, 0.051 mmol) were added thereto, followed by stirring at room temperature for 11 hours. A saturated aqueous ammonium chloride solution was added thereto, followed by extraction with ethyl acetate (20 mL×3). The organic layer was washed with saturated brine, dried over anhydrous magnesium sulfate, and concentrated to yield a residue. The residue was purified by silica gel column chromatography (33% ethyl acetate/n-hexane) to obtain the title compound (7.0 mg, 41%).

$^1$H NMR δ(ppm, CDCl$_3$): 4.75-4.65 (2H, m), 3.52 (1H, m), 3.38 (3H, s), 2.37-0.85 (33H, m), 0.97 (3H, s), 0.93 (3H, d, J=6.6 Hz), 0.67 (3H, s).

Example 74

(R)-[(1R,3aR,5aS,7S,9aS,11aR)-7-Hydroxy-9a,11a-dimethyl-5-oxo-1,2,3,3a,5,5a,6,7,8,9,9a,10,11,11a-tetradecahydrobenzo[c]cyclopenta[h]chromen-1-yl] octyl acetate (Compound 97)

Compound 73 (7.0 mg, 0.014 mmol) obtained in Example 73 was treated with pyrimidium p-toluenesulfonate (35 mg, 0.14 mmol) in the same manner as Example 63 to obtain the title compound (1.9 mg, 30%).
$^1$H NMR δ(ppm, CDCl$_3$): 4.05 (2H, t, J=6.8 Hz), 3.64 (1H, m), 2.42-1.12 (32H, m), 0.97 (3H, s), 0.93 (3H, d, J=6.4 Hz), 0.67 (3H, s).

Example 75

(1R,3aR,5aS,7S,9aS,11aR)-1-[(R)-8-Hydroxyoctan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 74)

Compound P81 (6.2 mg, 0.011 mmol) obtained in Reference Example 84 was dissolved in THF (2 mL), water (0.5 mL) and trifluoroacetic acid (0.5 mL), followed by stirring at 0° C. for 2 hours. Water was added to the reaction mixture, followed by extraction with ethyl acetate (5 mL×3). The organic layer was dried over anhydrous magnesium sulfate, and concentrated to yield a residue. The residue was purified by silica gel column chromatography (33% ethyl acetate/n-hexane) to obtain the title compound (5.1 mg, 100%).
$^1$H NMR δ(ppm, CDCl$_3$): 4.72-4.68 (2H, m), 3.64 (2H, t, J=6.6 Hz), 3.50 (1H, m), 3.38 (3H, s), 2.39-1.20 (31H, m), 0.97 (3H, s), 0.93 (3H, d, J=6.6 Hz), 0.67 (3H, s).

Example 76

(1R,3aR,5aS,7S,9aS,11aR)-1-[(R)-8-Azideoctan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 98)

Compound 74 (7.3 mg, 0.016 mmol) obtained in Example 75 was dissolved in toluene (2 mL), and triphenylphosphine (21 mg, 0.079 mmol), diphenylphosphoryl azide (17 μL, 0.079 mmol) and diethyl azodicarboxylate (17 μL, 0.079 mmol) were added thereto, followed by stirring at room temperature for 3 hours. Water was added to the reaction mixture, followed by extraction with ethyl acetate (5 mL×3). The organic layer was washed with saturated brine, dried over anhydrous magnesium sulfate, and concentrated to yield a residue. The residue was purified by silica gel column chromatography (33% ethyl acetate/n-hexane) to obtain the title compound (5.1 mg, 66%).
$^1$H NMR δ(ppm, CDCl$_3$): 4.72-4.68 (2H, m), 3.52 (1H, m), 3.38 (3H, s), 3.26 (2H, t, J=6.8 Hz), 2.37-1.20 (28H, m), 0.97 (3H, s), 0.93 (3H, d, J=6.4 Hz), 0.67 (3H, s).

Example 77

(R)-7-[(1R,3aR,5aS,7S,9aS,11aR)-7-Methoxymethoxy-9a,11a-dimethyl-5-oxo-1,2,3,3a,5,5a,6,7,8,9,9a,10,11,11a-tetradecahydrobenzo[c]cyclopenta[h]chromen-1-yl]octyl carbamate (Compound 75)

Compound 98 (5.1 mg, 0.011 mmol) obtained in Example 76 was dissolved in ethyl acetate (3 mL), and di-tert-butyldicarbonate (11.0 mg, 0.0525 mmol) and catalytic amount of 10% palladium-carbon were added thereto, followed by stirring at room temperature for 2 hours under a hydrogen atmosphere. The catalyst was separated by filtration, and the filtrate was concentrated to yield a residue. The residue was purified by silica gel column chromatography (25% ethyl acetate/n-hexane) to obtain the title compound (3.7 mg, 63%).
$^1$H NMR δ(ppm, CDCl$_3$): 4.72-4.68 (2H, m), 4.49 (1H, br s), 3.52 (1H, m), 3.38 (3H, s), 3.15-3.05 (2H, m), 2.37-1.22 (37H, m), 0.97 (3H, s), 0.92 (3H, d, J=6.4 Hz), 0.67 (3H, s).

Example 78

(1R,3aR,3bR,5aS,9aR,9bR,11aR)-9a,11a-Dimethyl-1-[(R)-6-methylheptan-2-yl]dodecahydrobenzo[c]cyclopenta[h]chromen-5,7(3bH,8H)-dione (Compound 93)

Step 1; Commercially available 7-dehydrocholesterol (18.3 g, 47.6 mmol) was dissolved in dichloromethane (150 mL), and N,N-diisopropylethylamine (24.9 mL, 143 mmol) and chloromethylmethyl ether (7.23 mL, 95.2 mmol) were added thereto at room temperature, followed by stirring overnight. A saturated aqueous ammonium chloride solution was added to the reaction mixture, followed by extraction with chloroform twice. The organic layer was washed with saturated brine, dried over anhydrous magnesium sulfate, and concentrated under reduced pressure to yield a residue. The residue was purified by silica gel column chromatography to obtain (S)-3-methoxymethoxy-5,7-cholestadiene (18.1 g, 89%).
$^1$H NMR (CDCl$_3$) δ(ppm): 0.62 (s, 3H), 0.87 (d, J=7.0 Hz, 3H), 0.87 (d, J=7.0 Hz, 3H), 0.94 (d, J=6.4 Hz, 3H), 0.94 (s, 3H), 0.95-2.03 (m, 22H), 2.09 (d, J=12.6 Hz, 1H), 2.32 (m, 1H), 2.52 (d, J=12.1 Hz, 1H), 3.38 (s, 3H), 3.50 (m, 1H), 4.71 (s, 2H), 5.38 (d, J=3.3 Hz, 1H), 5.57 (d, J=3.3 Hz, 1H).

Step 2; By using (S)-3-methoxymethoxy-5,7-cholestadiene (18.1 g, 42.2 mmol) obtained in the Step 1, (3S,5S,6S)-3-methoxymethoxy-7-cholesten-6-ol (13.9 g, 74%) was obtained in the same manner as Reference Example 2.
$^1$H NMR (CDCl$_3$) δ(ppm): 0.54 (s, 3H), 0.85 (s, 3H), 0.87 (d, J=7.0 Hz, 3H), 0.87 (d, J=7.0 Hz, 3H), 0.92 (d, J=6.4 Hz, 3H), 0.95-1.95 (m, 26H), 2.05 (m, 1H), 2.30 (m, 1H), 3.38 (s, 3H), 3.51 (m, 1H), 4.66-4.73 (m, 2H), 5.18 (s, 1H).

Step 3; By using (3S,5S,6S)-3-methoxymethoxy-7-cholesten-6-ol (21.4 g, 47.9 mmol) obtained in the Step 2, (3S,5S)-3-methoxymethoxy-7-cholesten-6-one (20.1 g, 94%) was obtained in the same manner as Reference Example 4.
$^1$H NMR (CDCl$_3$) δ(ppm): 0.60 (s, 3H), 0.87 (d, J=7.0 Hz, 3H), 0.87 (s, 3H), 0.87 (d, J=7.0 Hz, 3H), 0.94 (d, J=6.4 Hz, 3H), 0.95-2.37 (m, 26H), 3.38 (s, 3H), 3.53 (m, 1H), 4.69 (d, J=18.1 Hz, 1H), 4.71 (d, J=18.1 Hz, 1H), 5.73 (s, 1H).

Step 4; Sodium periodate (5.74 g, 26.8 mmol) and cerium chloride heptahydrate (1.67 g, 4.48 mmol) were dissolved in water (54 mL), ethyl acetate (108 mL), acetonitrile (108 mL) and (3S,5S)-3-methoxymethoxy-7-cholestene-6-one (2.00 g, 4.48 mmol) obtained in the Step 3 were added thereto and cooled to 0° C., and then ruthenium chloride hydrate (278 mg, 1.34 mmol) was added thereto, followed by stirring for 1 hour. A saturated aqueous sodium thiosulfate solution was added to the reaction mixture, followed by extraction with ethyl acetate five times. The organic layer was washed with saturated brine, dried over anhydrous magnesium sulfate, and concentrated under reduced pressure to yield a residue. The residue was purified by silica gel column chromatography to obtain a crude product (1.70 g) of (3S,5S,7S,8S)-3-methoxymethoxy-7,8-dihydroxycholestan-6-one. This was dissolved in a mixed solvent of toluene (215 mL) and methanol (21 mL), and lead tetraacetate (4.72 g, 10.7 mmol) was added thereto at 0° C., followed by stirring for 80 minutes. A saturated aqueous sodium thiosulfate solution was added to the reaction mixture, followed by extraction with ethyl acetate twice. The organic layer was washed with saturated brine, dried over anhydrous magnesium sulfate, and concentrated under reduced pressure to yield a residue. The residue was purified by silica gel column chromatography to obtain (1S, 2R,5S)methyl 5-methoxymethoxy-2-methyl-2-[(1R,3aR, 5R,7aR)-7a-methyl-1-[(R)-6-methylheptan-2-yl]-4-oxooctahydro-1H-inden-5-yl]cyclohexanecarboxylate (937 mg, 44%).

$^1$H NMR (CDCl$_3$) δ(ppm): 0.59 (s, 3H), 0.85 (d, J=7.0 Hz, 3H), 0.88 (d, J=7.0 Hz, 3H), 0.93 (d, J=5.7 Hz, 3H), 0.96-2.02 (m, 23H), 2.09-2.21 (m, 2H), 2.25-2.40 (m, 3H), 2.69 (dd, J=3.6, 12.8 Hz, 1H), 3.36 (s, 3H), 3.45 (m, 1H), 3.64 (s, 3H), 4.66 (s, 2H).

Step 5; (1S,2R,5S)Methyl 5-methoxymethoxy-2-methyl-2-[(1R,3aR,5R,7aR)-7a-methyl-1-[(R)-6-methylheptan-2-yl]-4-oxooctahydro-1H-inden-5-yl]cyclohexanecarboxylate (19.8 mg, 0.0414 mmol) obtained in the Step 4 was dissolved in tert-butyl alcohol (0.414 mL), and pyrimidium p-toluenesulfonate (104 mg, 0.414 mmol) was added thereto at room temperature, followed by heating under reflux for 4 hours. The reaction mixture was cooled to room temperature, and then a saturated aqueous sodium bicarbonate solution was added, followed by extraction with ethyl acetate three times. The organic layer was washed with saturated brine, dried over anhydrous magnesium sulfate, and concentrated under reduced pressure to yield a residue. The residue was purified by preparative thin layer chromatography to obtain (1S,2R,5S)methyl 5-hydroxy-2-methyl-2-[(1R,3aR,5R, 7aR)-7a-methyl-1-[(R)-6-methylheptan-2-yl]-4-oxooctahydro-1H-inden-5-yl]cyclohexanecarboxylate (7.2 mg, 40%).

$^1$H NMR (CDCl$_3$) δ(ppm): 0.59 (s, 3H), 0.85 (d, J=7.0 Hz, 3H), 0.88 (d, J=7.0 Hz, 3H), 0.93 (d, J=6.2 Hz, 3H), 0.98-2.31 (m, 26H), 2.37-2.50 (m, 2H), 2.86 (m, 1H), 3.57 (m, 1H), 3.66 (s, 3H).

Step 6; (1S,2R,5S)Methyl 5-hydroxy-2-methyl-2-[(1R, 3aR,5R,7aR)-7a-methyl-1-[(R)-6-methylheptan-2-yl]-4-oxooctahydro-1H-inden-5-yl]cyclohexanecarboxylate (365 mg, 0.840 mmol) obtained in the Step 5 was dissolved in toluene (8.0 mL), and 1.0 mol/L of a diisobutylaluminum hydride/toluene solution (2.94 mL, 2.94 mmol) was added thereto at 0° C. room temperature, followed by stirring for 20 minutes. Methanol (1.0 mL) was added to the reaction mixture, and sodium sulfate decahydrate (4.74 g, 14.7 mmol) and chloroform (30 mL) were added thereto, followed by stirring at room temperature for 8 hours. The reaction mixture was filtered through a celite, and the filtrate was concentrated under reduced pressure to yield a residue. The residue was purified by silica gel column chromatography to obtain (1R, 3aR,3bR,5aS,7S,9aR,9bR,11aR)-9a,11a-dimethyl-1-[(R)-6-methylheptan-2-yl]hexadecahydrobenzo[c]cyclopenta[h] chromen-5,7-diol (146 mg, 43%).

$^1$H NMR (CDCl$_3$) δ(ppm): 0.82 (s, 3H), 0.85 (d, J=7.0 Hz, 3H), 0.88 (d, J=7.0 Hz, 3H), 0.91 (d, J=6.9 Hz, 3H), 0.95-1.92 (m, 26H), 1.97-2.12 (m, 2H), 2.34 (m, 1H), 3.65 (m, 1H), 4.22 (m, 1H), 4.78 (m, 1H).

Step 7; By using (1R,3aR,3bR,5aS,7S,9aR,9bR,11aR)-9a, 11a-dimethyl-1-[(R)-6-methylheptan-2-yl]hexadecahydrobenzo[c]cyclopenta[h]chromen-5,7-diol (54.5 mg, 0.134 mmol) obtained in the Step 6, compound 93 (42.5 mg, 79%) was obtained in the same manner as Reference Example 4.

$^1$H NMR (CDCl$_3$) δ(ppm): 0.85 (d, J=7.0 Hz, 3H), 0.87 (s, 3H), 0.88 (d, J=7.0 Hz, 3H), 0.91 (d, J=6.9 Hz, 3H), 0.95-1.96 (m, 22H), 2.05-2.17 (m, 2H), 2.32-2.63 (m, 3H), 2.74 (dd, J=12.6, 16.2 Hz, 1H), 3.00 (dd, J=5.0, 12.6 Hz, 1H), 4.59 (m, 1H).

Example 79

(5S,8S,9S)-7-Oxa-8,9-epoxy-3,6-cholestadione (Compound 94)

Compound 1 (34.3 mg, 0.0856 mmol) obtained in Example 1 was dissolved in dichloromethane (1.0 mL), and 3-chloroperbenzoic acid (34.1 mg, 0.128 mmol) was added thereof at 0° C., followed by stirring for 90 minutes. A saturated aqueous sodium bicarbonate solution was added to the reaction mixture, followed by extraction with chloroform twice. The organic layer was dried over anhydrous sodium sulfate, and concentrated under reduced pressure to yield a residue. The residue was purified by preparative thin layer chromatography to obtain the title compound (10.1 mg, 29%).

$^1$H NMR (CDCl$_3$) δ(ppm): 0.78 (s, 3H), 0.86 (d, J=6.6 Hz, 3H), 0.88 (d, J=6.6 Hz, 3H), 0.92 (d, J=6.6 Hz, 3H), 0.99-1.70 (m, 15H), 1.81-2.11 (m, 8H), 2.41-2.58 (m, 3H), 2.71 (ddd, J=1.5, 4.8, 16.1 Hz, 1H), 3.15 (dd, J=4.5, 13.8 Hz, 1H).

Example 80

(1R,5aS,7S,9aR,9bR,11aR)-7-Hydroxy-9a,11a-dimethyl-1-[(R)-6-methylheptan-2-yl]-2,3,3,5a,6,7,8,9, 9a,9b,10,11,11a-dodecahydrobenzo[c]cyclopenta[h] chromen-5(1H)-one (Compound 99)

Compound 56 (2.10 g, 4.63 mmol) obtained in Example 46 was dissolved in tert-butanol (33 mL), and pyrimidium p-toluenesulfonate (35.0 g; 140 mmol) was added thereto, followed by stirring at 85° C. for 2 hours. A saturated aqueous sodium bicarbonate solution was added to the reaction mixture, followed by extraction with ethyl acetate twice. The organic layer was dried over anhydrous sodium sulfate, and concentrated under reduced pressure to yield a residue. The residue was purified by column chromatography to obtain the title compound (26 mg, 1.4%).

$^1$H NMR (CDCl$_3$) δ(ppm): 0.85 (s, 3H), 0.86 (d, J=6.6 Hz, 3H), 0.87 (d, J=7.0 Hz, 3H), 0.93 (s, 3H), 0.94 (d, J=6.6 Hz, 3H), 0.99-1.80 (m, 18H), 1.81-2.05 (m, 3H), 2.15-2.30 (m, 3H), 2.36-2.58 (m, 2H), 3.63 (m, 1H).

Example 81

(3S,5S)-7-Oxa-8-cholesten-6-on-3-ol isobutylate (Compound 100)

Compound 2 (60 mg, 0.15 mmol) obtained in Example 2 was dissolved in dichloromethane (0.75 mL), and isobutyric acid chloride (0.032 mL, 0.30 mmol) and pyridine (0.19 mL, 0.60 mmol) were added thereto, followed by stirring at 0° C. for 1 hour. A saturated aqueous sodium bicarbonate solution was added to the reaction mixture, followed by extraction with ethyl acetate twice. The organic layer was dried over anhydrous sodium sulfate, and concentrated under reduced pressure to yield a residue. The residue was purified by preparative thin layer chromatography to obtain the title compound (67 mg, 95%).

$^1$H NMR (CDCl$_3$) δ(ppm): 0.68 (s, 3H), 0.79-1.62 (m, 15H), 0.86 (d, J=6.6 Hz, 3H), 0.87 (d, J=6.6 Hz, 3H), 0.94 (d, J=6.5 Hz, 3H), 0.99 (s, 3H), 1.15 (d, J=6.9 Hz, 3H), 1.16 (d, J=7.1 Hz, 3H), 1.63-1.82 (m, 3H), 1.86-2.40 (m, 6H), 2.45 (dd, J=13, 3.4 Hz, 1H), 2.56 (qq, J=6.6, 6.6 Hz, 1H), 4.71 (ddd, J=5.0, 5.0, 5.0 Hz, 1H).

Example 82

(3S,5S)-7-Oxa-8-cholesten-6-on-3-ol furan-2-carboxylate (Compound 101)

Compound 2 (51 mg, 0.13 mmol) obtained in Example 2 was dissolved in dichloromethane (0.65 mL), and furan-2-carboxylic acid chloride (0.025 mL, 0.26 mmol) and pyridine (0.041 mL, 0.51 mmol) were added thereto, followed by stirring at 0° C. for 3 hours. A saturated aqueous sodium bicarbonate solution was added to the reaction mixture, followed by extraction with ethyl acetate twice. The organic layer was dried over anhydrous sodium sulfate, and concentrated under reduced pressure. A residue obtained by concentrating the organic layer under reduced pressure was purified by preparative thin layer chromatography to obtain the title compound (65 mg, 100%).
$^1$H NMR (CDCl$_3$) δ(ppm): 0.68 (s, 3H), 0.81-1.87 (m, 17H), 0.87 (d, J=6.4 Hz, 3H), 0.88 (d, J=6.6 Hz, 3H), 0.94 (d, J=6.4 Hz, 3H), 1.03 (s, 3H), 1.91-2.55 (m, 8H), 5.00 (dddd, J=4.8, 4.7, 4.7, 4.6 Hz, 1H), 6.51 (dd, J=3.5, 1.8 Hz, 1H), 7.17 (dd, J=3.5, 0.7 Hz, 1H), 7.58 (dd, J=1.8, 0.7 Hz, 1H).

Example 83

(S)-3-Methoxyimino-7-oxa-8-cholesten-6-one (Compound 102)

Compound 1 (40 mg, 0.10 mmol) obtained in Example 1 was dissolved in ethanol (5 mL), and O-methylhydroxyamine hydrochloride (25 mg, 0.30 mmol) and pyridine (0.024 mL, 0.03 mmol) were added thereto, followed by stirring at room temperature for 3 hours. A saturated aqueous ammonium chloride solution was added to the reaction mixture, followed by extraction with ethyl acetate twice. The organic layer was dried over anhydrous sodium sulfate, and concentrated under reduced pressure to yield a residue. The residue was purified by preparative thin layer chromatography to obtain the title compound (39 mg, 93%) as an E/Z mixture.
$^1$H NMR (CDCl$_3$) δ(ppm): 0.69 (s, 1.5H), 0.69 (s, 1.5H), 0.80-1.62 (m, 16H), 0.87 (d, J=6.6 Hz, 1.5H), 0.87 (d, J=6.6 Hz, 1.5H), 0.88 (d, J=6.6 Hz, 1.5H), 0.88 (d, J=6.6 Hz, 1.5H), 0.94 (d, J=6.3 Hz, 1.5H), 0.94 (d, J=6.3 Hz, 1.5H), 1.63-2.48 (m, 9.5H), 2.49 (dd, J=14, 4.3 Hz, 0.5H), 2.53 (dd, J=14, 3.6 Hz, 0.5H), 2.76 (ddd, J=14, 3.6, 1.3 Hz, 0.5H), 3.24 (ddd, J=14, 4.9, 1.7 Hz, 0.5H), 3.62 (ddd, J=14, 4.3, 1.3 Hz, 0.5H), 3.81 (s, 1.5H), 3.82 (s, 1.5H).

Example 84

(3R,5S)-3-Fluoro-7-oxa-8-cholesten-6-one (Compound 103) and (5S)-7-oxa-3,8-cholestadien-6-one (Compound 104)

Compound 2 (80 mg, 0.20 mmol) obtained in Example 2 was dissolved in dichloromethane (8 mL), and diethylaminosulfur trifluoride (0.057 mL, 0.40 mmol) was added thereto, followed by stirring at 0° C. for 3 hours. Water was added to the reaction mixture, followed by extraction with ethyl acetate twice. The organic layer was dried over anhydrous sodium sulfate, and concentrated under reduced pressure to yield a residue. The residue was purified by preparative thin layer chromatography to obtain compound 103 (44 mg, 54%) and compound 104 (29 mg, 37%).
Compound 103; $^1$H NMR (CDCl$_3$) δ(ppm): 0.68 (s, 3H), 0.80-2.48 (m, 24H), 0.87 (d, J=6.6 Hz, 3H), 0.88 (d, J=6.6 Hz, 3H), 0.94 (d, J=6.6 Hz, 3H), 0.95 (s, 3H), 2.80 (dd, J=13, 3.7 Hz, 1H), 4.95 (br d, J=47 Hz, 1H).
Compound 104; $^1$H NMR (CDCl$_3$) δ(ppm): 0.69 (s, 3H), 0.76-1.67 (m, 12H), 0.87 (d, J=6.6 Hz, 3H), 0.88 (d, J=6.6 Hz, 3H), 0.93 (s, 3H), 0.94 (d, J=6.6 Hz, 3H), 1.74 (m, 1H), 1.86-2.53 (m, 9H), 2.59 (dd, J=11, 5.5 Hz, 1H), 5.61 (m, 1H), 5.73 (m, 1H).

Example 85

(3S,5S)-3-Fluoro-7-oxa-8-cholesten-6-one (Compound 106)

Compound 105 (93 mg, 0.23 mmol) obtained in the Step 1 of Example 10 was dissolved in dichloromethane (9 mL), and diethylaminosulfur trifluoride (0.066 mL, 0.46 mmol) was added thereto, followed by stirring at 0° C. for 3 hours. Water was added to the reaction mixture, followed by extraction with ethyl acetate twice. The organic layer was dried over anhydrous sodium sulfate, and concentrated under reduced pressure to yield a residue. The residue was purified by preparative thin layer chromatography to obtain the title compound (11 mg, 12%).
$^1$H NMR (CDCl$_3$) δ(ppm): 0.68 (s, 3H), 0.80-2.54 (m, 25H), 0.87 (d, J=6.6 Hz, 3H), 0.88 (d, J=6.6 Hz, 3H), 0.93 (d, J=6.6 Hz, 3H), 1.00 (s, 3H), 4.95 (dtt, J=47, 11, 5.5 Hz, 1H).

Example 86

(1R,5aS,7S,9aS,11aR)-7-Hydroxy-9a,11a-dimethyl-1-[(R)-6-methylheptan-2-yl]-1,2,5a,6,7,8,9,9a,10,11,11a-decahydrobenzo[c]cyclopenta[h]chromen-5(10H)-one (Compound 107)

Compound 56 (2.9 g, 6.6 mmol) obtained in Example 46 was dissolved in tert-butanol (47 mL), and pyrimidium p-toluenesulfonate (50.0 g; 200 mmol) was added thereto, followed by stirring at 80° C. for 2 hours. A saturated aqueous sodium bicarbonate solution was added to the reaction mixture, followed by extraction with ethyl acetate twice. The organic layer was dried over anhydrous sodium sulfate, and concentrated under reduced pressure to yield a residue. The residue was purified by column chromatography to obtain the title compound (3.6 mg, 0.14%).
$^1$H NMR (CDCl$_3$) δ(ppm): 0.84-1.69 (m, 12H), 0.86 (s, 3H), 0.87 (d, J=6.6 Hz, 3H), 0.88 (d, J=6.6 Hz, 3H), 0.94 (d, J=6.6 Hz, 3H), 1.03 (s, 3H), 1.76 (m, 1H), 1.87-2.22 (m, 3H), 2.23-2.87 (m, 7H), 3.66 (m, 1H), 5.76 (br s, 1H).

Example 87

(3S,5R)-3-Hydroxy-3-methyl-7-oxa-8-cholesten-6-one (Compound 108) and (3S,5S)-3-hydroxy-3-methyl-7-oxa-8-cholesten-6-one (Compound 109)

Compound 1 (73 mg, 0.18 mmol) obtained in Example 1 was dissolved in THF (6.0 mL), a 3.0 mol/L THF solution of methylmagnesium chloride (0.12 mL, 0.37 mmol) was added thereto at −78° C., followed by stirring at the same temperature for 2.5 hours. Water was added to the reaction mixture, followed by extraction with ethyl acetate twice. The organic layer was dried over anhydrous sodium sulfate, and concentrated under reduced pressure to yield a residue. The residue was purified by preparative thin layer chromatography to obtain compound 108 (36 mg, 41%) and compound 109 (43 mg, 49%).

Compound 108; $^1$H NMR (CDCl$_3$) δ(ppm): 0.68 (s, 3H), 0.81-1.87 (m, 19H), 0.87 (d, J=6.6 Hz, 3H), 0.88 (d, J=6.6 Hz, 3H), 0.92 (s, 3H), 0.93 (d, J=6.6 Hz, 3H), 1.31 (s, 3H), 1.89-2.43 (m, 6H), 2.87 (dd, J=13, 3.6 Hz, 1H).

Compound 109; $^1$H NMR (CDCl$_3$) δ(ppm): 0.68 (s, 3H), 0.80-1.82 (m, 19H), 0.87 (d, J=6.6 Hz, 3H), 0.88 (d, J=6.6 Hz, 3H), 0.94 (d, J=6.6 Hz, 3H), 0.97 (s, 3H), 1.26 (s, 3H), 1.89-2.42 (m, 6H), 2.43 (dd, J=13, 3.3 Hz, 1H).

Example 88

(1R,3aS,5aS,7S,9aS,11aR)-7-Hydroxy-9a,11a-dimethyl-1-[(R)-6-methylheptan-2-yl]-1,2,3,3a,5a,6,7,8,9,9a,11,11a-dodecahydrobenzo[c]cyclopenta[h]chromen-5(10H)-one (Compound 110)

Compound 56 (110 mg, 0.250 mmol) in obtained in Example 46 was dissolved in tert-butanol (5 mL), and pyrimidium p-toluenesulfonate (1.9 g; 7.4 mmol) was added thereto, followed by stirring at 80° C. for 1 hour. A saturated aqueous sodium bicarbonate solution was added to the reaction mixture, followed by extraction with ethyl acetate twice. The organic layer was dried over anhydrous sodium sulfate, and concentrated under reduced pressure to yield a residue. The residue was purified by column chromatography to obtain the title compound (84 mg, 85%).

$^1$H NMR (CDCl$_3$) δ(ppm): 0.75-1.60 (m, 15H), 0.83 (d, J=6.6 Hz, 3H), 0.84 (d, J=6.6 Hz, 3H), 0.89 (s, 3H), 0.90 (d, J=6.6 Hz, 3H), 0.92 (s, 3H), 1.62-2.20 (m, 9H), 2.21-2.38 (m, 2H), 3.62 (m, 1H).

Example 89

(S)-2-[(1R,3aR,5aS,7S,9aS,11aR)-7-Methoxymethoxy-9a,11a-dimethyl-5-oxo-1,2,3a,5,5a,6,7,8,9,9a,10,11,11a-tetradecahydrobenzo[c]cyclopenta[h]chromen-1-yl]propanal (Compound III)

Compound 95 (20 mg, 0.051 mmol) obtained in Example 67 was dissolved in dichloromethane (3 mL), and 1,1,1-triacetoxy-1,1-dihydro-1,2-benziodoxol-3(1H)one (Dess-Martin Periodinane) (65 mg, 0.15 mmol) was added thereto, followed by stirring at room temperature for 40 minutes. A saturated aqueous sodium bicarbonate solution was added to the reaction mixture, followed by extraction with chloroform (20 mL×3). The organic layer was washed with saturated brine, dried over anhydrous magnesium sulfate, and concentrated to yield a residue, which was purified by silica gel column chromatography (25% to 50% ethyl acetate/n-hexane) to obtain the title compound (11 mg, 53%).

$^1$H NMR δ(ppm, CDCl$_3$): 9.61 (1H, d, J=2.9 Hz), 4.75-4.65 (2H, m), 3.53 (1H, m), 3.39 (3H, s), 2.45-1.22 (18H, m), 1.15 (3H, d, J=6.8 Hz), 0.98 (3H, s), 0.73 (3H, s).

Example 90

(1R,3aR,5aS,7S,9aS,11aR)-1-[(S)-1-Isobutylaminopropan-2-yl]-7-methoxymethoxy-9a,11a-dimethyl-1,2,3,3a,5a,6,7,8,9,9a,11,11a-dodecahydrobenzo[c]cyclopenta[h]chromen-5(10H)-one (Compound 69)

Compound III (23 mg, 0.059 mmol) obtained in Example 89 was dissolved in THF (3 mL), and isobutyl amine (30 μL, 0.30 mmol) and sodium triacetoxyborohydride (62 mg, 0.30 mmol) were added thereto, followed by stirring at room temperature for 1 hour. Water was added to the reaction mixture, followed by extraction with ethyl acetate (10 mL×2). The organic layer was dried over anhydrous magnesium sulfate, and concentrated to yield a residue. The residue was purified by silica gel column chromatography (50% ethyl acetate/n-hexane) to obtain the title compound (6.0 mg, 22%).

$^1$H NMR δ(ppm, CDCl$_3$): 4.75-4.65 (2H, m), 3.52 (1H, m), 3.38 (3H, s), 2.77 (1H, m), 2.57-1.25 (23H, m), 1.10 (3H, d, J=6.4 Hz), 0.99-0.96 (9H, m), 0.70 (3H, s).

Example 91

(1R,3aR,5aS,7S,9aS,11aR)-7-Hydroxy-1-[(S)-1-isobutylaminopropan-2-yl]-9a,11a-dimethyl-1,2,3,3a,5a,6,7,8,9,9a,11,11a-dodecahydrobenzo[c]cyclopenta[h]chromen-5(10H)-one (Compound 83)

By using compound 69 obtained in Example 90, the title compound was obtained in the same manner as Example 48.

$^1$H NMR δ(ppm, CDCl$_3$): 3.65 (1H, m), 2.78 (1H, m), 2.60-1.25 (24H, m), 1.10 (3H, d, J=6.5 Hz), 0.98-0.96 (9H, m), 0.69 (3H, s).

Example 92

(1R,3aR,5aS,7S,9aS,11aR)-7-Methoxymethoxy-9a,11a-dimethyl-1[(S)-1-morpholinopropan-2-yl]-1,2,3,3a,5a,6,7,8,9,9a,11,11a-dodecahydrobenzo[c]cyclopenta[h]chromen-5(10H)-one (Compound 72)

By using morpholine and compound III obtained in Example 89, the title compound was obtained in the same manner as Example 90.

$^1$H NMR δ(ppm, CDCl$_3$): 4.75-4.65 (2H, m), 3.75-3.60 (4H, m), 3.53 (1H, m), 3.39 (3H, s), 2.49-1.15 (24H, m), 1.03 (3H, d, J=6.4 Hz), 0.98 (3H, s), 0.70 (3H, s).

Example 93

7-Oxa-ergosta-8(9),24(28)-dien-3,6-dione (Compound 112)

7-Oxa-ergosta-8(9),24(28)-dien-6-on-3-ol (10.6 mg, 0.0256 mmol) obtained in Reference Example 85 was dissolved in dichloromethane (2 mL), followed by cooling to 0° C., and Dess-Martin Periodinane (48.0 mg, 0.113 mmol) was added thereto, followed by stirring for 3 hours. An aqueous solution of sodium bicarbonate was added to the reaction mixture and extracted with chloroform (5 mL×3), followed by purification by silica gel column chromatography (33% ethyl acetate/n-hexane) to obtain the title compound (5.5 mg, 52%).

$^1$H NMR δ(ppm, CDCl$_3$): 4.73 (1H, br s), 4.66 (1H, br s), 2.81-2.73 (2H, m), 2.62-1.26 (21H, m), 1.17 (3H, s), 1.03 (6H, dd, J=1.8, 6.8 Hz), 0.98 (3H, d, J=6.6 Hz), 0.72 (3H, s).

Example 94

Proliferation Promoting Agent for Neural Stem Cells

A proliferation promoting agent for neural stem cells containing Compound 1 is obtained by preparing a DMSO solution of Compound 1 (0.1 mmol/L) according to the conventional method.

INDUSTRIAL APPLICABILITY

The present invention can be used for a promoting proliferation of neural stem cells for the purpose of treatment of disease such as Parkinson's disease, Alzheimer's disease, Down syndrome, cerebrovascular disorders, stroke, spinal cord injury, triplet repeat disease, multiple sclerosis, amyotrophic lateral sclerosis, polyneuropathy, epilepsy, anxiety disorders, schizophrenia, depression or manic depressive psychosis.

The invention claimed is:

1. A sterol derivative represented by the general formula (I):

[Chem. 29]

(I)

[wherein Y represents optionally substituted lower alkyl or optionally substituted lower alkenyl, $X^a$ and $X^b$ are the same or different, and represent a bond or —$NR^a$— (wherein $R^a$ represents a hydrogen atom, optionally substituted lower alkyl, optionally substituted cycloalkyl, optionally substituted lower alkanoyl, or optionally substituted aroyl), $R^1$, $R^2$, $R^3$, $R^4$, $R^7$ and $R^8$ are the same or different, and represent a hydrogen atom or hydroxy, or $R^1$ and $R^2$, $R^3$ and $R^4$, or $R^7$ and $R^8$ together represent =O, $R^5$ and $R^6$ are the same or different, and represent a hydrogen atom, halogen, azido, hydroxy, optionally substituted lower alkoxy, optionally substituted cycloalkyloxy, optionally substituted lower alkenyloxy, optionally substituted lower alkynyloxy, optionally substituted aryloxy, optionally substituted aromatic heterocyclyloxy, optionally substituted aliphatic heterocyclyloxy, optionally substituted lower alkanoyloxy, optionally substituted aroyloxy, optionally substituted aromatic heterocyclylcarbonyloxy, or —$NR^bR^c$ (wherein $R^b$ and $R^c$ are the same or different, and represent a hydrogen atom, optionally substituted lower alkyl, optionally substituted lower alkenyl, optionally substituted cycloalkyl, optionally substituted aryl, an optionally substituted aromatic heterocyclic group, an optionally substituted aliphatic heterocyclic group, optionally substituted lower alkanoyl, optionally substituted aroyl, optionally substituted lower alkoxycarbonyl, optionally substituted aryloxycarbonyl, optionally substituted aromatic heterocyclyloxycarbonyl, optionally substituted lower alkylcarbamoyl, optionally substituted di-lower alkylcarbamoyl, optionally substituted arylcarbamoyl, optionally substituted aromatic heterocyclylcarbamoyl, optionally substituted arylsulfonyl, or optionally substituted lower alkylsulfonyl), or $R^5$ and $R^6$ together represent O=, $R^dON$= (wherein $R^d$ represents a hydrogen atom, optionally substituted lower alkyl, optionally substituted cycloalkyl, optionally substituted aryl, an optionally substituted aromatic heterocyclic group, or an optionally substituted aliphatic heterocyclic group), or $R^eR^fC$= (wherein $R^e$ and $R^f$ are the same or different, and represent a hydrogen atom, halogen, optionally substituted lower alkyl, optionally substituted lower alkenyl, optionally substituted lower alkynyl, optionally substituted cycloalkyl, optionally substituted aryl, an optionally substituted aromatic heterocyclic group, an optionally substituted aliphatic heterocyclic group, optionally substituted lower alkoxy, optionally substituted aryloxy, optionally substituted aromatic heterocyclyloxy, optionally substituted lower alkanoyl, optionally substituted aroyl, optionally substituted lower alkanoyloxy, or optionally substituted aroyloxy), $R^9$ represents a hydrogen atom, optionally substituted lower alkyl, optionally substituted lower alkenyl, optionally substituted lower alkynyl, or optionally substituted cycloalkyl, or $R^1$ and $R^3$, $R^3$ and $R^5$ (provided that this is only when $X^a$ is a bond), $R^5$ and $R^7$ (provided that this is only when $X^b$ is a bond), or $R^7$ and $R^9$ together represent a bond or an oxygen atom, and regarding $R^{10}$, $R^{11}$ and $R^{12}$, $R^{10}$ and $R^{11}$ together represent a bond or an oxygen atom and $R^{12}$ represents a hydrogen atom, or $R^{10}$ and $R^{12}$ together represent a bond or an oxygen atom and $R^{11}$ represents a hydrogen atom] (provided that compounds represented by the following formulas (P) and (Q) are excluded), or a pharmaceutically acceptable salt thereof

[Chem. 30]

(P)

(Q)

2. The sterol derivative or the pharmaceutically acceptable salt thereof according to claim 1, wherein $R^{10}$ and $R^{11}$ together represent a bond and $R^{12}$ is a hydrogen atom.

3. The sterol derivative or the pharmaceutically acceptable salt thereof according to claim 1, wherein $X^a$ and $X^b$ are bonds.

4. The sterol derivative or the pharmaceutically acceptable salt thereof according to claim 1, wherein $R^7$ and $R^8$ are hydrogen atoms.

5. The sterol derivative or the pharmaceutically acceptable salt thereof according to claim 1, wherein $R^5$ is a hydrogen atom.

6. The sterol derivative or the pharmaceutically acceptable salt thereof according to claim 1, wherein $R^6$ is hydroxy, optionally substituted lower alkoxy, optionally substituted cycloalkyloxy, optionally substituted lower alkenyloxy, optionally substituted lower alkynyloxy, optionally substituted aryloxy, optionally substituted aromatic heterocyclyloxy, optionally substituted aliphatic heterocyclyloxy, optionally substituted lower alkanoyloxy, optionally substituted aroyloxy, or $-NR^{b1}R^{c1}$ (wherein $R^{b1}$ and $R^{c1}$ are the same or different, and represent a hydrogen atom, optionally substituted lower alkyl, optionally substituted lower alkanoyl, or optionally substituted aroyl).

7. The sterol derivative or the pharmaceutically acceptable salt thereof according to claim 1, wherein $R^6$ is hydroxy, optionally substituted lower alkoxy, optionally substituted aryloxy, optionally substituted aromatic heterocyclyloxy, optionally substituted aliphatic heterocyclyloxy, or $-NR^{b1}R^{c1}$ (wherein $R^{b1}$ and $R^{c1}$ have the same meanings as defined above, respectively).

8. The sterol derivative or the pharmaceutically acceptable salt thereof according to claim 1, wherein $R^6$ is hydroxy or optionally substituted lower alkoxy.

9. The sterol derivative or the pharmaceutically acceptable salt thereof according to claim 1, wherein $R^5$ and $R^6$ together represent $O=$ or $R^dON=$ (wherein $R^d$ has the same meaning as defined above).

10. The sterol derivative or the pharmaceutically acceptable salt thereof according to claim 1, wherein $R^9$ is a hydrogen atom or optionally substituted lower alkyl.

11. The sterol derivative or the pharmaceutically acceptable salt thereof according to claim 1, wherein Y is optionally substituted lower alkyl.

12. The sterol derivative or the pharmaceutically acceptable salt thereof according to claim 1, wherein Y is optionally substituted lower alkenyl.

* * * * *